United States Patent [19]
Goulet et al.

[11] Patent Number: 5,849,764
[45] Date of Patent: Dec. 15, 1998

[54] ANTAGONISTS OF GONADOTROPIN RELEASING HORMONE

[75] Inventors: Mark Goulet, Westfield; Lin Chu, Scotch Plains; Thomas F. Walsh, Watchung; Michael H. Fisher, Ringoes; Narindar N. Girotra, Old Bridge; Matthew J. Wyvratt, Mountainside; Peter Lin, Edison; Wallace T. Ashton, Clark, all of N.J.

[73] Assignee: Merck & Co., Inc., Rahway, N.J.

[21] Appl. No.: 760,817

[22] Filed: Dec. 5, 1996

[51] Int. Cl.$^6$ .......................... A61K 31/44; A61K 31/40; C07D 215/12; C07D 209/02
[52] U.S. Cl. .......................... 514/337; 514/414; 514/418; 514/415; 514/379; 514/255; 514/256; 514/247; 514/253; 544/124; 544/360; 544/364; 546/277.4; 546/157; 546/122; 546/176; 546/193; 548/455
[58] Field of Search .................................. 546/277.4, 157, 546/122, 176, 193; 548/455; 549/241, 247; 544/124, 360, 364; 514/414, 418, 415, 337, 379, 255, 256, 247, 253

[56] References Cited

U.S. PATENT DOCUMENTS

| | | | |
|---|---|---|---|
| 4,252,803 | 2/1981 | Webb | 514/415 |
| 4,544,663 | 10/1985 | Manning et al. | 514/378 |
| 5,030,640 | 7/1991 | Fisher | 514/339 |

FOREIGN PATENT DOCUMENTS

| | | |
|---|---|---|
| 0219292 | 4/1987 | European Pat. Off. |
| 0679642 A1 | 11/1995 | European Pat. Off. |
| 2181559 | 4/1972 | France |
| WO 90/05721 | 10/1989 | WIPO |
| WO 95/28405 | 4/1995 | WIPO |
| WO 95/29900 | 4/1995 | WIPO |

OTHER PUBLICATIONS

Biswanath De, et al. J. Med. Chem.;32, pp. 2036–2038 (1989).

Medline 90228198, abstract of Drugs, 39(3), pp. 399–437, Mar. 1990.

Medline 90276263, abstract of Drugs, (Apr. 1990), vol. 39(4), pp. 523–551, Chrisp.

Medline 88103867, abstract of Rubinow, American J of Obstetrics and Gynecology, (Jan. 1988), vol. 158(1), pp. 5–11.

Medline 80054722, abstract of Silman, Nature, vol. 282(5736), pp. 301–303, Nov. 1979.

Medline 95188753, abstract of Polsker, Drugs, vol. 48(6), pp. 930–967, Dec. 1994.

Medline 95088771, abstract of Garner, Journal of Obstetric, Gynecologic, and Neonatal Nursing, vol. 23(7), pp. 563–570, Sep. 1994.

*Primary Examiner*—John Kight
*Assistant Examiner*—D. Margaret M. Mach
*Attorney, Agent, or Firm*—Elliott Korsen; Mark R. Daniel

[57] ABSTRACT

There are disclosed compounds of formula (I)

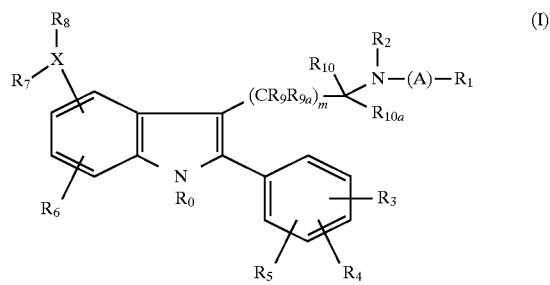

and pharmaceutically acceptable salts thereof which are useful as antagonists of GnRH and as such may be useful for the treatment of a variety of sex-hormone related and other conditions in both men and women.

27 Claims, No Drawings

ANTAGONISTS OF GONADOTROPIN RELEASING HORMONE

This application claiming priority to Provisional Application No. 60/008,634, filed Dec. 14, 1995.

BACKGROUND OF THE INVENTION

The gonadotropin-releasing hormone (GnRH), also referred to as luteinizing hormone-releasing hormone (LHRH), is a decapeptide that plays a key role in human reproduction. The hormone is released from the hypothalamus and acts on the pituitary gland to stimulate the biosynthesis and secretion of luteinizing hormone (LH) and follicle-stimulating hormone (FSH). LH released from the pituitary gland is primarily responsible for the regulation of gonadal steroid production in both sexes, whereas FSH regulates spermatogenesis in males and follicular development in females. GnRH agonists and antagonists have proven effective in the treatment of certain conditions which require inhibition of LH/FSH release. In particular, GnRH-based therapies have proven effective in the treatment of endometriosis, uterine fibroids, polycystic ovarian disease, precocious puberty and several gonadal steroid-dependent neoplasia, most notably cancers of the prostate, breast and ovary. GnRH agonists and antagonists have also been utilized in various assisted fertilization techniques and have been investigated as a potential contraceptive in both men and women. They have also shown possible utility in the treatment of pituitary gonadotrophe adenomas, sleep disorders such as sleep apnea, irritable bowel syndrome, premenstrual syndrome, benign prostatic hyperplasia, hirsutism, as an adjunct to growth hormone therapy in growth hormone deficient children, and in murine models of lupus. The compounds of the invention may also be used in combination with bisphosphonates (bisphosphonic acids) and other agents, such as growth hormone secretagogues, e.g. MK-0677, for the treatment and the prevention of disturbances of calcium, phosphate and bone metabolism, in particular, for the prevention of bone loss during therapy with the GnRH antagonist, and in combination with estrogens, progesterones, antiestrogens, antiprogestins and/or androgens for the prevention or treatment of bone loss or hypogonadal symptoms such as hot flashes during therapy with the GNRH antagonist.

Additionally, a compound of the present invention may be co-administered with a 5α-reductase 2 inhibitor, such as finasteride or epristeride; a 5α-reductase 1 inhibitor such as 4,7β-dimethyl-4-aza-5β-cholestan-3-one, 3-oxo-4-aza-4,7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

Current GnRH antagonists are GnRH-like decapeptides which are generally administered intravenously or subcutaneously presumably because of negligible oral activity. These have amino acid substitutions usually at positions one, two, three, six and ten.

Non-peptide GnRH antagonists offer the possible advantage of oral administration. Non-peptide GnRH antagonists have been described in European Application 0 219 292 and in De, B. et al., J. Med. Chem., 32, 2036–2038 (1989), in WO 95/28405, WO 95/29900 and EP 0679642 all to Takeda Chemical Industries, Ltd.

Substituted indoles known in the art include those described in the following patents and patent applications. U.S. Pat. No. 5,030,640 discloses alpha-heterocyclic ethanol aminoalkyl indoles which are potent β-agonists. U.S. Pat. No. 4,544,663 discloses indolamine derivatives which are allegedly useful as male anti-fertility agents. WO 90/05721 discloses alpha-amino-indole-3-acetic acids useful as anti-diabetic, anti-obesity and anti-atherosclerotic agents. French patent 2,181,559 discloses indole derivatives with sedative, neuroleptic, analgesic, hypotensive, antiserotonin and adrenolytic activity. Belgian patent 879381 discloses 3-aminoalkyl-1H-indole-5-thioamide and carboxamide derivatives as cardiovascular agents used to treat hypertension, Raynaud's disease and migraine.

SUMMARY OF THE INVENTION

The present invention relates to compounds which are non-peptide antagonists of GnRH which can be used to treat a variety of sex-hormone related conditions in men and women, to methods for their preparation, and to methods and pharmaceutical compositions containing said compounds for use in mammals.

Because of their activity as antagonists of the hormone GnRH, the compounds of the present invention are useful to treat a variety of sex-hormone related conditions in both men and women. These conditions include endometriosis, uterine fibroids, polycystic ovarian disease, hirsutism, precocious puberty, gonadal steroid-dependent neoplasias such as cancers of the prostate, breast and ovary, gonadotrophe pituitary adenomas, sleep apnea, irritable bowel syndrome, premenstrual syndrome and benign prostatic hypertophy. They are also useful as an adjunct to treatment of growth hormone deficiency and short stature, and for the treatment of systemic lupus erythematosis. Further, the compounds of the invention may be useful in in vitro fertilization and as contraceptives. The compounds may also be useful in combination with androgens, estrogens, progesterones, antiestrogens and antiprogestogens for the treatment of endometriosis, fibroids and in contraception. They may also be useful in combination with testosterone or other androgens or antiprogestogens in men as a contraceptive. The compounds may also be used in combination with an angiotensin-converting enzyme inhibitor such as Enalapril or Captopril, an angiotensin II-receptor antagonist such as Losartan or a renin inhibitor for the treatment of uterine fibroids. Additionally, the compounds of the invention may also be used in combination with bisphosphonates (bisphosphonic acids) and other agents, for the treatment and the prevention of disturbances of calcium, phosphate and bone metabolism, in particular, for the prevention of bone loss during therapy with the GnRH antagonist, and in combination with estrogens, progesterones and/or androgens for the prevention or treatment of bone loss or hypogonadal symptoms such as hot flashes during therapy with the GnRH antagonist.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4,7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

DETAILED DESCRIPTION OF THE INVENTION

The present invention relates to compounds of the general formula

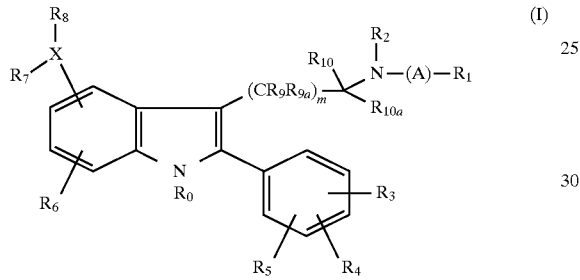

wherein

A is $C_1-C_6$ alkyl, substituted $C_1-C_6$ alkyl, $C_3-C_7$ cycloalkyl, substituted $C_3-C_7$ cycloalkyl, $C_3-C_6$ alkenyl, substituted $C_3-C_6$ alkenyl, $C_3-C_6$ alkynyl, substituted $C_3-C_6$ alkynyl, $C_1-C_6$ alkoxy, or $C_0-C_5$ alkyl-S(O)$_n$-$C_0-C_5$ alkyl, $C_0-C_5$ alkyl-O-$C_0-C_5$ alkyl, $C_0-C_5$ alkyl-NR$_{18}$-$C_0-C_5$ alkyl where $R_{18}$ and the $C_0-C_5$ alkyl can be joined to form a ring,

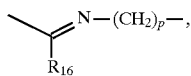

or a single bond.

$R_0$ is hydrogen, $C_1-C_6$ alkyl, substituted $C_1-C_6$ alkyl, wherein the substituents are as defined below; aryl, substituted aryl, aralkyl or substituted aralkyl, wherein the substituents are as defined for $R_3$, $R_4$ and $R_5$.

$R_1$ is

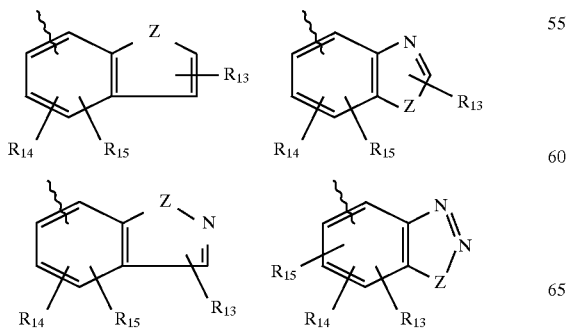

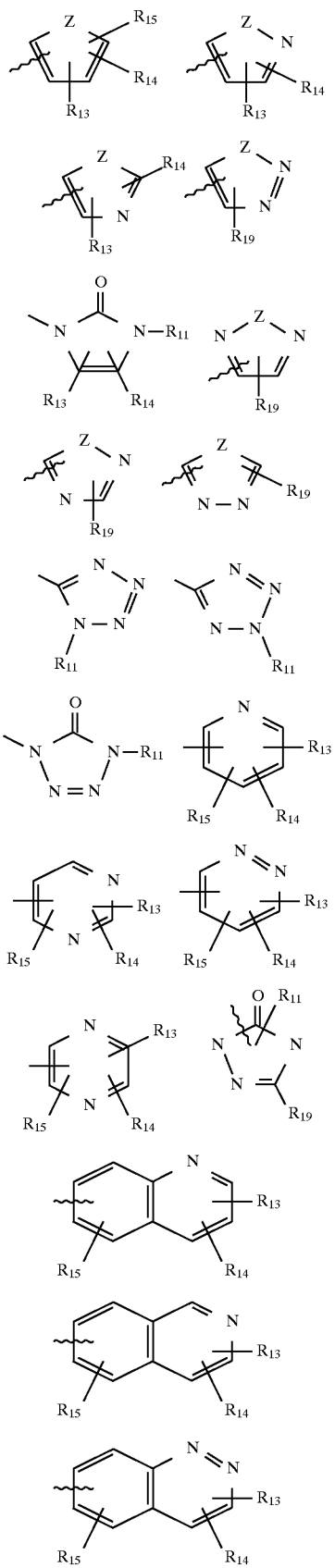

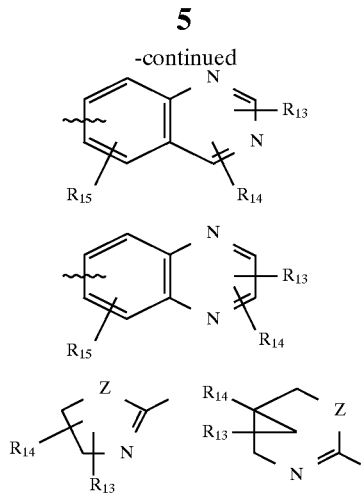

$R_2$ is hydrogen, $C_1$–$C_6$ alkyl, substituted $C_1$–$C_6$ alkyl, aralkyl, substituted aralkyl, aryl, substituted aryl, alkyl —$OR_{11}$, $C_1$–$C_6(NR_{11}R_{12})$, $C_1$–$C_6(CONR_{11}R_{12})$ or $C(NR_{11}R_{12})NH$;

$R_2$ and A taken together form a ring of 5–7 atoms;

$R_3$, $R_4$ and $R_5$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O)O(CH_2)_p$—; $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl, aryl or substituted aryl;

$R_3$ and $R_4$ taken together form a carbocyclic ring of 3–7 carbon atoms or a heterocyclic ring containing 1–3 heteroatoms selected from N, O and S;

$R_6$ is hydrogen, $C_1$–$C_6$ alkyl, substituted $C_1$–$C_6$ alkyl, aryl, substituted aryl, $C_1$–$C_3$ perfluoroalkyl, CN, $NO_2$, halogen, $R_{11}O(CH_2)_p$—, $NR_{12}C(O)R_{11}$, $NR_{12}C(O)NR_{11}R_{12}$ or $SO_nR_{11}$;

$R_7$ is hydrogen, $C_1$–$C_6$ alkyl, or substituted $C_1$–$C_6$ alkyl, unless X is hydrogen or halogen, then $R_7$ is absent;

$R_8$ is hydrogen, $C(O)OR_9$, $C(O)NR_{11}R_{12}$, $NR_{11}R_{12}$, $C(O)R_{11}$, $NR_{12}C(O)R_{11}$, $NR_{12}C(O)NR_{11}R_{12}$, $NR_{12}S(O)_2R_{11}$, $NR_{12}S(O)_2NR_{11}R_{12}$, $OC(O)R_{11}$, $OC(O)NR_{11}R_{12}$, $OR_{11}$, $SO_nR_{11}$, $S(O)_nNR_{11}R_{12}$, $C_1$–$C_6$ alkyl or substituted $C_1$–$C_6$ alkyl, unless X is hydrogen or halogen, then $R_8$ is absent; or $R_7$ and $R_8$ taken together form a carbocyclic ring of 3–7 atoms;

$R_9$ and $R_{9a}$ are independently hydrogen, $C_1$–$C_6$ alkyl, substituted $C_1$–$C_6$ alkyl; aryl or substituted aryl, aralkyl or substituted aralkyl when m≠0; or $R_9$ and $R_{9a}$ taken together form a carbocyclic ring of 3–7 atoms or

when m≠0;

$R_9$ and A taken together form a heterocyclic ring containing 3–7 carbon atoms and one or more heteroatoms when m≠0; or $R_{10}$ and $R_{10a}$ are independently hydrogen, $C_1$–$C_6$ alkyl, substituted $C_1$–$C_6$ alkyl, aryl, substituted aryl, aralkyl or substituted aralkyl; or $R_{10}$ and $R_{10a}$ taken together form a carbocyclic ring of 3–7 atoms or

$R_9$ and $R_{10}$ taken together form a carbocyclic ring of 3–7 carbon atoms or a heterocyclic ring containing one or more heteroatoms when m≠0; or $R_9$ and $R_2$ taken together form a heterocyclic ring containing 3–7 carbon atoms and one or more heteroatoms when m≠0; or $R_{10}$ and $R_2$ taken together form a heterocyclic ring containing 3–7 carbon atoms and one or more heteroatoms;

$R_{10}$ and A taken together form a heterocyclic ring containing 3–7 carbon atoms and one or more heteroatoms; or $R_{11}$ and $R_{12}$ are independently hydrogen, $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

$R_{11}$ and $R_{12}$ taken together can form an optionally substituted ring of 3–7 atoms;

$R_{13}$ is hydrogen, OH, $NR_7R_8$, $NR_{11}SO_2(C_1$–$C_6$ alkyl), $NR_{11}SO_2$(substituted $C_1$–$C_6$ alkyl), $NR_{11}SO_2$(aryl), $NR_{11}SO_2$(substituted aryl), $NR_{11}SO_2(C_1$–$C_3$ perfluoroalkyl); $SO_2NR_{11}(C_1$–$C_6$ alkyl), $SO_2NR_{11}$l (substituted $C_1$–$C_6$ alkyl), $SO_2NR_{11}$(aryl), $SO_2NR_{11}$ (substituted aryl), $SO_2NR_{11}(C_1$–$C_3$ perfluoroalkyl); $SO_2NR_{11}(C(O)C_1$–$C_6$ alkyl);

$SO_2NR_{11}(C(O)$-substituted $C_1$–$C_6$ alkyl); $SO_2NR_{11}(C(O)$-aryl); $SO_2NR_{11}(C(O)$-substituted aryl); $S(O)_n(C_1$–$C_6$ alkyl); $S(O)_n$ (substituted $C_1$–$C_6$ alkyl), $S(O)_n$(aryl), $S(O)_n$ (substituted aryl), $C_1$–$C_3$ perfluoroalkyl, $C_1$–$C_3$ perfluoroalkoxy, $C_1$–$C_6$ alkoxy, substituted $C_1$–$C_6$ alkoxy, COOH, halogen, $NO_2$ or CN;

$R_{14}$ and $R_{15}$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl, aryl or substituted aryl;

$R_{16}$ is hydrogen, $C_1$–$C_6$ alkyl, substituted $C_1$–C6 alkyl, or $N(R_{11}R_{12})$;

$R_{18}$ is hydrogen, $C_1$–$C_6$ alkyl, substituted $C_1$–$C_6$ alkyl, $C(O)OR_9$, $C(O)NR_{11}R_{12}$, $C(O)R_{11}$, $S(O)_nR_{11}$;

$R_{19}$ is either the definition of $R_{13}$ or $R_{14}$;

X is hydrogen, halogen, N, O, $S(O)_n$, $C(O)$, $(CR_{11}R_{12})_p$; $C_2$–$C_6$ alkenyl, substituted $C_2$–$C_6$ alkenyl, $C_2$–$C_6$ alkynyl, or substituted $C_2$–$C_6$ alkynyl; when X is hydrogen or halogen, $R_7$ and $R_8$ are absent; when X is O, $S(O)_n$, $C(O)$, or $CR_{11}R_{12}$ only $R_7$ or $R_8$ is possible;

Z is O, S, or $NR_{11}$;

m is 0–3;

n is 0–2;

p is 0–4; and the alkyl, alkenyl and alkynyl substituents are selected from $C_1$–$C_6$ alkyl, $C_3$–$C_7$ cycloalkyl, aryl, substituted aryl, aralkyl, substituted aralkyl, hydroxy, oxo, cyano, $C_1$–$C_6$ alkoxy, fluoro, $C(O)OR_{11}$, aryl $C_1$–$C_3$ alkoxy, substituted aryl $C_1$–$C_3$ alkoxy, and the aryl substituents are as defined for $R_3$, $R_4$ and $R_5$;

or a pharmaceutically acceptable addition salt and/or hydrate thereof, or where applicable, a geometric or optical isomer or racemic mixture thereof.

Unless otherwise stated or indicated, the following definitions shall apply throughout the specification and claims.

When any variable (e.g., aryl, heterocycle, $R_1$, etc.) occurs more than one time in any constituent or in formula I, its definition on each occurrence is independent of its definition at every other occurrence. Also, combinations of substituents and/or variables are permissible only if such combinations result in stable compounds.

The term "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), secbutyl (s-Bu), tertbutyl (t-Bu), isopentane, isohexane, etc.

The term "aryl" includes phenyl and naphthyl. Preferably, aryl is phenyl.

The term "halogen" or "halo" is intended to include fluorine, chlorine, bromine and iodine.

As used herein, the term "composition" is intended to encompass a product comprising the specified ingredients in the specified amounts, as well as any product which results, directly or indirectly, from combination of the specified ingredients in the specified amounts It is intended that the connecting group A can be bonded to any of the available carbon or heteroatoms of the heteroaromatic groups $R_1$, including both rings of the benzo-fused heterocyclic groups and, likewise, $R_{13}$, $R_{14}$, and $R_{15}$ can be bonded to any of the available carbon atoms of the heteroaromatic groups $R_1$.

In addition, it is well known to those skilled in the art that many of the foregoing heterocyclic groups can exist in more than one tautomeric form. It is intended that all such tautomers be included within the ambit of this invention.

The optical isomeric forms, that is mixtures of enantiomers or diasteromers, e.g., racemates, as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical formula or name shall encompass pharmaceutically acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts Examples of acid salts are hydrochloric, nitric, sulfuric, phosphoric, formic, acetic, trifluoroacetic, propionic, maleic, succinic, malonic, methane sulfonic and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, omithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The compounds of the invention are prepared by the following reaction schemes. All substituent are as defined above unless indicated otherwise.

Scheme A

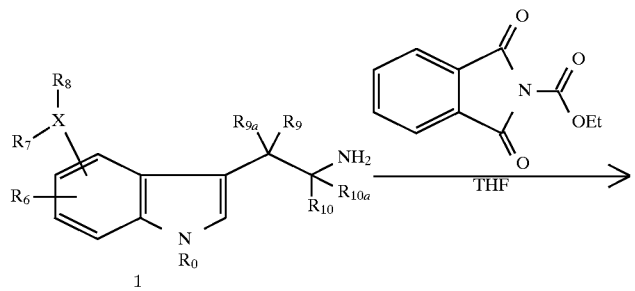

-continued
Scheme A

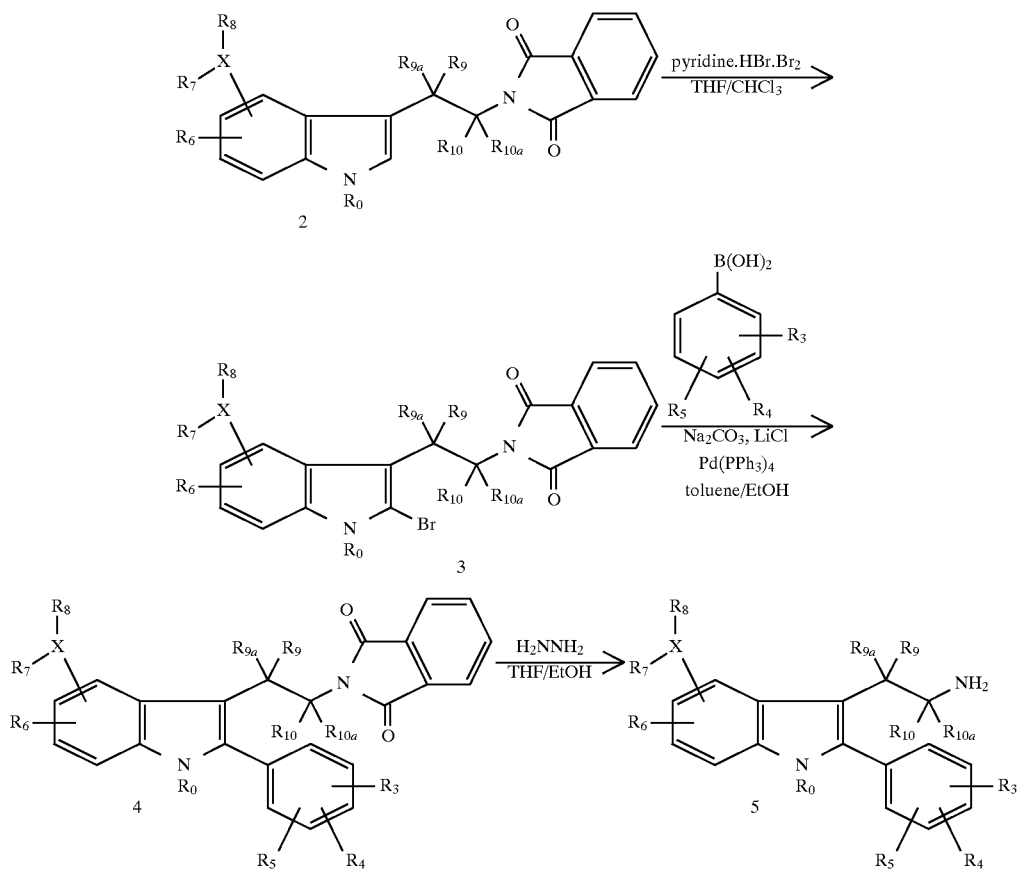

Reaction Scheme A

As shown in reaction Scheme A, treatment of tryptamine (1) with N-carboxyphthalimide in an inert organic solvent such as tetrahydrofuran at a temperature of 20°–65° C., preferably 65° C., for a period of 12–48 hours gives the corresponding N-phthalimidotryptamine derivative (2). The N-phthalimidotryptamine (2) could be further modified by treatment with a brominating agent such as pyridinium hydrobromide perbromide, pyrrolidone hydrotribromide, or the like in an inert organic solvent such as tetrahydrofuran, methylene chloride, chloroform, or mixtures thereof at 0°–25° C. for a period of 30 minutes to 4 hours to provide the 2-bromotryptamine (3). Bromide (3) may be reacted with an arylboronic acid (prepared essentially as described in: Gronowitz, S.; Hornfeldt, A. -B.; Yang, Y. -H. *Chem. Scr.* 1986, 26, 311–314.) with palladium (0) catalysis, a weak base such as aqueous sodium carbonate or the like, and a chloride source such as lithium chloride in an inert solvent like toluene, benzene, ethanol, propanol or mixtures thereof at a temperature of 25°–100° C., preferably 80° C., for a period of 1–6 hours to give the 2-aryltryptamine derivative (4). Finally, the phthalimido group may be removed by treatment of (4) with aqueous hydrazine in an inert solvent such as methanol or ethanol at a temperature of 0°–25° C. for a period of 4–24 hours to give tryptamine (5).

Scheme B

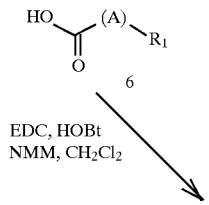

EDC, HOBt
NMM, CH$_2$Cl$_2$

-continued
Scheme B

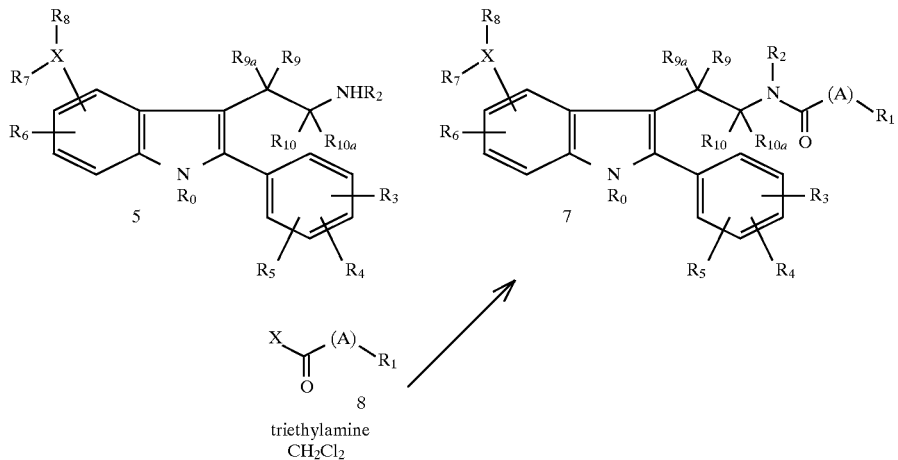

triethylamine
CH₂Cl₂

Reaction Scheme B

As shown in reaction Scheme B, the 2-aryltryptamine may be condensed with a carboxylic acid of type (6) using the coupling reagent 1-(3-dirnethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours to provide the corresponding amide derivative (7). Alternatively, 2-aryltryptamine (5) can be treated with an active ester or acid chloride of type (8) in an inert organic solvent such as methylene chloride, chloroform, tetrahydrofuran, diethyl ether, or the like and a tertiary amine base such as triethylamine, diisopropylethylamine, pyridine or the like at a temperature of 0°–25° C. for 30 minutes to 4 hours to give (7).

Scheme C

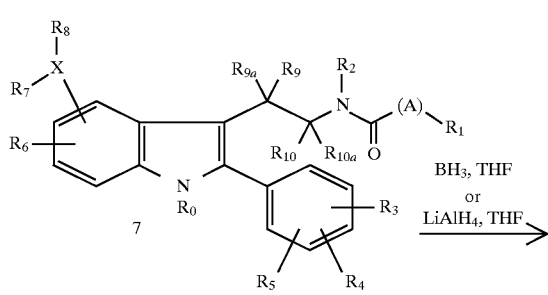

-continued
Scheme C

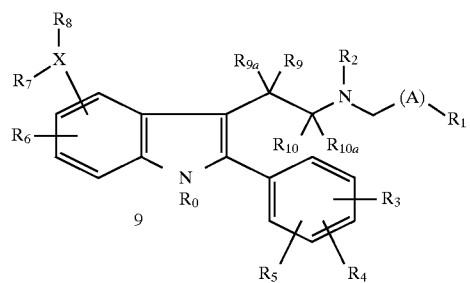

Reaction Scheme C

As shown in reaction Scheme C, the amide carbonyl of (7) can be reduced by treatment with borane, lithium aluminum hydride, or equivalent hydride sources in an inert organic solvent such as tetrahydrofuran, diethyl ether, 1,4-dioxane or the like at 25°–100° C., preferably 65° C., for a period of 1–8 hours to give the corresponding amine compound (9).

Scheme D

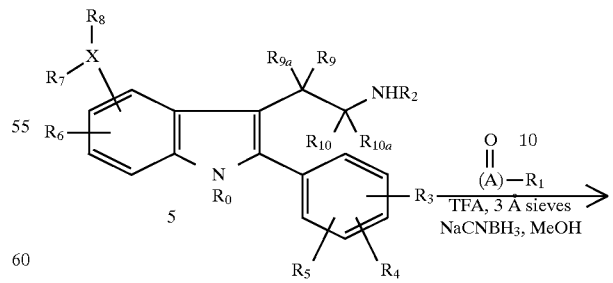

-continued
Scheme D

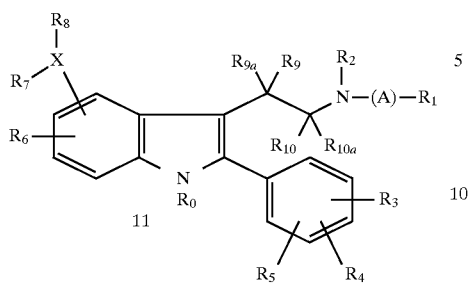

Reaction Scheme D

As shown in reaction Scheme D, the 2-aryltryptamine (5) can be modified by treatment with an aldehyde or ketone of type (10) in the presence of a weak acid such as trifluoroacetic acid (TFA), acetic acid or the like, with or without a dessicant such as 3 Å molecular sieves or magnesium sulfate, and a hydride source such as sodium borohydride or sodium cyanoborohydride, in an inert organic solvent such as methanol, ethanol, isopropanol, tetrahydrofuran, dichloromethane, chloroform, or mixtures thereof at a temperature of 0°–25° C. for a period of 1–12 hours to give the corresponding secondary or teriary amine derivative (11).

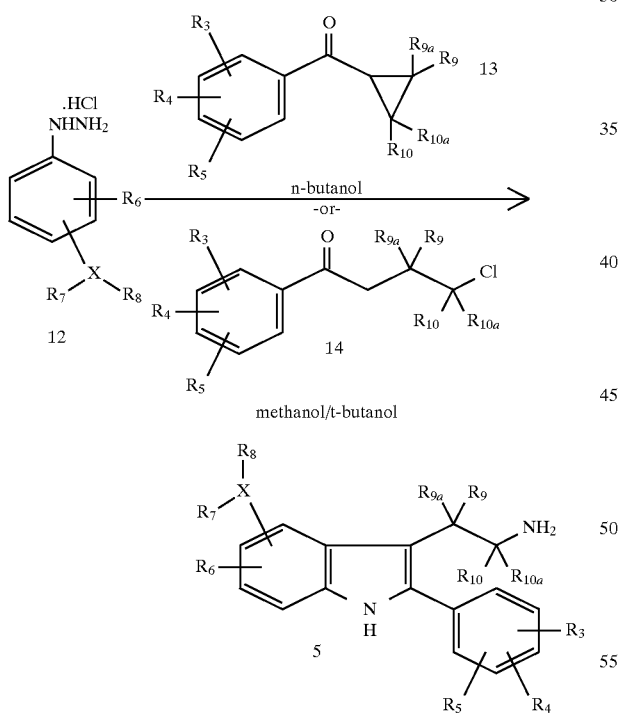

Reaction Scheme E

As shown in reaction Scheme E, treatment of an arylhydrazine or arylhydrazine hydrochloride (12) with an arylcyclopropylketone of type (13) in a polar organic solvent such as methanol, ethanol, n-propanol, isopropanol, n-butanol, t-butanol, preferably n-butanol, at a temperature of 70°–120° C. for a period of 8-24 hours gives 2-aryltryptamine (5). Alternatively, when an arylhydrazine or arylhydrazine hydrochloride (12) is treated with an arylbutyl ketone of type (14) containing a leaving group (chloride, bromide, iodide, O-methansulfonate, O-trifluoromethansulfonate, or the like) at the 4-position in a polar solvent such as methanol, ethanol, n-propanol, isopropanol, n-butanol, t-butanol, or mixtures thereof at room temperature for a period of 30 minutes to 2 hours followed by heating to a temperature of 65°–100° C. for 4–24 hours, 2-aryltryptamine (5) is produced.

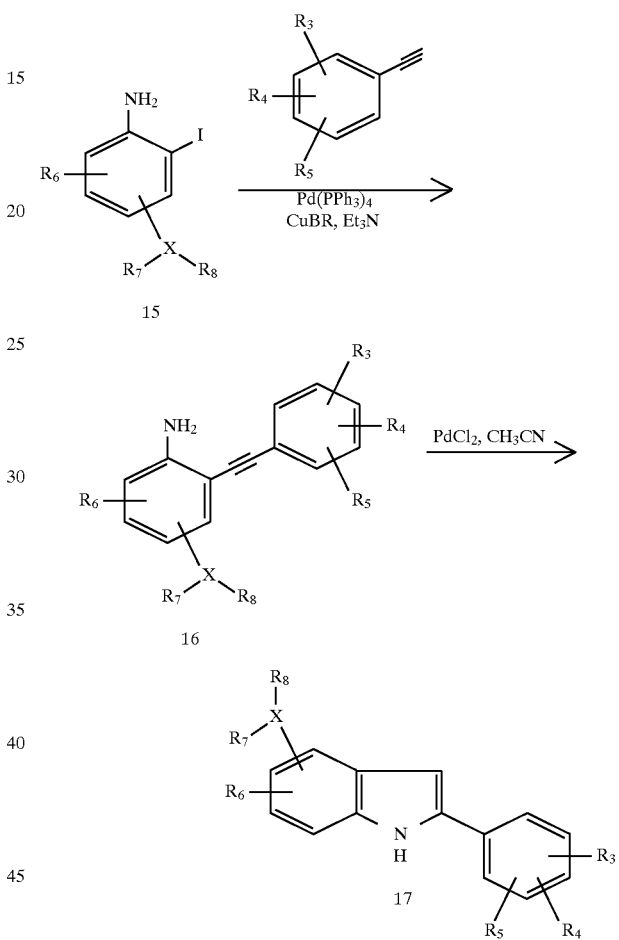

Reaction Scheme F

As shown in reaction Scheme F, iodoanilines of type (15) may be reacted with aryl acetylenes, an appropriate palladium (0) catalyst such as tetrakis(triphenylphosphine) palladium, a copper (I) halide such as cuprous bromide in an inert organic solvent such as triethylamine at a temperature of 50°–88° C. for a period of 30 minutes to 5 hours to provide the diarylacetylene (16). Acetylene (16) may be further modified by treatment with a palladium (II) catalyst such as palladium (II) chloride or palladium (II) acetate in an inert organic solvent such as acetonitrile at a temperature of 50°–82° C. for a period of 30 minutes to 6 hours to give 2-arylindole (17).

Scheme G

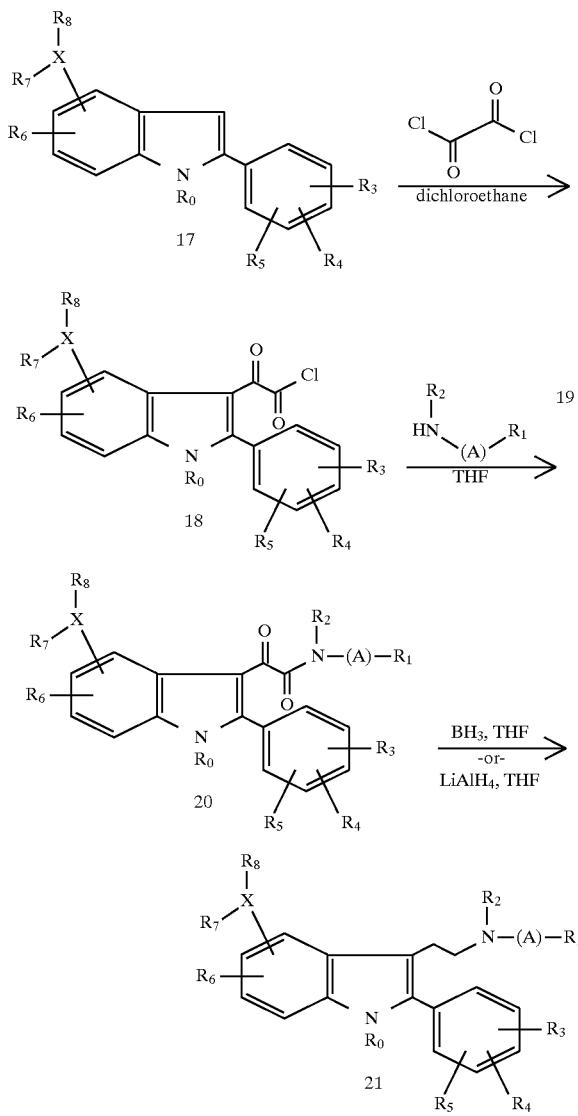

Reaction Scheme G

As shown in reaction Scheme G, treatment of 2-arylindole (17) with oxalyl chloride neat or in an inert organic solvent such as methylene chloride, chloroform, dichloroethane, tetrahydrofuran or the like at a temperature of 25°–65° C. for a period of 3–24 hours gives the acylchloride adduct (18). The crude product (18) may be reacted with an amine of type (19) in an inert organic solvent such as diethylether, tetrahydrofuran, methylene chloride, chloroform or the like and an amine base such as triethylamine, diisopropylethylamine or pyridine at a temperature of 0°–25° C. for a period of 30 minutes to 4 hours to provide the amide derivative (20). Amide (20) may be further modified by treatment with a reducing agent such as borane or lithium aluminum hydride in an inert organic solvent such as tetrahydrofuran at elevated temperatures, preferably reflux, for a period of 1–5 hours to give compound (21).

Scheme H

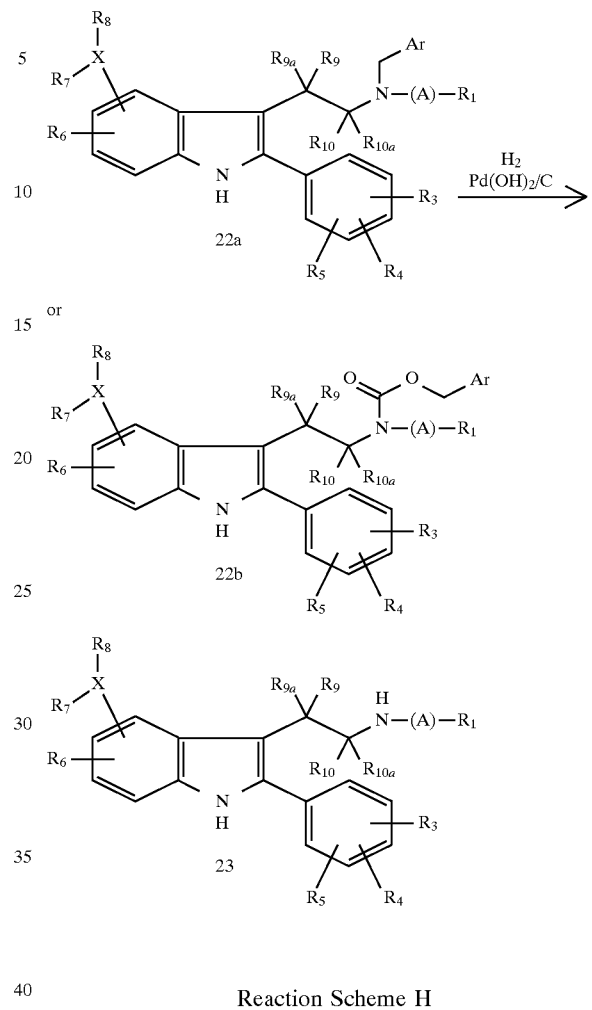

Reaction Scheme H

As shown in reaction Scheme H, N-benzyl derivatives of type (22a) or N-benzyloxycarbonyl derivatives of type (22b) may be reduced to provide the secondary amine analogs (7) by treatment with hydrogen (1 atm) and an appropriate catalyst such as palladium on carbon, palladium hydroxide on carbon, or the like in an inert organic solvent such as tetrahydrofuran, ethyl acetate, methanol, ethanol, or mixtures thereof to which has been added a weak acid such as 30% aqueous acetic acid for a period of 10 minutes to 3 hours or until the aryl group has been removed to give the secondary amine.

Scheme I

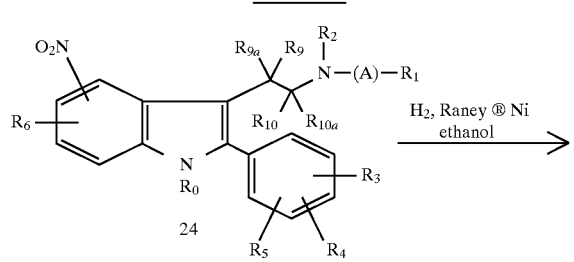

-continued
Scheme I

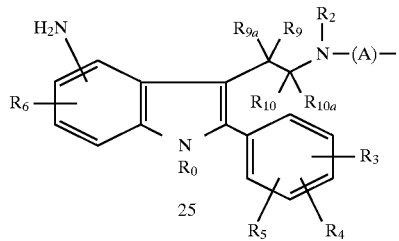

25

Reaction Scheme I

As shown in reaction Scheme I, treatment of a nitroindole of type (24) with hydrogen (1 atm) and an appropriate catalyst such as Raney® Nickel in an inert organic solvent such as ethanol, methanol, or the like at room temperature for a period of 2–12 hours gives the corresponding aminoindole derivative (25).

conditions. For example, treatment of (25) with an acid chloride, acid anhydride or active ester and an amine base such as triethylamine, diisopropylethylamine, pyridine, or the like in an inert organic solvent such as methylene chloride, chloroform, tetrahydrofuran, or mixtures thereof at 0° C. to room temperature for a period of 1 to 12 hours gives the corresponding amide or ester derivatives (26). Alternatively (25) may be coupled with a carboxylic acid by one of the many dehydrating agents commonly employed. For instance, treatment of amninoindole (25) with an appropriate carboxylic acid and 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours provides the corresponding amide or ester derivative (26).

Scheme J

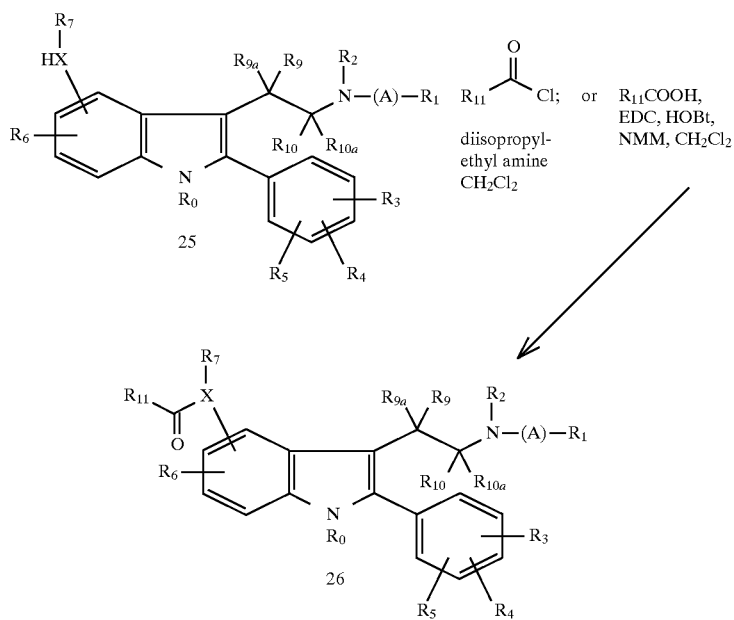

Reaction Scheme J

As shown in reaction Scheme J, amino- or hydroxyindole (25) may be modified by acylation under a variety of

Scheme K

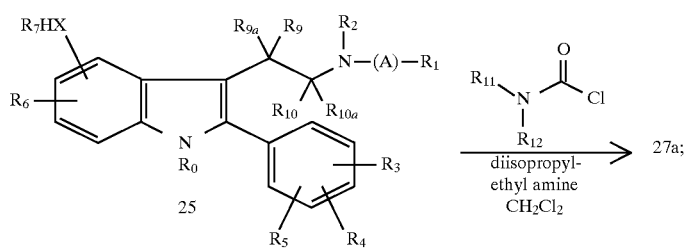

-continued
Scheme K

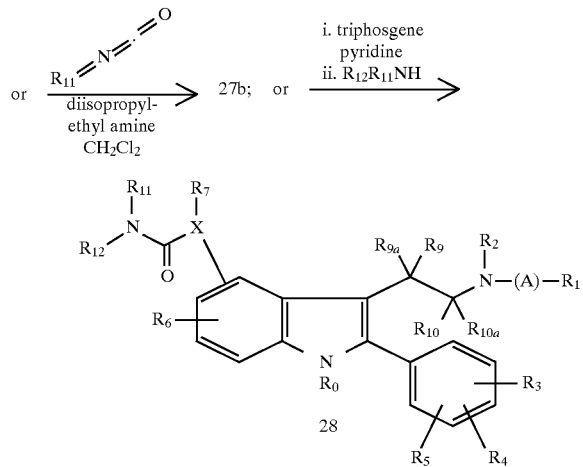

Reaction Scheme K

As shown in reaction Scheme K, urea or carbamate derivatives of (25) can be prepared by treatment with a carbamoyl chloride of type (27a), or alternatively with an isocyanate reagent of type (27b), and an amine base such as pyridine, triethylamine, diisopropylethylamine, N-methylmorpholine or the like in an inert organic solvent such as methylene chloride, chloroform, dimethylformamide, tetrahydrofuran or mixtures thereof at a temperature of 0°–65° C. for a period of 1–72 hours to give (28). Compound (25) can also be modified by treatment with a bis(electrophilic) reagent such as phosgene, triphosgene, 1,1'-carbonyldiimidazole, N,N'-disuccinimidyl carbonate, or the like with or without the addition of an amine base such as pyridine, triethylamine, diisopropylethylamine, N-methylmorpholine in an inert solvent such as methylene chloride, chloroform, or the like at a temperature of –20° to 0° C. for a period of 20 minutes to 2 hours. After this time, the reaction mixture is treated with an appropriate mono- or disubstituted amine at –20° to –25° C. for a period of 1–5 hours to give the urea or carbamate analog (28).

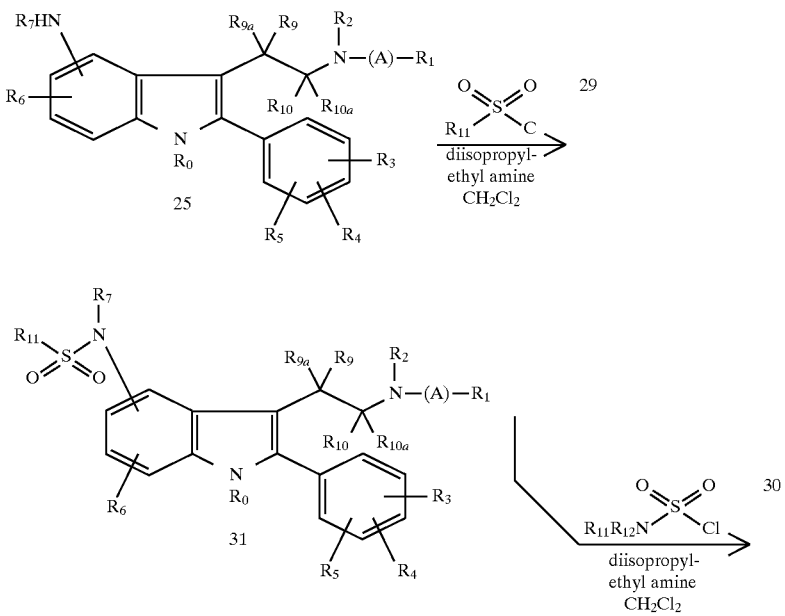

Scheme L

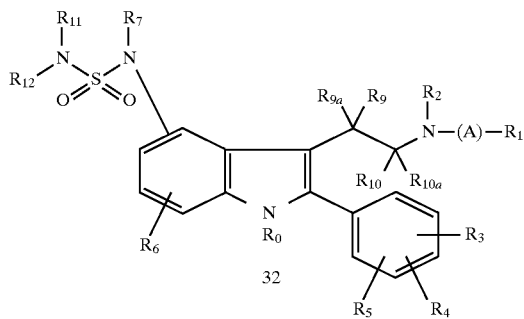

32

Reaction Scheme L

As shown in reaction Scheme L, amine (25) can be modified by treatment with an appropriate sulfonyl chloride of type (29) or sulfamyl chloride of type (30) with an amine base such as pyridine, triethylamine, diisopropylethylamine, N-methylmorpholine in an inert solvent such as methylene chloride, chloroform, dichloroethane or the like at a temperature of $-20°$–$25°$ C. for a period of 20 minutes to 2 hours to give the corresponding N-sulfonamide (31) or N-sulfamylamide (32) derivatives, respectively.

Scheme M

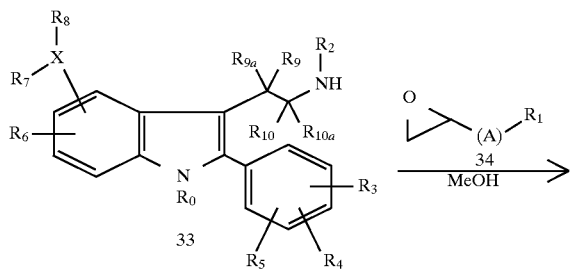

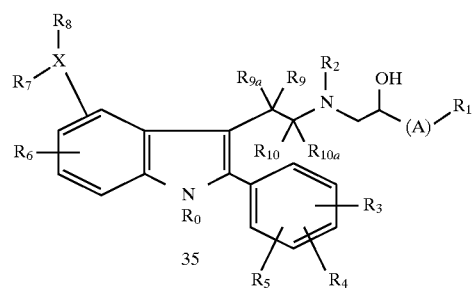

35

Reaction Scheme M

As shown in reaction Scheme M, the 2-aryltryptamine (33) can be modified by treatment with an epoxide such as (34) in an inert organic solvent such as methanol, ethanol, isopropanol, butanol, tert-butanol, or mixtures thereof at a temperature of $65°$–$110°$ C. for a period of 8–20 hours to give the corresponding amino-alcohol derivative (35).

Scheme N

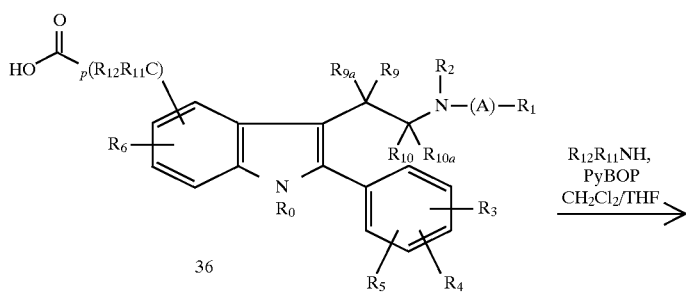

-continued
Scheme N

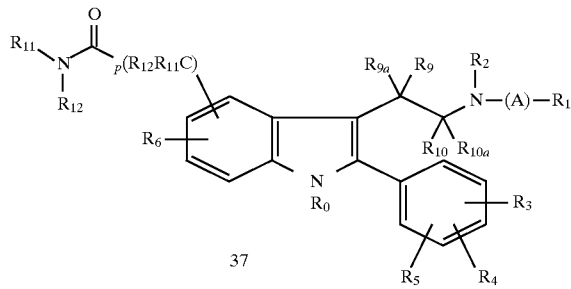

37

Reaction Scheme N

As shown in reaction Scheme N, amide derivatives of an an acid-containing indole derivative such as (36) can be prepared by treatment with an appropriate amine ($R_{12}R_{11}$ NH) and a suitable coupling agent such as benzotriazol-1-yloxy-tris(pyrrolidino)phosphonium hexafluorophosphate (PyBOP), benzotriazol-1-yloxy-tris(dimethylamino) phosphonium hexafluorophosphate (BOP), 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, tetrahydrofuran, dimethylformarnide, or mixtures thereof at or near room temperature for a period of 3–24 hours provides the corresponding amide derivative (37).

The compounds of the present invention are useful in the treatment of various sex-hormone related conditions in men and women. This utility is manifested in their ability to act as antagonists of the neuropeptide hormone GnRH as demonstrated by activity in the following in vitro assays.

Rat Pituitary GnRH Receptor Binding Assay

Crude plasma membranes prepared from rat pituitary tissues were incubated in a Tris.HCL buffer (50 mM, PH. 7.5) containing bovine serum albumin (0.1%), [I-125]D-t-Bu-Ser6-Pro9-ethyl amide-GnRH, and the desired concentration of a test compound. The assay mixtures were incubated at 4° C. for 90–120 minutes followed by rapid filtration and repeated washings through a glass fiber filter. The radioactivity of membrane bound radioligands was determined in a gamma-counter. From this data, the $IC_{50}$ of the radioligand binding to GnRH receptors in the presence of test compound was estimated.

Inhibition of LH Release Assay

Active compounds from the GnRH receptor binding assay were further evaluated with an in vitro LH release assay to confirm their antagonist activity (blocking GnRH-induced LH release).

1. Sample Preparation

The compounds to be assayed were dissolved and diluted in DMSO. The final concentration of DMSO in the incubation medium was 0.5%.

2. Assay

The Wistar male rats (150–200 grams) were obtained from Charles River Laboratories (Wilmington, Mass.). Rats were maintained at a constant temperature (25° C.) on a 12-hr light, 12-hr dark cycle. Rat chow and water were available ad libitum. The animals were sacrificed by decapitation and pituitary glands were aseptically removed and placed in Hank's Balanced Salt Solution (HBSS) in a 50-ml polypropylene centriguge tube. The collection tube was centrifuged for 5 min at 250×g, and HBSS was removed by aspiration. Pituitary glands were transferred to a disposable petri plate and minced with a scalpel. The minced tissue was then transferred to a 50-ml disposable centrifuge tube by suspending the tissue fragments in three successive 10-ml aliquots of HBSS containing 0.2% collagenase and 0.2% hyaluronidase. The cell dispersion was carried out in a water bath at 37° C. with gentle strring for 30 min. At the end of the incubation, the cells were aspirated 20 to 30 times with a pipet and the undigested pituitary fragments were allowed to settle for 3 to 5 min. The suspended cells were removed by aspiration, and then subjected to a 1200 g centrifugation for 5 min. The cells were then resuspended in Culture medium. The undigested pituitary fragments were treated with 30 ml aliquots of the digestion enzymes as above for a total of 3 digestions with the collagenase/hyaluronidase mixture. The resulting cell suspensions were pooled, counted and diluted to a concentration of $3 \times 10^5$ cells/ml, and 1.0 ml of this suspension was placed in each well of a 24-well tray (Costar, Cambridge, Mass.). Cells were maintained in a humidified 5% $CO_2$—95% air atmosphere at 37° C. for 3 to 4 days. The culture medium consisted of DMEM containing 0.37% $NaHCO_3$, 10% horse serum, 2.5% fetal bovine serum, 1% non-essential amino acids, 1% glutamine, and 0.1% gentamycin. On the day of an experiment, cells were washed three times 1 ½ hrs prior to and two more times immediately before the start of the experiment with DMEM containing 0.37% $NaHCO_3$, 10% horse serum, 2.5% fetal bovine serum, 1% non-essential amino acids(100X), 1% glutamine(100X), 1% Penicillin/Streptomycin(10,000 Units of Penicillin and 10,000 micrograms of Streptomycin per ml), and 25 mM HEPES, pH 7.4. LH release was initiated by adding 1 ml of fresh medium containing test compounds in the presence of 2 nM GNRH to each well in duplicate. Incubation was carried out at 37° C. for 3 hr. After incubation, medium was removed and centrifuged at 2,000×g for 15 min to remove any cellular material. The supernatant fluid was removed and assayed for LH content with a double antibody RIA procedure using materials obtained from Dr. A. F. Parlow (Harbor-UCLA Medical Center, Torrance, Calif.).

The compounds of formula I are useful in a number of areas affected by GnRH. They may be useful in sex-hormone related conditions, sex-hormone dependent cancers, benign prostatic hypertrophy or myoma of the uterus. Sex-hormone dependent cancers which may benefit from the administration of the compounds of this invention include prostatic cancer, uterine cancer, breast cancer and pituitary gonadotrophe adenomas. Other sex-hormone dependent conditions which may benefit from the administration of the compounds of this invention include endometriosis, polycystic ovarian disease, uterine fibroids and precocious puberty. The compounds may also be used in combination with an angiotensin-converting enzyme inhibitor such as Enalapril or Captopril, an angiotensin II-receptor antagonist such as Losartan or a renin inhibitor for the treatment of uterine fibroids.

The compounds of the invention may also be useful for controlling pregnancy, as a contraceptive in both men and women, for in vitro fertilization, in the treatment of premenstrual syndrome, in the treatment of lupus erythematosis, in the treatment of hirsutism, in the treatment of irritable bowel syndrome and for the treatment of sleep disorders such as sleep apnea.

A further use of the compounds of this invention is as an adjunct to growth hormone therapy in growth hormone deficient children. The compounds may be administered with growth hormone or a compound which increases the endogenous production or release of growth hormone. Certain compounds have been developed which stimulate the release of endogenous growth hormone. Peptides which are known to stimulate the release of endogenous growth hormone include growth hormone releasing hormone, the growth hormone releasing peptides GHRP-6 and GHRP-1 (described in U.S. Pat. No. 4,411,890, PCT Patent Pub. No. WO 89/07110, and PCT Patent Pub. No. WO 89/07111) and GHRP-2 (described in PCT Patent Pub. No. WO 93/04081), as well as hexarelin (*J. Endocrinol Invest.*, 15(Suppl 4), 45 (1992)). Other compounds which stimulate the release of endogenous growth hormone are disclosed, for example, in the following: U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289, PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; *Science* 260, 1640–1643 (Jun. 11, 1993); *Ann. Rep. Med. Chem.*, 28, 177–186 (1993); *Bioorg. Med. Chem. Ltrs.*, 4(22), 2709–2714 (1994); and *Proc. Natl. Acad. Sci. U.S.A.* 92, 7001–7005 (July 1995).

Representative preferred growth hormone secretageoues employed in the present combination include the following:

1) N-[1(R)-[(1,2-Dihydro-1-methanesulfonylspiro[3H-indole-3,4'-piperidin]-1-yl)carbonyl]-2-(1H-indol-3-yl)ethyl]-2-amino-2-methyl-propanamide;

2) N-[1(R)-[(1,2-Dihydro-1-methanecarbonylspiro[3H-indole-3,4'-piperidin]-1'-yl)carbonyl]-2-(1H-indol-3-yl)ethyl]-2-amino-2-methyl-propanamide;

3) N-[1(R)-[(1,2-Dihydro-1-benzenesulfonylspiro[3H-indole-3,4'-piperidin]-1'-yl)carbonyl]-2-(1H-indol-3-yl)ethyl]-2-amino-2-methyl-propanamide;

4) N-[1(R)-[(3,4-Dihydro-spiro[2H-1-benzopyran-2,4'-piperidin]-1'-yl) carbonyl]-2-(1H-indol-3-yl)ethyl]-2-amino-2-methylpropanamide;

5) N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methyl-propanamide;

6) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide;

7) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide methanesulfonate;

8) N-[1(R)-[(1,2-Dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;

9) N-[1(R)-[(1,2-Dihydro-1-methanesulfonyl-5-fluorospiro[3H-indole-3,4'-piperidin]-1'-yl)carbonyl]-2-(phenylmethyloxy)ethyl]-2-amino-2-methylpropanamide;

10) N-[1(S)-[(1,2-Dihydro-1-methanesulfonylspiro[3H-indole-3,4'-piperidin]-1'-yl) carbonyl]-2-(phenylmethylthio)ethyl]-2-amino-2-methylpropanamide;

11) N-[1(R)-[(1,2-Dihydro-1-methanesulfonylspiro [3H-indole-3,4'-piperidin]-1'-yl)carbonyl]-3-phenylpropyl]-2-amino-2-methyl-propanamide;

12) N-[1(R)-[(1,2-Dihydro-1-methanesulfonylspiro [3H-indole-3,4'-piperidin]-1'-yl)carbonyl]-3-cyclohexylpropyl]-2-amino-2-methyl-propanamide;

13) N-[1(R)-[(1,2-Dihydro-1-methanesulfonylspiro[3H-indole-3,4'-piperidin]-1'-yl)carbonyl]-4-phenylbutyl]-2-amino-2-methyl-propanamide;

14) N-[1(R)-[(1,2-Dihydro-1-methanesulfonylspiro [3H-indole-3,4'-piperidin]-1'-yl)carbonyl]-2-(5-fluoro-1H-indol-3-yl)ethyl]-2-amino-2-methylpropanamide;

15) N-[1(R)-[(1,2-Dihydro-1-methanesulfonyl-5-fluorospiro[3H-indole-3,4'-piperidin]-1'-yl)carbonyl]-2-(5-fluoro-1H-indol-3-yl)ethyl]-2-amino-2-methylpropanamide;

16) N-[1(R)-[(1,2-Dihydro-1-(2-ethoxycarbonyl)methylsulfonylspiro-[3H-indole-3,4'-piperidin]-1'-yl) carbonyl]-2-(1H-indol-3-yl)ethyl]-2-amino-2-methylpropanamide;

17) N-[1(R)-[(1,2-Dihydro-1,1-dioxospiro[3H-benzothiophene-3,4'-piperidin]-1'-yl)carbonyl]-2-(phenylmethyloxy)ethyl]-2-amino-2-methylpropanamide; and pharmaceutically acceptable salts thereof.

The compounds of the invention may also be used in combination with bisphosphonates (bisphosphonic acids) and other agents, such as growth hormone secretagogues, e.g. MK-0677, for the treatment and the prevention of disturbances of calcium, phosphate and bone metabolism, in particular, for the prevention of bone loss during therapy with the GnRH antagonist, and in combination with estrogens, progesterones and or androgens for the prevention or treatment of bone loss or hypogonadal symptoms such as hot flashes during therapy with the GnRH antagonist.

Bisphosphonates (bisphosphonic acids) are known to inhibit bone resorption and are useful for the treatment of bone lithiasis as disclosed in U.S. Pat. No. 4,621,077 to Rosini, et al.

The literature discloses a variety of bisphosphonic acids which are useful in the treatment and prevention of diseases involving bone resorption. Representative examples may be found in the following: U.S. Pat. No. 3,251,907; U.S. Pat. No. 3,422,137; U.S. Pat. No. 3,584,125; U.S. Pat, No. 3,940,436; U.S. Pat. No. 3,944,599; U.S. Pat. No. 3,962,432; U.S. Pat. No. 4,054,598; U.S. Pat. No. 4,267,108; U.S. Pat.

No. 4,327,039; U.S. Pat. No. 4,407,761; U.S. Pat. No. 4,578,376; U.S. Pat. No. 4,621,077; U.S. Pat. No. 4,624,947; U.S. Pat. No. 4,746,654; U.S. Pat. No. 4,761,406; U.S. Pat. No. 4,922,007; U.S. Pat. No. 4,942,157; U.S. Pat. No. 5,227,506; U.S. Pat. No. 5,270,365; EPO Patent Pub. No. 0,252,504; and *J. Org. Chem.*, 36, 3843 (1971).

The preparation of bisphosphonic acids and halo-bisphosphonic acids is well known in the art. Representative examples may be found in the above mentioned references which disclose the compounds as being useful for the treatment of disturbances of calcium or phosphate metabolism, in particular, as inhibitors of bone resorption.

Preferred bisphosphonates are selected from the group of the following compounds: alendronic acid, etidrononic acid, clodronic acid, pamidronic acid, tiludronic acid, risedronic acid, 6-amino-1-hydroxy-hexylidene-bisphosphonic acid, and 1-hydroxy-3(methylpentylamino)-propylidene-bisphosphonic acid; or any pharmaceutically acceptable salt thereof. A particularly preferred bisphosphonate is alendronic acid (alendronate), or a pharmaceutically acceptable salt thereof. An especially preferred bisphosphonate is alendronate sodium, including alendronate sodium trihydrate. Alendronate sodium has received regulatory approval for marketing in the United States under the trademark FOSAMAX®.

Additionally, a compound of the present invention may be co-administered with a 5α-reductase 2 inhibitor, such as finasteride or epristeride; a 5α-reductase 1 inhibitor such as 4,7β-dimethyl-4-aza-5α-cholestan-3-one, 3-oxo-4-aza-4, 7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

For combination treatment with more than one active agent, where the active agents are in separate dosage formulations, the active agents may be administered separately or in conjunction. In addition, the administration of one element may be prior to, concurrent to, or subsequent to the administration of the other agent.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethy-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural formula I useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500, milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The following examples illustrate the preparation of some of the compounds of the invention and are not to be construed as limiting the invention disclosed herein.

EXAMPLE 1

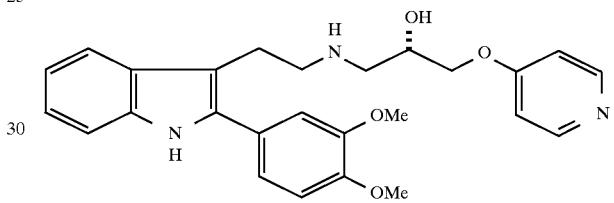

1-[2-[2-(3,4-dimethoxyphenyl)-1H-indol-3-yl]ethylamino]-3-(pyridin-4-yloxy)propan-2-ol To a solution of 2-[2-(3,4-dimethoxyphenyl)-1H-indol-3-yl]-ethylamine (118 mg in 4 mL dry methanol) was added 20 mg of 4-oxiranylnethoxypyridine and the mixture heated to 80° C. on an oil bath. After 6 hours the mixture was concentrated in vacuo and purified by flash chromatography on silica gel (methylene chloride:methanol:ammonium hydroxide, 90:10:1) to provide the title compound (53 mg). m/e=448 (M+H)

Following a procedure similar to that described in Example 1, the following compounds were prepared:

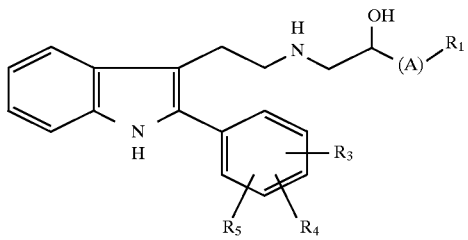

| Example # | $R_1$ | $R_3,R_4,R_5$ | A | m/e |
|---|---|---|---|---|
| 1A | Pyridine-4-NH—COCH$_3$ | 3,4-OMe | CH$_2$—O | — |
| 1B | Pyridine-4-NH$_2$ | 3,4-OMe | CH$_2$—O | 463 (M + H) |

EXAMPLE 2.1

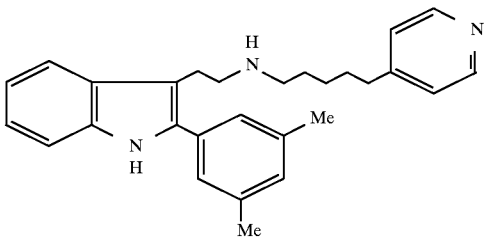

{2- [2-(3 5-dimethylphenyl)-1H-indol-3-yl]-ethyl}-(5-pyridin-4-yl-pentyl)-amine

Step 2.1A 2-[2-(1H-indol-3-yl)-ethyl]-isoindole-1,3-dione

To a stirred suspension of 2-(1H-indol-3-yl)ethylamine (2.0 g in 20 mL of dry tetrahydrofuran) was added N-carbethoxyphthalimide (2.85 g) and the mixture heated to reflux on an oil bath. After 48 hours the reaction was cooled to room temperature, filtered and the filtrate concentrated in vacuo. The resulting solid was suspended in a mixture of hexane/methylene chloride (2.5:1) and filtered. Purification of the collected solids by flash chromatography (methylene chloride:methanol, 97:3) gave the title compound (3.1 g).

Step 2.1B 2-[2-(2-bromo-1H-indol-3-yl)-ethyl]-isoindole-1,3-dione

To a solution of 2-[2-(1H-indol-3-yl)-ethyl]-isoindole-1,3-dione (1.0 g in a mixture of 10 mL dry tetrahydrofuran and 10 mL dry chloroform) at 0° C. was added pyridinium bromide perbromide (1.14 g) and the reaction stirred at 0° C. After 50 minutes, the reaction was quenched by the addition of saturated sodium bicarbonate and extracted with ethyl acetate. The organic portion was washed with saturated sodium bicarbonate (3x) and 0.3M sodium bisulfate (3x) then dried over magnesium sulfate. Purification of the concentrate by flash chromatography on silica gel (hexane:ethyl acetate, 3:1) gave the title compound (1.2 g).

Step 2.1C 2-{2-[2-(3,5-dimethylphenyl)-1H-indol-3-yl]-ethyl}-isoindole-1,3-dione To a solution of 2-[2-(2-bromo-1H-indol-3-yl)-ethyl]-isoindole-1,3-dione (150 mg in a mixture of 5 mL toluene and 5 mL ethanol) was added 3,5-dimethylphenyl boronic acid (85 mg) followed by 1.0 mL of 1M sodium carbonate. To the stirred solution was added lithium chloride (60 mg) followed by tetrakis(triphenylphosphine)palladium (28 mg) and the mixture heated to reflux on an oil bath. After 4 hours the mixture was cooled to room temperature and concentrated in vacuo. Purification by flash chromatography on silica gel (hexane:ethyl acetate, 5:1) gave the title compound (146 mg).

Step 2.1D 2-[2-(3,5-dimethylphenyl)-1H-indol-3-yl]-ethylamine

To a solution of 2-{2-[2-(3,5-dimethylphenyl)-1H-indol-3-yl]-ethyl}-isoindole-1,3-isoindole-1,3 -dione (87 mg in a mixture of 4 mL tetrahydrofuran and 4 mL ethanol) was added 0.6 mL of 95% aqueous hydrazine and the reaction stirred at room temperature. After 18 hours the mixture was concentrated in vacuo and purified by flash chromatography on silica gel (methylene chloride:methanol:ammonium hydroxide, 9:6:1) to provide the title compound (54 mg).

Step 2.1E {2-[2-(3 5-dimethylphenyl)-1H-indol-3-yl]-ethyl}-(5-pyridin-4-yl-pentyl)-amine To a solution of 2-[2-(3,5-dimethylphenyl)-1H-indol-3-yl]-ethylamine (162 mg) and 5-(4-pyridyl)-pentanal (100 mg in 2 mL dry chloroform) was added anhydrous magnesium sulfate (735 mg) and the mixture stirred at 0° C. for 15 minutes. At this time sodium borohydride (92.7 mg) was added followed by 3 mL dry methanol and the mixture stirred at 0° C. After 1 hour, the reaction was quenched by pouring into water (25 mL), stirred for 30 minutes then extracted with methylene chloride (4×25 mL). The combined organics were dried over potassium carbonate, concentrated in vacuo and the residue purified by flash chromatography on silica gel (methylene chloride:methanol, 95:5) to give the title compound (172 mg). m/e=412 (M+H)

PREPARATION OF SYNTHETIC INTERMEDIATES

Step A: 5-(4-pyridyl)-4-pentyn-1-ol

4-Bromopyridine hydrochloride salt (3.89 g) was dissolved in a solvent mixture comprising triethylamine (25 mL) and water (5 mL). Anhydrous lithium chloride (848 mg), cooper (I) bromide powder (30 mg) and 5-pent-4-yn-1-ol (1.68 g) was added to the pyridine salt and the mixture stirred and an active nitrogen gas stream passed gently through the solution for approximately 15 minutes after which time tetrakis(triphenylphosphine)-palladium (231.1 mg) was added. The reaction mixture was heated to reflux under a nitrogen atmosphere and maintained at reflux for 2.5 h after which heating was stopped and the reaction was set aside to stand at room temperature. The reaction products were isolated by partitioning between ether and brine. The aqueous layer was further extracted with ether (4×50mL) and the combined extracts dried with anhydrous sodium sulfate powder. The extract was filtered and evaporated under reduced pressure to leave a dark brown oil. Column chromatography of the brown oil thus obtained using neat ethyl acetate as eluant afforded a yellow oil (2.1 g) which was 5-(4-pyridyl)-4-pentyn-1-ol that slowly solidified and darkened slightly on standing at room temperature Step B: 5-(4-pyridyl)-pentan-1-ol 5-(4-pyridyl)-4-pentyn-1-ol (1.5 g) obtained in the previous step was dissolved in methanol (35 mL) in a Parr hydrogenation bottle and platinum (IV) oxide [Adams' Catalyst] (0.3 g) was added. The Parr bottle was placed on a Parr hydrogenation apparatus and the solution hydrogenated at 40 psi for 5.5 h after which time the starting material had been judged to be consumed by TLC. The spent catalyst was removed by filtration through a Celite pad and the pad carefully washed with more methanol. The combined filtrates were evaporated under reduced pressure on a rotary evaporator and the oily residues then subjected to column chromatography on a short silica column using neat ethyl acetate as the eluant to provide the title compound (1.4 g).

Step C: 5-(4-pyridyl)-pentanal

Oxalyl chloride (2 mL of 2M solution in dry methylene chloride) was placed in a cool oven-dried flask and cooled to −78° C. using a dry ice and acetone cooling bath and a solution of DMSO (632 mg) in dry methylene chloride (1 mL) added drop by drop to the oxalyl chloride over 3 minutes and stirred for a further 3 minutes. A solution of [5-(4-pyridyl)-4-pentan-1-ol (0.6 g) in dry methylene chloride (5 mL) was added to the reaction flask over approx. 3 minutes and the reaction stirred for 15 minutes. Anhydrous triethylamine (2.82 mL) was added and the reaction mixture stirred for another 2 h during which time the cold bath had warmed up to room temperature. The reaction was quenched by the addition of saturated brine and then partitioned with methylene chloride. The aqueous layer was discarded and the methylene chloride extract dried over anhydrous sodium

EXAMPLE 2.2

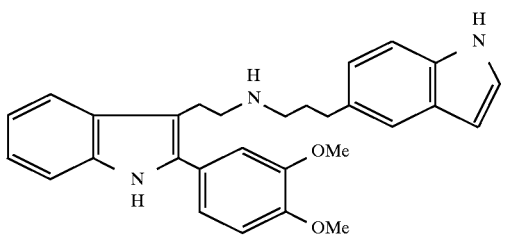

{2- [2-(3,4-dimethoxyphenyl)-1H-indol-3-yl]ethyl}-[3-(1H-indol-5-yl)propyl]amine Step 2.2A N-{2-[2-(3,4-dimethoxyphenyl)-1H-indol-3-yl]ethyl}-3-(1H-indol-5-yl)propionamide To a solution of 3-(1H-indol-5-yl)propionic acid (50 mg in 2.5 mL N,N-dimethylformamide) at 0° C. was added 43 mg 1-hydroxy-benzotriazole followed by 71 mg 1-(3-dimethylaminopropyl)-3-ethylcarbodiimide hydrochloride and the mixture allowed to warm to room temperature. After 23 minutes, 155 mg of 2-[2-(3,4-dimethoxyphenyl)-1H-indol-3-yl]-ethylamine was added and the mixture stirred at room temperature for an additional hour. The reaction was then quenched by the addition of water and the mixture extracted with ethyl acetate. The combined organics were washed with water and brine, dried over sodium sulfate and the concentrated oil purified by flash chromatography on silica gel (methylene chloride:methanol, 95:5) to give the title compound (111 mg).

Step 2.2B {2-[2-(3,4-dimethoxyphenyl)-1H-indol-3-yl]ethyl}-[3-(1H-indol-5-yl)propyl]amine To a solution of N-{2-[2-(3,4-dimethoxyphenyl)-1H-indol-3-yl]ethyl}-3-(1H-indol-5-yl)propionamide (60 mg in 2.0 mL dry tetrahydrofuran) at 0° C. was added 26 mg lithium aluminum hydride and the mixture heated to 77° C. on an oil bath. After 5.5 hours, the mixture was cooled to 0° C. and quenced by the addition of 0.025 mL water and stirred vigorously for 30 minutes at which time the suspension was filtered through a pad of sodium sulfate and the filtrate concentrated in vacuo. Purification by flash chromatography (methylene chloride:methanol, 92:8) gave the title compound (32 mg). m/e=454 (M+H)

Following a procedure similar to that described in EXAMPLES 2.1 and 2.2, the following compounds were prepared:

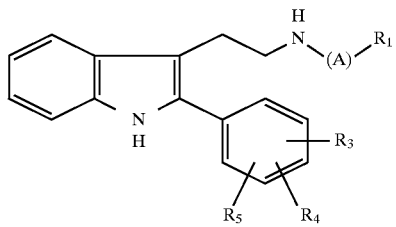

| Example # | R$_1$ | R$_3$, R$_4$, R$_5$ | A = (CH$_2$)$_n$ | m/e |
|---|---|---|---|---|
| 2A | 3-phenyltriazine | 3,4-OMe | 1 | 428 (M + H) |
| 2B | 5-indole | 3,4-OMe | 1 | 426 (M + H) |
| 2C | 5-benzimidazole | 3,4-OMe | 1 | 427 (M + H) |
| 2D | 4-indole | 3,4-OMe | 1 | 426 (M + H) |
| 2E | 3-pyridyl | 3,5-Me | 5 | 412 (M + H) |
| 2F | 4-pyridyl | 3,5-Me | 4 | 398 (M + H) |
| 2G | 2-pyridyl | 3,5-Me | 4 | 398 (M + H) |
| 2H | 3-pyridyl | 3,5-Me | 4 | 398 (M + H) |
| 2I | 5-pyrimidine | 3,5-Me | 4 | 399 (M + H) |
| 2J | (structure) | 3,5-Me | 4 | 453 (M + H) |
| 2K | (structure) | 3,5-Me | 4 | 455 (M + H) |
| 2L | (structure) | 3,5-Me | 4 | 428 (M + H) |
| 2M | (structure) | 3,5-Me | 4 | 415 (M + H) |
| 2N | (structure) | 3,5-Me | 4 | 414 (M + H) |
| 2O | (structure) | 3,5-Me | 4 | 413 (M + H) |
| 2P | (structure) | 3,5-Me | 4 | 491 (M + H) |
| 2Q | 4-pyridyl | 3,5-Me | 2 | 370 (M + H) |
| 2R | 3-pyridyl | 3,5-Me | 2 | 370 (M + H) |
| 2S | 2-pyridyl | 3,5-Me | 2 | 370 (M + H) |
| 2T | 4-imidazolyl | 3,5-Me | 2 | 359 (M + H) |
| 2U | 4-pyridyl | 3,5-Me | 1 | 356 (M + H) |
| 2V | 2-pyridyl | 3,5-Me | 1 | 356 (M + H) |
| 2W | 3-pyridyl | 3,5-Me | 1 | 356 (M + H) |
| 2X | 3-pyridyl | 3,5-Me | 3 | 384 (M + H) |
| 2Y | 4-pyridyl | 3,5-Me | 3 | 384 (M + H) |
| 2Z | 3-quinolinyl | 3,5-Me | 4 | 448 (M + H) |
| 2AA | (structure) | 3,5-Me | 4 | 481 (M + NH$_3$) |

-continued

| Example # | R₁ | R₃, R₄, R₅ | A = (CH₂)ₙ | m/e |
|---|---|---|---|---|
| 2BB | 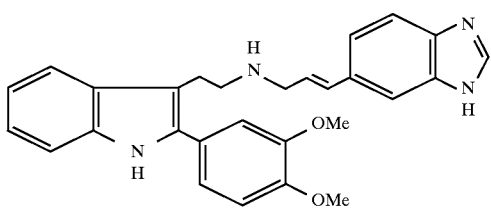 | | 3,5-Me | 4 | — |

EXAMPLE 3

[3-(3H-benzoimidazol-5-yl)-allyl]-{2-[2-(3,4-dimethoxyphenyl)-1H-indol-3-yl]-ethyl}-amine Step 3A {2-[2-(3,4-dimethoxyphenyl)-1H-indol-3-yl]-ethyl}-[3-(1-methanesulfonyl-1H-benzoimidazol-5-yl)-allyl]amine To a solution of 3-(1H-benzoimidazol-5-yl)-prop-2-en-1-ol (44 mg in a mixture of 2 mL methylene chloride and 0.1 mL N,N-dimethylformaminde) at 0° C. was added sequentially 346 mg of tetrabutylammonium bromide, 0.110 mL diisopropylethylamine, and 100 mg methanesulfonic anhydride and the mixture allowed to warm to room temperature. After 1 hour, this mixture was added to a solution of 2-[2-(3,4-dimethoxyphenyl)-1H-indol-3-yl]-ethylamine (300 mg in a mixture of 6 mL methylene chloride and 1.5 mL N,N-dimethylformamide) and stirring continued for 2.5 hours. At this time the mixture was concentrated in vacuo and the residue purified by flash chromatography on silica gel (methylene chloride:methanol, 91:9) to give the title compound (24 mg).

Step 3B [3-(3H-benzoimidazol-5-yl)-allyl]-{2-[2-(3,4-dimethoxyphenyl)-1H-indol-3-yl]-ethyl}-amine To a solution of {2-[2-(3,4-dimethoxyphenyl)-1H-indol-3-yl]-ethyl}-[3-(1-methanesulfonyl-1H-benzoimidazol-5-yl)-allyl]amine (24 mg in 1.5 mL methanol) at 0° C. was added 0.225 niL of a 2N solution of potassium hydroxide and the mixture allowed to warm to room temperature. After 1.5 hours, the reaction was quenched by the addition of 0.30 mL of 1N hydrochloric acid, concentrated in vacuo and purified by flash chromatography on silica gel (methylene chloride:methanol, 88:12) to give the title compound (12 mg). m/e =453 (M+H)

PREPARATION OF SYNTHETIC INTERMEDIATES

Step A 1H-benzoimidazole-5-carboxylic acid N,N-methoxy,methyl amide

To a suspension of 1H-benzoimidazole-5-carboxylic acid (500 mg in 7 mL N,N-dimethylfonnamide) at 0° C. was added 500 mg of 1-hydroxybenzotriazole (HOBt) followed by 828 mg 1-(3-dimethylaminopropyl)-3-ethylcarbodiimide hydrochloride (EDC) and the mixture allowed to warm to room temperature. After 42 minutes, 1.05 g of N,O-dimethylhydroxylamine hydrochloride and 1.5 mL triethylamine were added and stirring continued at room temperature. The reaction was quenched after 1 hour by the addition of water and the product isolated by extraction with ethyl acetate. Purification of the concentrate by flash chromatography on silica gel (methylene chloride:methanol, 90:10) gave the title compound (458 mg).

Step B 1H-benzoimidazole-5-carboxaldehyde

To a solution of 1H-benzoimidazole-5-carboxylic acid N,N-methoxy,methyl amide (458 mg in a mixture of 5 mL diethyl ether and 10 mL tetrahydrofuran) at −78° C. was added 3.7 mL of a 1.5M solution of diisobutylaluminum hydride in toluene and the mixture stirred at low temperature. After 1 hour the reaction mixture was cannulated into a 1M solution of sodium potassium tartrate at 0° C. The resulting slurry was stirred vigorously for 2 hours at room temperature after which time it was extracted with ethyl acetate. The organics were washed with water, dried over sodium sulfate and concentrated in vacuo to provide the crude title compound (250 mg).

Step C 3-(1H-benzoimidazol-5-yl)-acrylic acid methyl ester

To a solution of 1H-benzoimidazole-5-carboxaldehyde (250 mg in 12 mL dry tetrahydrofuran) at 0° C. was added 1.43 g methyl(triphenylphosphoranylidene)acetate and the mixture allowed to warm to room temperature. After 24 hours the mixture was concentrated in vacuo and purified by flash chromatography on silica gel (methylene chloride:methanol, 93:7) to give the title compound (257 mg).

Step D 3-(1H-benzoimidazol-5-yl)-prop-2-en-1-ol

To a solution of 3-(1H-benzoimidazol-5-yl)-acrylic acid methyl ester (50 mg in 1 mL dry tetrahydrofuran) at −78° C. was added 1.24 nL of a 1M solution of lithium tri-sec-butylborohydride in tetrahydrofuran and the mixture stirred at −78° C. for 4 hours followed by warming to −40° C. for an additional 4 hours. The reaction was quenched by addition of aqueous methanol, concentrated in vacuo and purified by flash chromatography on silica gel (methylene chloride:methanol, 87:13) to give the title compound (44 mg).

Following a procedure similar to that described above, the following compound was prepared:

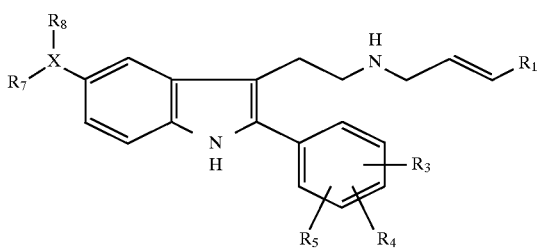

| Example # | X—R₇,R₈ | R₁ | R₃,R₄,R₅ | m/e |
|---|---|---|---|---|
| 3A | H | 5-benzimidazole-N—SO₂Me | 3,4-OMe | — |

EXAMPLE 4.1

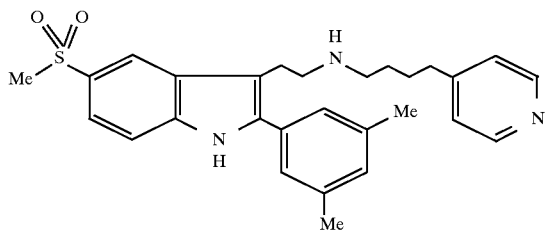

[2-[2-(3,5-dimethylphenyl)-5-methanesulfonyl-1H-indol-3-yl]ethyl]-(4-pyridin-4-yl-butyl)amine Step 4.1A 2-[2-(3,5-dimethylphenyl)-5-methanesulfonyl-1H-indol-3-yl]ethylamine A suspension of 4-(methanesulfonyl)phenylhydrazine (3.0 g, 16.1 mmol) and 3-chloropropyl 3,5-dimethylphenyl ketone (3.4 g, 16.1 mmol) in t-butanol (25 mL) was stirred at room temperature for 20 min and heated briefly on a steam bath. Methanol (250 mL) was added, and the mixture was heated at reflux overnight. After this time, the mixture was concentrated to a small volume, and crystals were filtered off and washed with cold methanol. The combined filtrates were evaporated to a residue, which was partitioned between ethyl ether and water. The ethereal layer was then extracted with water (2x) and the combined aqueous extracts washed with ethyl ether and basicified with 5N sodium hydroxide. The product was extracted with ethyl acetate (3x). The combined organic extracts were washed with water, dried over sodium sulfate, and evaporated to a syrup (3.1 g). The crude material was purified by flash chromatography on silica gel (methylene chloride:methanol, 9:1) to give the title compound (1.99g, 36%), R$_f$0.19 (ninhydrin positive).

Step 4.1 B N-[2-[2-(3,5-dimethylphenyl)-5-methanesulfonyl-1H-indol-3-yl]ethyl]-4-pyridin-4-yl-butyramide A mixture of 2-[2-(3,5-dimethylphenyl)-5-methanesulfonyl-1H-indol-3-yl]ethylamine (1.29 g, 3.77 mmol), 4-(4-pyridyl)butanoic acid (1.37 g, 8.29 mmol), 4-methylmorpholine (1.25 mL, 11.33 mmol), 1-hydroxybenzotriazole (1.53 g, 11.33 mmol), and 1-(3-dimethylaminopropyl)-3-ethylcarbodiimide hydrochloride (1.74 g, 9.08 mmol) in N,N-dimethylformnamide (10 mL) was stirred at room temperature for 14 hours. At this time, the solution was co-distilled with n-butanol (3x) to give a residue, which was purified by flash chormatography on silica gel (methylene chloride:methanol, 97:3) to give the title compound (1.45 g, 79%).

Step 4.1C [2-[2-(3,5-dimethylphenyl)-5-methanesulfonyl-1H-indol-3-yl]ethyl]-(4-pyridin-4-yl-butyl)amine Borane-THF ((1.0M soln in tetrahydrofuran, 27 mL) was added dropwise to a solution of N-[2-[2-(3,5-dimethylphenyl)-5-methanesulfonyl-1H-indol-3-yl]ethyl]-4-pyridin-4-yl-butyramide (1.45 g, 2.96 mmol) in dry tetrahydrofuran (20 mL), and the solution was heated at reflux for 2 hours. At this time, methanol was added to quench excess borane, and the resulting solution was evaporated to dryness. The residue was dissolved in tetrahydrofuran (20 mL), and N,N-dimethylethanolamine (8.9 mL, 88.86 mmol) was added. The solution was heated at reflux for 2.5 hr and then concentrated to dryness. The crude material was purified by flash chromatography on silica gel (methylene chloride:methanol, 95:5) to give the title compound (1.0 g, 71%). m/e=476 (M+H)

Step 4.1D 4[2-[2-(3,5-dimethylphenyl)-5-methanesulfonyl-1H-indol-3-yl]ethyl]-(4-pyridin-4-yl-butyl)amine(dihydrochloride)

Hydrogen chloride in ethyl ether (1.0M, 1.4 mL) was added dropwise to a solution of [2-[2-(3,5-dimethylphenyl)-5-methanesulfonyl-1H-indol-3-yl]ethyl]-(4-pyridin-4-yl-butyl)amine (300 mg, 0.63 mmol) in dry tetrahydrofuran (20 mL) at 0° C. After 10 min, the excess hydrogen chloride and solvents were evaporated to give a solid mass. The product was further dried under high vacuum at 50° C. to give the title compound.

EXAMPLE 4.2

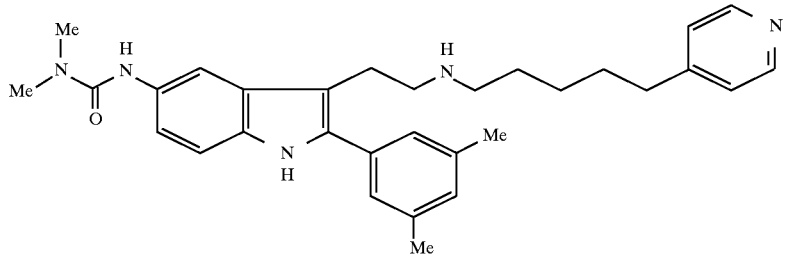

3-[2-(3,5-dimethylphenyl)-3-[2-(5-pyridin-4-yl-pentylamino)-ethyl]-1H-indol-5-yl]-1,1-dimethylurea Step 4.2A 2-[2-(3,5-dimethylphenyl)-5-nitro-1H-indol-3-yl]-ethylamine hydrochloride salt 1-(4-chloro-1-oxo-butyl)-3,5-dimethylbenzene (2.5 g) was dissolved in 12 mL of t-butanol and stirred at room temperature followed by 4-nitrophenylhydrazine (1.65 g). The rection mixture was stirred at room temperature for 20 minutes then water (12 mL) and methanol (108 mL) were added and heated to reflux and maintained at reflux for 17 h. The reaction mixture was cooled to room temperature and the volatile solvents removed at reduced pressure on a rotary evaporator. The residues were evaporated to dryness using an active nitrogen gas flow overnight. The solid dry residues were triturated with ethyl acetate (ca 100 mL) and crystallization initiated by scratching and the sample placed in a refrigerator for 8 h. The solid material thus obtained was collected in a sinter glass funnel under suction and the solid material washed with dry ethyl acetate. A yield of 1.4 g of a solid was obtained.

Step 4.2B {2-[2-(3,5-dimethylphenyl)-5-nitro-1H-indol-3-yl]-ethyl}-carbamic acid tert-butyl ester 2-[2-(3,5-dimethylphenyl)-5-nitro-1H-indol-3-yl]-ethylamine hydrochloride salt (1 g) was suspended in dry methylene chloride (25 mL) and dry triethylamine (0.806 mL) was added and stirred for 5 minutes at room temperature. [2-(tert-butoxycarbonyloxyimino)phenylacetronitrile] (890 mg) was added in small portions over 5 minutes to the tryptamine and the reaction mixture left to stir overnight at room temperature. The reaction was partitioned between methylene chloride and 5% citric acid. The methylene chloride layer was separated and washed with brine and dried over anhydrous sodium sulfate powder. The extract was filtered and evaporated to dryness. The product was isolated by column chromatography using silica gel and an eluant of ethyl acetate and hexanes (35:65 v/v). The yield of the title compound was 1 g.

Step 4.2C {2-[5-amino-2-(3,5-dimethylphenyl)-1H-indol-3-yl]-ethyl}-carbamic acid tert-butyl ester {2-[2-(3,5-dimethylphenyl)-5-nitro-1H-indol-3-yl]-ethyl}-carbamic acid tert-butyl ester (0.4 g) was dissolved in methanol (25 mL) and platinum (IV) oxide (40 mg) added. The mixture was placed on a Parr hydrogenation apparatus and hydrogenated at 45psi for 4 h; by this time the starting material had been consumed and converted into one product. The catalyst was removed by filtration and the filtrates evaporated under reduced pressure using a rotary evaporator and the final traces of solvent removed by using a high vacuum overnight. The amine (338 mg) was obtained as a powder.

Step 4.2D {2-[2-(3,5-dimethylphenyl)-5-(3,3-dimethylureido)-1H-indol-3-yl]-ethyl}-carbamic acid tert-butyl ester Finely divided {2-[5-amino-2-(3,5-dimethylphenyl)-1H-indol-3-yl]-ethyl}-carbamic acid tert-butyl ester (265 mg) was suspended in dry tetrahydrofuran (5mL) and diisopropylethylamine (0.146 mL) and dimethylcarbamoyl chloride (0.077 mL) were added. The reaction mixture was stirred at room temperature for 2.5 days. The reaction mixture was concentrated on a rotary evaporator and the residues were applied to four (20×20 cm 1000μ) preparative silica gel plates and eluted with a solvent system comprising methanol and methylene chloride in the ratio (1:9 v/v). The product (299 mg) was isolated as a thick gum that solidified on prolonged standing.

Step 4.2E 3-[3-(2-aminoethyl)-2-(3,5-dimethylphenyl)-1H-indol-5-yl]-1,1-dimethylurea {2-[2-(3,5-dimethylphenyl)-5-(3,3-dimethylureido)-1H-indol-3-yl]-ethyl}-carbamic acid tert-butyl ester (295 mg) was dissolved in a ternary solvent mixture comprising methylene chloride (6 mL), trifluoroacetic acid (2 mL) and anisole (2 mL) for 2.5 h. The volatile solvent components were removed on a rotary evaporator and the residues taken up in methanol and purified on four (20×20 cm 1000μ) preparative silica gel plates and eluted with a solvent system comprising methanol and methylene chloride in the ratio (1:9 v/v). The product (222 mg) was isolated as a foamy material.

Step 4.2F 3-[2-(3,5-dimethylphenyl)-3-[2-(5-pyridin-4-yl-pentylamino)-ethyl]-1H-indol-5-yl]-1,-dimethylurea 3-[3-(2-aminoethyl)-2-(3,5-dimethylphenyl)-1H-indol-5-yl]-1,1-dimethylurea (25 mg) from the previous step was dissolved in tetrahydrofuran (1 mL) and deuterochloroform (1 mL) at approx 0° C. and 5-(4-pyridyl)pentanal (10.6 mg) was added. The reaction mixture was maintained at this temperature for 15 minutes and then finely divided sodium borohydride powder was added followed by anhydrous methanol. The reaction mixture was stirred at approx. 0° C. for 15 minutes and then quenched by addition of 20 drops of 2N hydrochloric acid and water (1 mL). The volatiles were removed on a rotary evaporator and the water using an active flow of nitrogen gas. The residues were placed on four (20×20 cm 500μ) preparative silica gel plates and eluted with a solvent system comprising methanol and methylene chloride in the ratio (1:9 v/v). The product (14.2 mg) was isolated as a thick oil.

Following a procedure similar to that described in EXAMPLES 4.1 and 4.2, the following compounds were prepared:

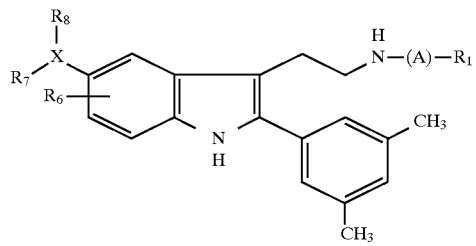

| Example # | X—R$_7$, R$_8$ | A = (CH$_2$)n | R$_1$ | m/e |
|---|---|---|---|---|
| 4A | * | 4 | 4-pyridyl | 443 (M + H) |
| 4B | Br | ** | 4-pyridyl | 476 (M + H) |
| 4C | —NH$_2$ | 4 | 4-pyridyl | 413 (M + H) |
| 4D | —NH—COCH$_3$ | 4 | 4-pyridyl | 455 (M + H) |
| 4E | —NH—CO—N(CH$_2$CH$_3$)$_2$ | 4 | 4-pyridyl | 512 (M + H) |
| 4F | —NH—CO—N(CH$_2$CH$_3$)$_2$ | 4 | 3-pyridyl | 512 (M + H) |
| 4G | —NH—CO—N(CH$_2$CH$_3$)$_2$ | 4 | 6-methoxy-3-pyridyl | 542 (M + H) |
| 4H | —NH—CO—N(CH$_3$)$_2$ | 5 | 3-pyridyl | 498 (M + H) |
| 4I | —NH—CO—N(CH$_2$CH$_3$)$_2$ | 5 | 3-pyridyl | 526 (M + H) |
| 4J | —NH—CO—N(CH$_2$CH$_3$)$_2$ | 5 | 4-pyridyl | 526 (M + H) |
| 4K | —NH—CO—N(CH$_3$)$_2$ | 4 | 6-methoxy-3-pyridyl | 514 (M + H) |
| 4L | —SO$_2$—CH$_2$—CO—Me | 4 | 4-pyridyl | 518 (M + H) |
| 4M | Me-CH(OH)-CH$_2$-S(O)$_2$- | 4 | 4-pyridyl | 520 (M + H) |

-continued

| Example # | X—R$_7$, R$_8$ | A = (CH$_2$)n | R$_1$ | m/e |
|---|---|---|---|---|
| 4N | Me-CH=CH-SO$_2$- | 4 | 4-pyridyl | 502 (M + H) |
| 4O | Me-CH$_2$-CH$_2$-SO$_2$- | 4 | 4-pyridyl | 504 (M + H) |
| 4P | MeSO$_2$— | 4 | 3-pyridyl | 518 (M + H) |
| 4Q | MeSO$_2$— | 4 | 6-methoxy-3-pyridyl | 506 (M + H) |
| 4R | MeSO$_2$— | 4 | 4-methyl-2-oxo-1H-pyridyl (NH, O) | 492 (M + H) |
| 4S | MeSO$_2$— | 5 | 4-pyridyl | 490 (M + H) |
| 4T | MeSO$_2$— | 5 | 3-pyridyl | 490 (M + H) |
| 4U | Me$_2$N(Et)-C(O)-CH$_2$-SO$_2$- | 4 | 4-pyridyl | 575 (M + H) |

(*)—R$_6$ = 5-NO$_2$
(**)—R$_6$ = Br

EXAMPLE 5.1

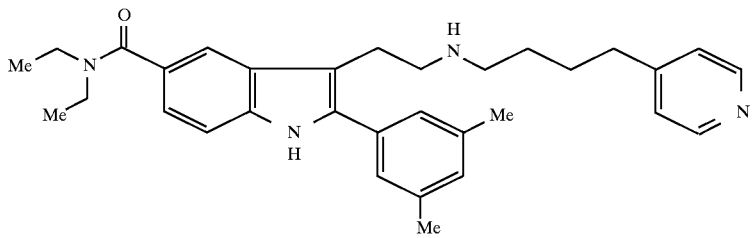

2-(3,5-dimethylphenyl)-3-[2-[4-(pyridin-4-yl)butylamino]ethyl]-1H-indole-5-carboxylic acid diethylamide dihydrochloride Step 5.1A 3-(2-aminoethyl)-2-(3,5-dimethylphenyl)-1H-indole-5-carboxylic acid ethyl ester A mixture of 7.60 g (50 mmol) of 4-hydrazinobenzoic acid, 10.55 g (50 mmol) of 3-chloropropyl 3,5-dimethylphenyl ketone, and 200 mL of absolute ethanol was stirred under nitrogen and heated to reflux. After 12 hours, the mixture was cooled and filtered. The solid on the filter was washed with additional small volumes of ethanol. The filtrate was treated with 4 mL of concentrated sulfuric acid and stirred at reflux under nitrogen for 4 days. The cooled mixture was stirred in an ice bath as a solution of sodium ethoxide (21% w/w in ethanol) was added dropwise until the mixture was basic by pH paper. The mixture was filtered and concentrated in vacuo at 30° C. The residue was partitioned between diethyl ether and water, with some saturated aqueous sodium chloride solution added to assist in separation of the layers. The aqueous phase was washed with an additional 100 mL of ether. The combined organic extracts were dried over sodium sulfate, filtered, and concentrated in vacuo. The residual gum was purified by flash chromatography on silica gel (elution with 97:3:0.3 and then 95:5:0.5 methylene chloride:methanol:-ammonium hydroxide) to give the title compound (4.8g). 400 MHz $^1$H NMR (CDCl$_3$) was consistent with the assigned structure. Mass spectrum (PB-NH$_3$/CI): m/e=337 (M+H).

Step 5.1B 2-(3,5-dimethylphenyl)-3-[2-[4-(pyridin-4-yl)butylamino]-ethyl]-1H-indole-5-carboxylic acid ethyl ester To a dry flask were added 5.0 g (14.9 mmol) of 3-(2-aminoethyl)-2-(3,5-dimethylphenyl)-1H-indole-5-carboxylic acid ethyl ester, 1.98 g (13.5 mmol) of 4-(pyridin-4-yl)butyraldehyde (prepared essentially as described in Example 2.1; diluted with 0.5 mL of CDCl$_3$), 8.12 g (67.7 mmol) of anhydrous magnesium sulfate, and a magnetic stirring bar. The flask was purged with nitrogen, cooled to −10° C., and stirred as 11.5 mL of dry CDCl$_3$ was introduced gradually by syringe. The mixture was stirred under nitrogen for about 20 minutes. Next, the septum was removed, and 670 mg (17.6 mmol) of sodium borohydride was added rapidly. The septum was immediately replaced, and the system was again purged with nitrogen. The mixture was stirred under nitrogen at about −5° C. as 10 mL of dry methanol was added gradually by syringe. After a few minutes at this temperature, the reaction was removed from the cooling bath and partitioned between 80 mL of ethyl acetate and 100 mL of water. The organic layer was dried over sodium sulfate, filtered, and concentrated in vacuo. The residue was purified by flash chromatography on silica gel (elution with a gradient of 4–9% methanol in methylene chloride; repeated using 5–15% methanol in methylene chloride) to give the title compound (3.19 g). 500 MHz ¹H NMR (CDCl₃) was consistent with the assigned structure. Mass spectrum (PB-NH₃/CI): m/e=470.4 (M+H). An additional 1.91 g of less pure material was also isolated.

Step 5.1C 3-[2-[benzyloxycarbonyl-[4-(pyridin-4-yl)butyl]amino]ethyl]-2-(3,5-dimethylphenyl)-1H-indole-5-carboxylic acid ethyl ester A solution of 3.19 g (6.83 mmol) of 2-(3,5-dimethylphenyl)- 3-[2-[4-(pyridin-4-yl)butylamino] ethyl]-1H-indole-5-carboxylic acid ethyl ester in 25 mL of dry methylene chloride was stirred under nitrogen and cooled to –78° C. in a dry ice-acetone bath as 2.38 mL (1.76 g, 13.7 mmol) of N,N-diisopropylethylamine was added, followed by gradual addition of 3.4 mL (4.06 g; 23.7 mmol) of benzyl chloroformate by syringe, in portions. After about 2.5 hours, the solution was removed from the cooling bath and allowed to warm to room temperature. It was then partitioned between ethyl acetate and 5% potassium bisulfate aqueous solution. The organic phase was dried over magnesium sulfate, filtered, and concentrated in vacuo. Purification of the residue by flash chromatography on silica gel (elution with a gradient of 0.5–10% methanol in methylene chloride) afforded a quantitative yield of the product as a yellow foam. 500 MHz ¹H NMR was complex, owing to the existence of rotamers, but was consistent with the assigned structure. Mass spectrum (PB-NH₃/CI): m/e=604.3 (M+H).

Step 5.1D 3-[2-[benzyloxycarbonyl-[4-(pyridin-4-yl)butyl]amino]-ethyl]-2-(3,5-dimethylphenyl)-1H-indole-5-carboxylic acid hydrochloride A solution of 4.11 g (6.83 mmol) of 3-[2-[benzyloxycarbonyl-[4-(pyridin-4-yl)butyl]amino]ethyl]-2-(3,5-dimethylphenyl)-1H-indole-5-carboxylic acid ethyl ester in 161 mL (80.5 mmol) of 0.50N potassium hydroxide in methanol was stirred at about 60° C. as 19 mL of water was added gradually. Stirring was continued at reflux overnight. The cooled mixture was concentrated in vacuo to give a yellow solid, which was partitioned between 250 mL of a 1:1 ethyl acetate-tetrahydrofuran mixture and 250 mL of 0.5N hydrochloric acid. The organic phase was washed twice with 0.5N hydrochloric acid, then dried over magnesium sulfate, filtered, and concentrated in vacuo. The resulting solid was triturated with diethyl ether and collected on a filter to give (after drying) 3.46 g of yellow solid, mp 133.5°–137.5° C.; homogeneous by TLC (95:5:0.5 CH₂Cl₂-MeOH-AcOH). 500 MHz ¹H NMR (DMSO-d₆) was consistent with the assigned structure. Mass spectrum (ESI): m/e=576.4 (M+H).

Step 5.1E [2-[5-diethylcarbamoyl-2-(3,5-dimethylphenyl)-1H-indol-3-yl]ethyl]-[4-(pyridin-4-yl)butyl]carbamic acid benzyl ester A mixture of 846 mg (1.38 mmol) of 3-[2-[benzyloxycarbonyl-[4-(pyridin-4-yl)butyl]amino]ethyl]-2-(3,5-dirnethylphenyl)-1H-indole-5-carboxylic acid hydrochloride, 862 mg (1.66 mmol) of benzotriazol-1-yloxy-tris(pyrrolidino)phosphonium hexafluorophosphate (PyBOP), and 8.5 mL of dry methylene chloride was treated with 1.16 mL (839 mg; 8.29 mmol) of triethylamine, followed after a few minutes by 0.715 mL (505 mg, 6.91 mmol) of diethylamine. The resulting solution was stirred under nitrogen at room temperature overnight and then partitioned between ethyl acetate and saturated aqueous sodium bicarbonate solution. The organic layer was dried over sodium sulfate, filtered, and concentrated in vacuo. Purification of the residue by flash chromatography on silica gel (gradient elution with 1–5% methanol in methylene chloride) afforded a quantitative yield of the desired product; homogeneous by TLC in 95:5 CH₂Cl₂-MeOH. 500 MHz ¹H NMR (CDCl₃) was complex, owing to rotamers, but was consistent with the assigned structure. Mass spectrum (ESI): m/e=631.5 (M+H).

Step 5.1F 2-(3,5-dimethylphenyl)-3-[2-[4-(pyridin-4-yl)butylamino]-ethyl]-1H-indole-5-carboxylic acid diethylamide A mixture of 871 mg (1.38 mmol) of [2-[5-diethylcarbamoyl-2-(3,5-dimethylphenyl)-1H-indol-3-yl]ethyl]-[4-(pyridin-4-yl)butyl]carbamic acid benzyl ester, 300 mg of 20% palladium hydroxide on carbon, and 40 mL of 2-methoxyethanol was shaken with hydrogen (approx. 45 psig) in a pressure vessel for 2.3 hours. The catalyst was removed by filtration through diatomaceous earth, and the filtrate was concentrated in vacuo. The residue was purified by flash chromatography on silica gel (elution with a gradient from 99:1:0.1 to 93:7:0.7 CH₂Cl₂-MeOH-concd. NH₄OH) to give 454 mg (66%) of yellow foam; homogeneous by TLC in 95:5:0.5 CH₂Cl₂-MeOH-concentrated NH₄OH. 500 MHz 1H NMR (CDl₃) was consistent with the assigred structure. Mass spectrum (ESI): m/e=497.5 (M+H).

Step 5.1G 2-(3,5-dimethylphenyl)-3-[2-[4-(pyridin-4-yl)butylamino]-ethyl]-1H-indole-5-carboxylic acid diethylamide dihydrochloride A solution of 452 mg (0.914 mmol) of 2-(3,5-dimethylphenyl)-3-[2-[4-(pyridin-4-yl)butylamino]ethyl]-1H-indole-5-carboxylic acid diethylamide in 45 mL of methanol was treated with 1.83 mL (3.66 mmol) of 2N hydrochloric acid. After a few minutes, the solution was evaporated to dryness. The residue was reconcentrated from methanol and then triturated with diethyl ether. The solid was collected on a filter, washed with additional diethyl ether, and dried to give 455 mg (87%) of yellowish powder, mp 154°–157° C. 500 MHz ¹H NMR (DMSO-d₆) was consistent with the assigned structure.

EXAMPLE 5.2

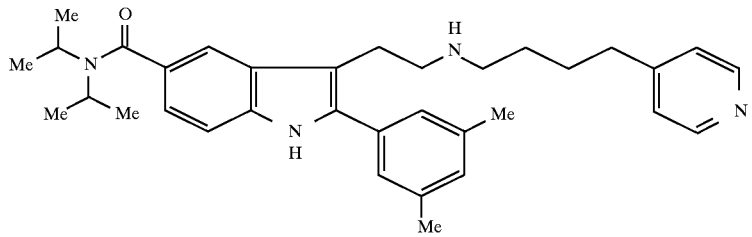

Following a procedure similar to that described in Example 5, the following compounds were prepared:

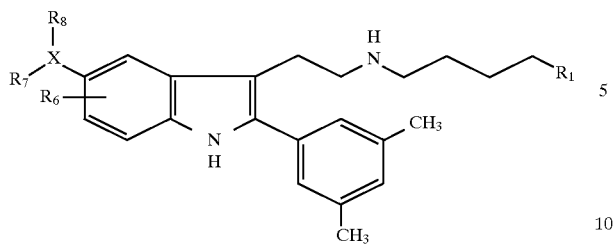
| Example # | X—R7, R8 | R6 | R1 | m/e |
|---|---|---|---|---|
| 5A | MeO-C(O)- (ethyl ester -OCH2CH3, acetate) | H | 4-pyridyl | 470 (M + H) |
| 5B | MeO-C(O)- (ethyl ester) | H | 3-pyridyl | 470 (M + H) |
| 5C | Me2N-C(O)- | H | 3-pyridyl | 469 (M + H) |
| 5D | Me2N-C(O)- | H | 4-pyridyl | 469 (M + H) |
| 5E | Et2N-C(O)- | H | 3-pyridyl | 497 (M + H) |
| 5F | (F3CCH2)2N-C(O)- | H | 4-pyridyl | 605 (M + H) |
| 5G | HOCH2CH2(Et)N-C(O)- | H | 3-pyridyl | 513 (M + H) |
| 5H | HOCH2CH2(Et)N-C(O)- | H | 4-pyridyl | 513 (M + H) |
| 5I | MeOCH2CH2(n-Pr)N-C(O)- | H | 3-pyridyl | 557 (M + H) |

-continued
| Example # | X—R₇, R₈ | R₆ | R₁ | m/e |
|---|---|---|---|---|
| 5J |  | H | 3-pyridyl | 557 (M + H) |
| 5K | 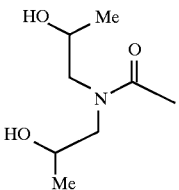 | H | 3-pyridyl | 551 (M + H) |
| 5L | 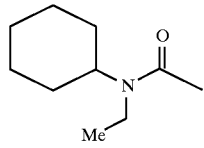 | H | 4-pyridyl | 551 (M + H) |
| 5M | 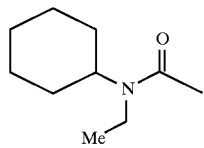 | H | 4-pyridyl | 551 (M + H) |
| 5N | 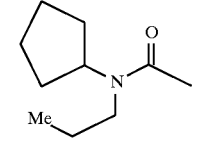 | H | 3-pyridyl | 553 (M + H) |
| 5O | 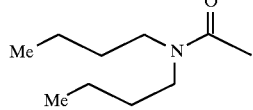 | H | 4-pyridyl | 553 (M + H) |
| 5P | 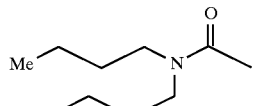 | H | 3-pyridyl | 483 (M + H) |
| 5Q | 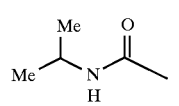 | H | 4-pyridyl | 525 (M + H) |
| 5R | 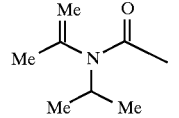 | H | 3-pyridyl | 511 (M + H) |
| 5S | 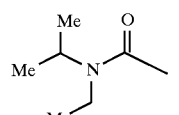 | H | 3-pyridyl | 559 (M + H) |
| 5T | 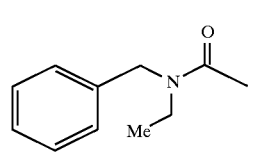 | H | 4-pyridyl | 559 (M + H) |

-continued

| Example # | X—R₇, R₈ | R₆ | R₁ | m/e |
|---|---|---|---|---|
| 5U | Me-N(propyl)(CH₂-cyclopropyl)C(O) | H | 3-pyridyl | 537 (M + H) |
| 5V | —CON(Et)₂ | H | 2,5-dimethylphenyl-benzisoxazole | 551 (M + H) |
| 5W | —COOMe | 6-Cl | 4-pyridyl | 490 (M + H) |
| 5X | —CON(iBu)₂ | 6-Cl | 4-pyridyl | 587 (M + H) |
| 5Y | —CON(Et)₂ | H | 5-methyl-1-(p-tolylsulfonyl)indol-3-yl | 689 (M + H) |
| 5Z | —CON(CH₂CH₂CN)—cyclohexyl | H | 4-pyridyl | 576 (M + H) |
| 5AA | cyclooctyl-N(Me)C(O) | H | 4-pyridyl | 565 (M + H) |
| 5BB | —COOMe | 4-Cl | 4-pyridyl | 490 (M + H) |
| 5CC | —CON(iBu)₂ | 4-Cl | 4-pyridyl | 587 (M + H) |
| 5DD | —CON(Et)₂ | 6-Cl | 4-pyridyl | 531 (M + H) |

EXAMPLE 6

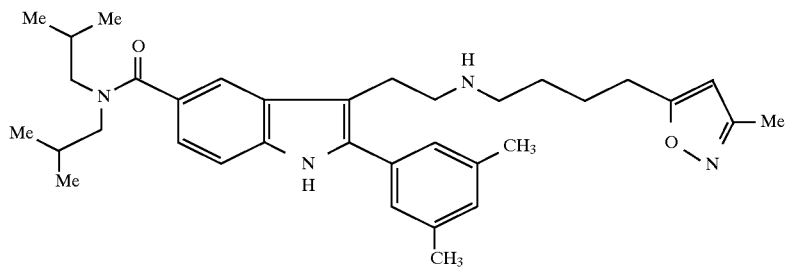

2-(3,5-dimethylphenyl)-3-{2-[4-(3-methylisoxazol-5-yl) butylamino]-ethyl-}-1H-indole-5-carboxylic acid diisobutylamide To a solution of 3-(2-aminoethyl)-2-(3,5-dimethylphenyl)-1H-indole-5-carboxylic acid diisobutylamide (prepared essentially as described in Example 5.1, 83 mg in 2.5 mL dry CDCl$_3$) at 0° C. was added 240 mg magnesium sulfate followed by 30.6 mg 4-(3-methylisoxazol-5-yl)-butyraldehyde and the mixture stirred at low temperature. After 15 minutes, a cold solution of sodium borohydride (30.2 mg in 1.5 mL dry methanol) was added and the mixture stirred for an additional 15 minutes. At this time the reaction was quenched by the addition of water, extracted with ethyl acetate then methylene chloride and the combined organics dried over sodium sulfate. Purification of the concentrate by preparative TLC on silica gel (methylene chloride:methanol, 9:1) gave the title compound (28 mg). m/e=557 (M+H)

PREPARATION OF SYNTHETIC INTERMEDIATES 4-(3-methylisoxazol-5-yl)-butyraldehyde Step A tert-butylhex-5-ynyloxydimethylsilane To a solution of hex-5-yn-1-ol (1.96 g in 40 mL dry methylene chloride) at 0° C. was added 3.48 mL triethylamine followed by 3.31 g tert-butyldimethylsilyl chloride and the mixture stirred while slowly warming to room temperature. After 60 hours, the mixture was filtered to remove solids and the filtrate concentrated in vacuo. Purification by flash chromatography on silica gel (ethyl acetate:hexane, 1:9, then 1:3) gave the title compound (1.62 g).

Step B 5-[4-(tert-butyldimethylsilanyloxy)butyl]-3-methylisoxazole

To a solution of tert-butylhex-5-ynyloxydimethylsilane (1.0 g in 20 mL dry toluene) was added, 530 mg nitroethane followed by 1.31 mL triethylamine and 1.1 g 4-chlorophenyl isocyanate and the mixture stirred at room temperature. After 1 hour, the contents were heated to reflux on an oil bath for an additional 20 hours then cooled to room temperature and filtered to remove solids. Concentration of the filtrate in vacuo and purification by flash chromatography on silica gel (ethyl acetate:hexane, 1:9, then 1:2) gave the title compound (388 mg).

Step C 4-(3-methylisoxazol-5-yl)-butan-1-ol

To a solution of 5-[4-(tert-butyldirnethylsilanyloxy) butyl]-3-methylisoxazole (350 mg in 5 mL dry tetrahydrofuran) at 0° C. was added 1.62 mL of a 1M solution of tetrabutylammonium fluoride in tetrahydrofuran and the mixture stirred while warming to room temperature. After 16 hours, the mixture was concentrated in vacuo and the residue purified by flash chromatography on silica gel (ethyl acetate:hexane, 1:3, then 1:1) to give the title compound (147 mg).

Step D 4-(3-methylisoxazol-5-yl)-butyraldehyde

To a solution of oxalyl chloride (0.40 mL of a 2M solution in methylene chloride in 2 mL dry methylene chloride) at −78° C. was added a solution of methyl sulfoxide (126 mg in 1 mL methylene chloride) and the mixture stirred at low temperature for 3 minutes. A solution of 4-(3-methylisoxazol-5-yl)-butan-1-ol (100 mg in 1 mL methylene chloride) was added and the reaction allowed to proceed for 15 minutes after which time 0.67 mL triethylamine were added and the mixture allowed to warm to room temperature. After 30 minutes brine was added and the mixture extracted with methylene chloride. The organic portion was dried over sodium sulfate and concentrated in vacuo. Purification of the residue by flash chromatography on silica gel (ethyl acetate:hexane, 1:1) gave the title compound (48 mg).

Following a procedure similar to that described in Example 6, the following compounds were prepared:

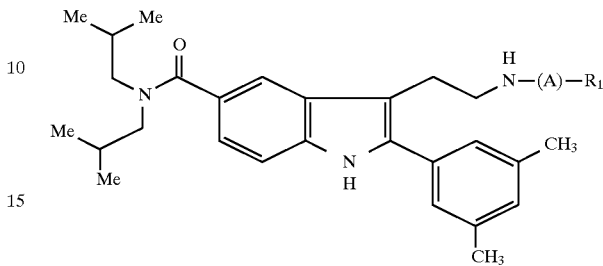

| Example # | A = (CH$_2$)n | R$_1$ | m/e |
|---|---|---|---|
| 6A | 4 | 4-pyridyl | 553 (M + H) |
| 6B | 4 | 3-pyridyl | 553 (M + H) |
| 6C | 4 | 6-amino-3-pyridyl | 568 (M + H) |
| 6D | 4 | 6-amino-3-pyridyl | 583 (M + H) |
| 6E | 4 | 6-methoxy-3-pyridyl | 583 (M + H) |
| 6F | 4 | (3-Et-isoxazol-5-yl) | 571 (M + H) |
| 6G | 4 | (3-Pr-isoxazol-5-yl) | 585 (M + H) |
| 6H | 4 | (3-CO$_2$H-isoxazol-5-yl) | 587 (M + H) |
| 6I | 4 | (3-CO$_2$Et-isoxazol-5-yl) | 615 (M + H) |
| 6J | 4 | (3-CONEt$_2$-isoxazol-5-yl) | 642 (M + H) |
| 6K | 4 | 2-cyano-4-pyridyl | 578 (M + H) |
| 6L | 4 | (2-oxo-1,2-dihydropyridyl) | 569 (M + H) |
| 6M | 4 | (4-COOEt-3-Me-isoxazol-5-yl) | 629 (M + H) |
| 6N | 4 | 2-(CH$_2$NH—Boc)-4-pyridyl | — |
| 6O | 4 | 2-(CH$_2$NH$_2$)-4-pyridyl | 582 (M + H) |
| 6P | 4 | 6-(SMe)-3-pyridyl | 599 (M + H) |
| 6Q | 4 | 5-carboethoxy-3-pyridyl | 625 (M + H) |

53
-continued

| Example # | A = $(CH_2)n$ | $R_1$ | m/e |
|---|---|---|---|
| 6R | 4 | 6-(NHCOOEt)-3-pyridyl | — |
| 6S | 4 | 2,3,5,6-tetrafluoro-4-pyridyl | 625 (M + H) |
| 6T | 3 | 3-pyridyl | — |
| 6U | 4 | 6-[NHS(O)₂CF₃]-3-pyridyl | — |
| 6V | 4 | 6-[NHS(O)₂CH₃]-3-pyridyl | 646 (M + H) |
| 6W | 4 | 5-cyano-3-pyridyl | — |
| 6X | 4 | (structure shown) | — |
| 6Y | 4 | 3,5-dichloro-4-pyridyl | 621 (M + H) |
| 6Z | 4 | (quinoline structure shown) | 638 (M + H) |

EXAMPLE 7.1

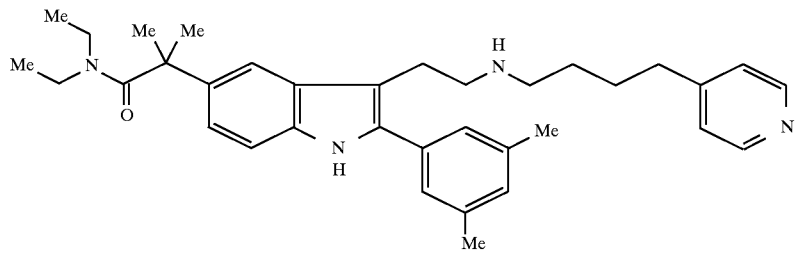

2-[2-(3,5-dimethylphenyl)-3-[2-[4-(pyridin-4-yl)butylaminoethyl]-1-H-indol-5-yl]-N,N-diethylisobutyramide Step 7.1 A 2-[3-(2-aminoethyl)-2-(3,5-dimethylphienyl)-1H-indol-5-yl]-N,N-diethylisobutyramide A solution of 4.85 g (23 mmol) of 3-chloropropyl 3,5-dimethylphenyl ketone and 6.87 g (27.6 mmol) of N,N-diethyl-2-(4-hydrazinophenyl)isobutyramide in 92 mL of absolute ethanol was stirred at reflux under nitrogen for 43 hours. The solution was then cooled and concentrated in vacuo. Purification of the residue by flash chromatography on silica gel (gradient elution with 0–5% methanol in methylene chloride followed by 95:5:0.5 methylene chloride-methanol-ammonium hydroxide and 92.5:7.5:0.75 methylene chloride-methanol-ammonium hydroxide) gave 873 mg (9.4%) of brick red, stiff foam; satisfactory purity by TLC in 95:5:0.5 $CH_2Cl_2$-MeOH-concd. $NH_4OH$. 500 MHz $^1H$ NMR ($CDCl_3$) was consistent with the assigned structure. Mass spectrum (PB-$NH_3$/CI): m/e=406 (M+H).

Step 7.1B 2-[2-(3,5-dimethylphenyl)-3-[2-[4-(pyridin-4-yl)butylamino]ethyl]-1H-indol-5-yl]-N,N-diethylisobutyramide A mixture of 93.3 mg (0.23 mmol) of 2-[3-(2-aminoethyl)-2-(3,5-dimethylphenyl)-1H-indol-5-yl]-N,N-diethylisobutyramide, 37.7 mg (0.253 mmol) of 4-(pyridin-4-yl)butyraldehyde, and 138 mg (1.15 mmol) of magnesium sulfate was purged with nitrogen and cooled in an ice-methanol bath at about −10° C. as 0.50 mL of $CDCl_3$ was added gradually by syringe. The mixture was stirred under nitrogen at this temperature for 1 hour. The septum was removed just long enough to add 11.3 mg (0.30 mmol) of sodium borohydride, and the solution was repurged with nitrogen. The mixture was stirred at −10° to −5° C. as 0.50 mL of dry methanol was added gradually, and stirring was continued at this temperature. After 35 minutes, the mixture was partitioned between 5 mL of ethyl acetate and 5 mL of water. The ethyl acetate layer was washed with brine, then dried over sodium sulfate, filtered, and concentrated in vacuo. The residue was purified by two stages of preparative TLC on Analtech tapered silica gel GF plates (developed first in 90:10:1 methylene chloride -methanol-ammonium hydroxide and repeated in 90:10 methylene chloride-methanol). Isolation of the product bands gave 25.7 mg (21%) of light golden-colored glassy residue; virtually homogenous by TLC in 92.5:7.5:0.75 $CH_2Cl_2$-MeOH-concd. $NH_4OH$. 500 MHz $^1H$ NMR ($CDCl_3$) was consistent with the assigned structure. Mass spectrum (ESI): m/e=539 (M+H).

PREPARATION OF SYNTHETIC INTERMEDIATES

Step A 4-chloro-N-methoxy-N-methylbutyramide

To a solution of 4-chlorobutyryl chloride (10.0 g in 200 mL of dry methylene chloride) was added 10.4 g of N,O-dimethylhydroxylanmine hydrochloride. The mixture was stirred under nitrogen and maintained below 25° C. by cooling in an ice bath as necessary while triethylamine (29.1 mL) was added dropwise over about 20 minutes, resulting in precipitation. After 1.5 hours at room temperature, the mixture was concentrated in vacuo. The residue was partitioned between 100 mL of diethyl ether and 100 mL of saturated aqueous sodium bicarbonate solution. The organic layer was washed with an additional 100 mL of saturated sodium bicarbonate, and the aqueous fractions were back-extracted with ether. The combined organic phases were dried over sodium sulfate, filtered, and concentrated in vacuo to give 10.5 g (90%) of an oil, which had satisfactory purity by $^1H$ NMR ($CDCl_3$). Mass spectrum (PB-$NH_3$/CI): m/e=166 (M+H).

Step B 3-chloropropyl 3,5-dimethylphenyl ketone

A solution of 10.2 mL (13.9 g; 72 mmol) of 5-bromo-m-xylene in 200 mL of anhydrous tetrahydrofuran was stirred under nitrogen at −78° C. as 35.8 mL (84 mmol) of 2.5M n-butyllithium in tetrahydrofuran was added dropwise. After 15 minutes at −78° C., a solution of 10.0 g (60 mmol) of 4-chloro-N-methoxy-N-methylbutyramide in 30 mL of anhydrous tetrahydrofuran was added dropwise over 25–30 minutes. The resulting solution was maintained at −78° C. for 45 minutes and then warmed briefly to room temperature. The reaction was quenched by addition of 40 mL of 2N hydrochloric acid and then partitioned between ethyl acetate and water. The organic phase was washed with saturated aqueous sodium bicarbonate solution and then saturated aqueous sodium chloride solution. The organic solution was dried over sodium sulfate, filtered, and concentrated in vacuo. Flash chromatography of the residue afforded 8.91 g (70%) of an oil, which had satisfactory purity by $^1$H NMR (CDCl$_3$).

Step AA Ethyl 2-(4-hydrazinophenyl)acetate hydrochloride and 2-(4-hydrazinophenylacetic acid hydrochloride This compound (a mixture of the ethyl ester and the carboxylic acid) was prepared from 13.4 g (75 mmol) of ethyl 2-(4-aminophenyl)acetate, by diazotization and stannous chloride reduction of the diazonium salt, according to the method of L. J. Street, et al., *J. Med. Chem.*, 36, 1529 (1993). The material was obtained in two crops. The first crop consisted of 6.40 g of powder, mp >200° C. By 400 MHz $^1$H NMR (DMSO-d$_6$), this material consisted of a mixture of carboxylic acid and ethyl ester in approximately a 4:3 molar ratio. Mass spectrum (PB-NH$_3$/CI): 195 (arylhydrazonium cation for the ethyl ester). The second crop consisted of 4.60 g of powder, mp >180° C. By 400 MHz $^1$H NMR (DMSO-d$_6$), this material consisted of a mixture of carboxylic acid and ethyl ester in approximately a 7:1 molar ratio. After adjustment for the mixture composition of the two crops, the estimated total yield was 69%. Because esterification of any carboxylic acid occurs in the next step, both the ester and the acid react to give the same product.

Step AAA (+/−)-2-(4-Nitrophenyl)propionic acid ethyl ester

To a solution of 9.76 g (50 mmol) of (+/−)-2-(4-nitrophenyl)propionic acid in 150 mL of absolute ethanol was added 3.0 mL of concentrated sulfuric acid. The resulting solution was stirred at reflux under nitrogen. After 6 hours, the solution was cooled and stirred vigorously as 250 mL of saturated aqueous sodium bicarbonate solution was added gradually (Caution: foaming). The mixture was then partitioned between 750 mL of ethyl acetate and 500 mL of water. The organic layer was washed with 100 mL of saturated aqueous sodium bicarbonate solution and then with 100 mL of saturated aqueous sodium chloride solution. The organic phase was dried over magnesium sulfate, filtered, and concentrated in vacuo to give 10.86 g (97%) of an oil; homogeneous by TLC in 9:1 hexane-EtOAc. 400 MHz $^1$H NMR (CDCl3) was consistent with the assigned structure.

Step BBB 2-methyl-2-(4-nitrophenyl)propionic acid ethyl ester

A suspension of 924 (23 mmol) of sodium hydride (60% in oil) in 21 mL of dry N,N-dimethylformamide was stirred under nitrogen in an ice bath as a solution of 4.68 g (21 mmol) of (+/−)-2-(4-nitrophenyl)propionic acid ethyl ester in 20.5 nL of dry N,N-dimethylformamide was added gradually over about 10 minutes. An intense violet color developed during the addition. The mixture was then allowed to warm to room temperature. After about 1 hour, the mixture was again cooled in an ice bath as a solution of 1.44 mL (3.28 g; 23 mmol) of methyl iodide in 5 mL of dry N,N-dimethylformamide was added dropwise by syringe over about 10 minutes, while maintaining the internal temperature at 10°–15° C. The mixture was allowed to warm to room temperature, and the color changed to brown. After 1 hour, an additional 187 mL (426 mg, 3 mmol) of methyl iodide was added. By the next day, the mixture consisted of a suspension of some grayish solid in a golden liquid. It was stirred vigorously and quenched by gradual addition of 10 mL of 5% aqueous potassium bisulfate solution. The mixture was partitioned between 400 mL of diethyl ether and 400 mL of water. The organic layer was washed with an additonal 3×400 mL of water and then with 50 mL of saturated aqueous sodium chloride solution. The organic phase was then dried over magnesium sulfate, filtered, and concentrated in vacuo. Flash chromatography of the residue on silica gel (elution with 19:1 hexane-EtOAc) yielded 4.31 g (87%) of an oil; homogeneous by TLC in 9:1 hexane-EtOAc. 400 MHz $^1$H NMR (CDCl$_3$) was consistent with the assigned structure.

Step CCC 2-methyl-2-(4-nitrophenyl)propionic acid

A solution of 11 g (24 mmol) of 2-methyl-2-(4-nitrophenyl)propionic acid ethyl ester in 1 liter of 0.5M potassium hydroxide in methanol was stirred under nitrogen and heated to about 50° C., at which time 111 mL of water was added gradually. The resulting solution was stirred at reflux overnight and then concentrated in vacuo. The residue was partitioned between ethyl acetate-tetrahydrofuran and 0.5N hydrochloric acid. The aqueous layer was also repeatedly extracted with chloroform. The organic fractions were dried over magnesium sulfate and concentrated in vacuo to yield 9.4 g (94%) of an amorphous, yellow-brown solid; homogeneous by TLC in 95:5:0.5 CH$_2$Cl$_2$-MeOH-AcOH. 500 MHz $^1$H NMR (CDCl$_3$) was consistent with the assigned structure.

Step DDD N,N-diethyl-2-(4-nitrophenyl)isobutyramide

To 8.36 g (40 mmol) of 2-methyl-2-(4-nitrophenyl) propionic acid were added 18 mL of cyclohexane and 9 mL of thionyl chloride. The mixture was stirred under nitrogen and heated to reflux. The solid gradually dissolved, and gas evolution was observed. After 20 hours, the solution was cooled and evaporated under a stream of nitrogen and then dried in vacuo. The residual light orange solid was dissolved in 50 mL of anhydrous tetrahydrofuran and added dropwise to a solution of 9.10 mL (6.43 g, 88 mmol) of diethylamine in 100 mL of anhydrous tetrahydrofuran stirred in an ice-methanol bath at about −10° to −15° C. Upon completion of the addition, which was accompanied by precipitation, the mixture was allowed to warm gradually to room temperature. After 2 days, the mixture was concentrated in vacuo, and the residue was partitioned between 250 mL of ethyl acetate and 200 mL of water. The organic phase was washed further with water, then with saturated aqueous sodium bicarbonate solution, and finally with brine. The ethyl acetate solution was dried over magnesium sulfate, filtered, and concentrated in vacuo. The residual oil was purified by flash chromatography on silica gel (elution with 6:1 and then 5:1 hexane-ethyl acetate) to yield 9.45 g (85%) of pale yellow solid, mp 59.5°–61° C.; homogeneous by TLC in 2:1 hexane-EtOAc. 500 MHz $^1$H NMR (CDCl$_3$) was consistent with the assigned structure. Mass spectrum (PB-NH3/CI): m/e=265 (M+H).

Step EEE 2-(4-aminophenyl)-N,N-diethylisobutyramide

A mixture of 9.38 g (35.5 mmol) of N,N-diethyl-2-(4-nitrophenyl)isobutyramide, 400 mg of 10% palladium on carbon, and 120 mL of absolute ethanol was shaken with hydrogen (initial hydrogen pressure 47 psig) in a pressure vessel for 22 hours. The catalyst was removed by filtration through diatomaceous earth under nitrogen, and the filter cake was washed with additional ethanol. Concentration of the filtrate in vacuo gave 8.5 g (100%) of off-white solid, mp 89°–90° C.; homogeneous by TLC in 98:2 CH$_2$–C$_2$-MeOH. 500 MHz $^1$H NMR (CDCl$_3$) was consistent with the assigned structure. Mass spectrum (PB-NH$_3$/CI): m/e=235 (M+H).

Step FFF N,N-diethyl-2-(4-hydrazinophenyl)isobutyramide

To 8.5 g (35.5 mmol) of 2-(4-aminophenyl)-N,N-diethylisobutyramide was added 35.5 mL of concentrated hydrochloric acid, and the mixture was agitated until a homogeneous solution was obtained. This was then stirred at −10° to −5° C. in an ice-acetone bath as a solution of 2.55 g (36.9 mmol) of sodium nitrite in 15.3 mL of water was added dropwise over about 25 minutes. Stirring was continued at this temperature for an additional hour. The mixture was kept cold and added in small portions over a period of 1 hour to a solution of 40.1 g (178 mmol) of stannous chloride dihydrate in 28.5 mL of concentrated hydrochloric acid stirred under nitrogen in an ice-acetone bath (approx. −10° C.). After completion of the addition, stirring was continued in the cooling bath for 1 hour. The mixture was then allowed to warm almost to room temperature while being stirred vigorously, resulting in a homogeneous solution. This solution was partitioned between 500 mL of ethyl acetate and 50 mL of water. The ethyl acetate layer was washed with an additional 50 mL of water and then treated cautiously with 500 mL of half-saturated aqueous sodium bicarbonate solution. The mixture was agitated cautiously, resulting in considerable gas evolution and precipitation. The thick mixture was filtered prior to separation of the phases. The ethyl acetate phase was washed with 50 mL of brine, then dried over magnesium sulfate filtered, and concentrated in vacuo at room temperature. This yielded 7.04 g (80%) of somewhat tacky orange solid, which was ill-defined by TLC, NMR, and mass spectrum but was suitable for use in the next step.

EXAMPLE 7.2 solution was concentrated in vacuo, and the residue was flash chromatographed of silica gel (gradient elution with 0–10% MeOH in $CH_2Cl_2$). Fractions containing product and a small amount of unreacted starting material were combined and concentrated to give 3.00 g of light beige, stiff foam, used directly in the next step without further purification or characterization.

Step 7.2B 2-[3-[2-[Benzyloxycarbonyl-[4-(pyridin-3-yl)butyl]amino]ethyl]-2-(3,5-dimethylphenyl)-1H-indol-5-yl]-2-methylpropionic Acid Ethyl Ester A solution of 3.00 g (theoretical maximum of 5.86 mmol) of crude 2-[2-(3,5-dimethylphenyl)-3-[2-[4-(pyridin-3-yl)butylamino]ethyl]-1H-indol-5-yl]-2-methylpropionic acid ethyl ester in 30 ml of dry $CH_2Cl_2$ was stirred under $N_2$ with cooling in a dry-ice-acetone bath. To this solution was added by syringe 1.106 ml (820 mg, 6.36 mmol) of N,N-diisopropylethylamine. Then 956μ (1.14 g, 6.36 mmol) of benzyl chloroformate was added dropwise by syringe over 5–10 minutes. After 20 minutes, the solution was removed from the cooling bath and allowed to warm to room temperature. After 2 hours, the solution was diluted with 50 ml of $CH_2Cl_2$, transferred to a separatory funnel, and shaken with 80 ml of $H_2O$. The organic phase was dried over $MgSO_4$, filtered, and concentrated in vacuo. Flash chromatography of the residual gum on silica gel (gradient elution with 0.2–2% MeOH in $CH_2Cl_2$) gave 2.81 g (55% overall for Steps 1 and 2) of pale, golden-yellow gum; virtually homogeneous by TLC in 95:5 $CH_2Cl_2$-MeOH. 500 MHz $^1$H NMR ($CDCl_3$) was complex, owing to rotamers, but appeared to be consistent with the assigned structure. Mass spectrum (ESI): m/e 646 (M+H)$^+$.

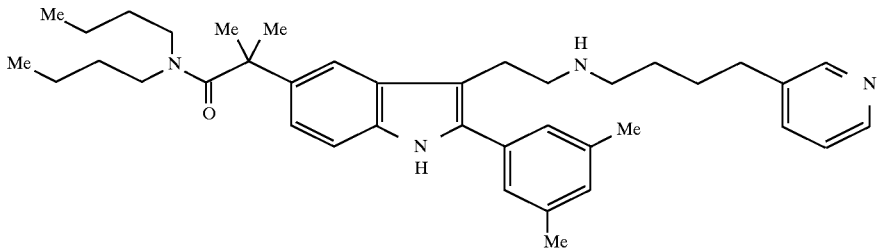

2-[2-(3,5-dimethylphenyl)-3-[2-[4-(pyridin-3-yl)butylamino]ethyl]-1H-indol-5-yl]-N,N-dibutylisobutyramide Step 7.2A 2-[2-(3 5-dimethylphenyl)-3-[2-[4-(pyridin-3-yl)butylamino]ethyl]-1H-indol-5-yl]-2-methylpropionic acid ethyl ester A dry flask containing 3.00 g (7.93 mmol) of 2-[3-(2-aminoethyl)-2-(3,5-dimethylphenyl)-1H-indol-5-yl]-2-methylpropionic acid ethyl ester (prepared essentially as described in Example 7.1 Step A), 4.76 g (39.7 mmol) of anhydrous $MgSO_4$, and a magnetic stirring bar was fitted with a septum and needle adapter leading to a Firestone valve. The flask was thoroughly purged with $N_2$, and the mixture was cooled in an ice-MeOH bath at −10° to −5° C. and stirred vigorously as a solution of 1.32 g (8.88 mmol) of 4-(pyridin-3-yl)butyraldehyde in 15 ml of dry $CDCl_3$ was added gradually by syringe over 10–15 minutes. The resulting mixture was stirred under $N_2$ at −10° to −5° C. for 40–45 minutes. Then the septum was removed just long enough to add 390 mg (10.3 mmol) of sodium borohydride. The mixture was stirred under $N_2$ at −10° to −5° C. as 10 ml of dry MeOH was added dropwise by syringe over several minutes. After 30 minutes, the mixture was removed from the cooling bath and partitioned between 90 ml of EtOAc and 90 ml of $H_2O$. The organic layer was washed with 2×30 ml of brine, then dried over anhydrous $Na_2SO_4$. The filtered Step 7.2C 2-[3-[2-[benzyloxycarbonyl-[4-(pyridin-3-yl)butyl]amino]ethyl]-2-(3,5-dimethylphenyl)-1H-indol-5-yl]-2-methylpropionic acid A mixture of 2.78 g (4.30 mmol) of 2-[3-[2-[benzyloxycarbonyl-[4-(pyridin-3-yl)butyl]amino]ethyl]-2-(3,5-dimethylphenyl)- 1H-indol-5-yl]-2-methylpropionic acid ethyl ester in 43.0 mol (21.5 mmol) of 0.5M KOH in MeOH and 25 ml of THF was stirred under $N_2$ and heated to reflux. To the resulting solution was gradually added 18 ml of $H_2O$, and the solution was maintained at reflux for 39 hours. It was then cooled and concentrated to small volume, accompanied by precipitation. The mixture was treated with 10.75 ml (21.5 mmol) of 2N HCl and agitated for a few minutes. The solid was collected on a filter and washed thoroughly with $H_2O$. After suction-drying under $N_2$, the solid was triturated and washed with diethyl ether and vacuum-dried to yield 2.43 g (92%) of cream-colored powder, mp 152°–154° C. (partial dec.); homogeneous by TLC in 90:10 $CH_2Cl_2$-MeOH. 500 MHz $^1$H NMR (DMSO-$d_6$) was consistent with the assigned structure. Mass spectrum (ESI): m/e 618 (M+H)$^+$.

Step 7.2D [2-[5-(1-dibutylcarbamoyl-1-methylethyl)-2-(3,5-dimethylphenyl)-1H-indol-3-yl]ethyl]-4-(pyridin-3-yl)butyl]carbamic acid benzyl ester A solution of 92.7 mg (0.15 mmol) of 2-[3-[2-[benzyloxycarbonyl-[4-(pyridin-3-yl)butyl]amino]ethyl]-2-

(3,5-dimethylphenyl)-1H-indol-5-yl]-2-methylpropionic acid, 83.2 mg (0.16 mmol) of PyBOP reagent, and 0.151 mL (116 mg; 0.9 mmol) of triethylamine in 0.750 mL of dry CH$_2$Cl$_2$ was stirred at room temperature in a stoppered flask for 2 days. The solution was then partitioned between 10 ml of EtOAc and 10 ml of 0.5N HCl. The organic phase was washed with 10 ml of saturated aqueous NaHCO$_3$ solution and then with 5 ml of saturated aqueous NaCl solution. The EtOAc phase was then dried (MgSO$_4$), filtered, and concentrated in vacuo at room temperature. The residue was purified by preparative TLC on 6 Analtech tapered silica gel plates (20×20 cm), which were developed in 95:5 CH$_2$Cl$_2$-MeOH. The product band from each plate was isolated, combined, and extracted with 95:5 CH$_2$Cl$_2$-MeOH. Concentration of the extracts in vacuo yielded 85.2 mg (78%) of a light golden-yellow gum; virtually homogeneous by TLC in 95:5 CH$_2$Cl$_2$-MeOH. 500 MHz 1H NMR (CDCl$_3$) was complex, owing to rotamers, but was consistent with the assigned structure. Mass spectrum (ESI): m/e 729.7 (M+H)$^+$.

Step 7.2E 2-[2-(3,5-dimethylphenyl)-3-[2-[4-(pyridin-3-yl)-butylamino]ethyl]-1H-indol-5-yl]-N,N-dibutylisobutyramide A mixture of 76.5 mg (0.105 mmol) of [2-[5-(1-dibutylcarbamoyl-1-methylethyl)-2-(3,5-dimethylphenyl)-1H-indol-3-yl]ethyl]-[4-(pyridin-3-yl)butyl]carbamic acid benzyl ester, 40 mg of 10% palladium on carbon, 4 ml of absolute EtOH, and 4 ml of EtOAc was shaken with H$_2$ (approx. 47 psig) in a pressure vessel for 6 hours. The catalyst was removed by filtration through Celite under N$_2$, and the filtrate was concentrated in vacuo at room temperature. The residue was purified by preparative TLC on 4 Analtech tapered silica gel plates (20×20 cm), which were developed in 92.5:7.5:0.75 CH$_2$Cl$_2$-MeOH-concentrated NH$_4$OH. The product band from each plate was isolated, combined, and extracted with 92.5:7.5:0.75 CH$_2$Cl$_2$-MeOH-concentrated NH$_4$OH. Concentration of the extracts in vacuo yielded 51.4 mg (82%) of a pale yellow, stiff gum; homogeneous by TLC in 92.5:7.5:0.75 CH$_2$Cl$_2$-MeOH-concentrated NH40H. 500 MHz $^1$H NMR (CDCl$_3$) was consistent with the assigned structure. Mass spectrum (ESI): m/e 595.6 (M+H)$^+$.

Following a procedure similar to that described in EXAMPLES 7.1 and 7.2, the following compounds were prepared:

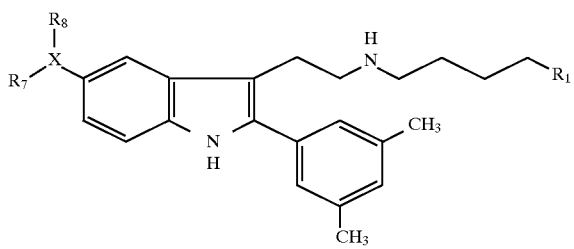

| Example # | X-R$_7$,R$_8$ | R$_1$ | m/e |
|---|---|---|---|
| 7A | Me-CH$_2$-N(Me-CH$_2$)-C(Me)(Me)-C(O)- | 4-pyridyl | 539 (M + H) |
| 7A | Me-CH$_2$-N(Me-CH$_2$)-C(Me)(Me)-C(O)- | 3-pyridyl | 539 (M + H) |
| 7B | MeOCH$_2$CH$_2$-N(MeOCH$_2$CH$_2$)-C(Me)(Me)-C(O)- | 3-pyridyl | 599 (M + H) |
| 7C | MeOCH$_2$CH$_2$-N(MeOCH$_2$CH$_2$)-C(Me)(Me)-C(O)- | 4-pyridyl | 599 (M + H) |
| 7D | Me-N(Me)-C(Me)(Me)-C(O)- | 4-pyridyl | 511 (M + H) |
| 7E | Me-N(Me)-C(Me)(Me)-C(O)- | 3-pyridyl | 511 (M + H) |
| 7F | Me$_2$CHCH$_2$-N(CH$_2$CHMe$_2$)-C(Me)(Me)-C(O)- | 4-pyridyl | 595 (M + H) |
| 7G | Me$_2$CHCH$_2$-N(CH$_2$CHMe$_2$)-C(Me)(Me)-C(O)- | 3-pyridyl | 595 (M + H) |
| 7H | Me(CH$_2$)$_3$-N((CH$_2$)$_3$Me)-C(Me)(Me)-C(O)- | 4-pyridyl | 595 (M + H) |
| 7I | cyclopropyl-CH$_2$-N(Et)-C(Me)(Me)-C(O)- | 3-pyridyl | 579 (M + H) |
| 7J | MeCH(Me)-NH-C(Me)(Me)-C(O)- | 3-pyridyl | 525 (M + H) |

-continued

| Example # | X-R₇R₈ | R₁ | m/e |
|---|---|---|---|
| 7K | Me-NH-C(O)-C(Me)₂-Me | 3-pyridyl | 511 (M + H) |
| 7L | (Me)(Me-CH₂)N-C(O)-C(Me)₂-Me | 3-pyridyl | 553 (M + H) |
| 7M | (cyclohexyl)(Me-CH₂)N-C(O)-C(Me)₂-Me | 3-pyridyl | 593 (M + H) |
| 7N | (cyclohexyl)(Me-CH₂)N-C(O)-C(Me)₂-Me | 4-pyridyl | 593 (M + H) |
| 7O | H₂N-C(O)-C(Me)₂-Me | 3-pyridyl | 483 (M + H) |
| 7P | EtO-C(O)-C(Me)₂-Me | 4-pyridyl | 526 (M + H) |

EXAMPLE 8

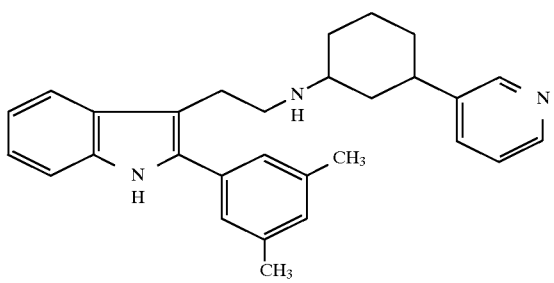

{2-[2-(3,5-dimethylphenyl)-1H-indol-3-yl]ethyl}-(3-pyridin-3-yl-cyclohexyl)amine To a solution of 3-pyridin-3-yl-cyclohexanone (30 mg in 1.5 mL dry CDCl₃) at 0° C. was added a solution of 2-[2-(3,4-dimethoxyphenyl)-1H-indol-3-yl]-ethylamine (45.3 mg in 1 mL dry CDCl₃) followed by 206 mg magnesium sulfate and the mixture stirred at low temperature. After 15 minutes, 26 mg sodium borohydride was added followed by 1.0 mL methanol and the mixture stirred for an additional 30 minutes. At this time the reaction was quenched by the addition of 2N hydrochloric acid and evaporated to dryness. Purification of the concentrate by preparative TLC on silica gel (methylene chloride:methanol, 9:1) gave the title compound (8.4 mg).

PREPARATION OF SYNTHETIC INTERMEDIATES 3-pyridin-3-yl-cyclohexanone

Step A 3-pyridin-3-yl-cyclohex-2-enone

To a solution of 3-ethoxy-2-cyclohexen-1-one (1.4 g in 10 mL dry tetrahydrofuran) was added 1.58g 4-bromopyridine and the mixture stirred vigourously at −78° C. To this was added dropwise tert-butyllithium (11.8 mL of a 1.7M solution in pentane) and the reaction allowed to proceed at low temperature. After 2 hours, the reaction was quenched by the addition of 2N hydrochloric acid and heated to reflux for 14 hours. At this time the mixture was cooled and neutralized to pH7 by the careful addition of 1N sodium hydroxide. The mixture was then extracted with methylene chloride and the organic portion dried over sodium sulfate. Purification of the concentrate by flash chromatography on silica gel (ethyl acetate:hexane, 1:1; then 2:1) gave the title compound (1.37 g).

Step B 3-pyridin-3-yl-cyclohexanone

To a solution of 3-pyridin-3-yl-cyclohex-2-enone (1.25 g in 50 mL ethanol) was added 164 mg of platinum oxide catalyst and the mixture subjected to hydrogen at 40 psi. After 2 hours, the catalyst was removed by filtration and the filtrate concentrated in vacuo. Purification of the residue by flash chromatography on silica gel (ethyl acetate:hexane, 1:1) gave the title compound (427 mg).

Following a procedure similar to that described in Example 8, the following compounds were prepared:

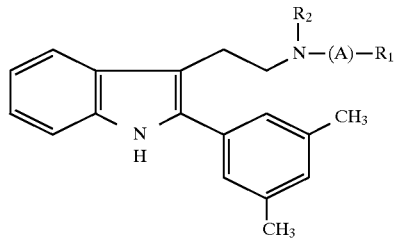

| Example # | (A) | R₂ | R₁ | m/e |
|---|---|---|---|---|
| 8A | —CH₂CH₂— | —(CH₂)₄-4-(phenyl-4-OMe) | 4-pyridyl | 532 (M + H) |
| 8B | —CH₂CH₂— | —(CH₂)₄—(phenyl-4-OH) | 4-pyridyl | 518 (M + H) |
| 8C | —CH₂C(Me)₂CH₂CH₂— | —H | 4-pyridyl | 426 (M + H) |
| 8D | cyclohexyl | —H | 3-pyridyl | 424 (M + H) |
| 8E | cyclopentyl | —H | 3-pyridyl | 410 (M + H) |
| 8F | cyclohexyl-OH | —H | 3-pyridyl | 440 (M + H) |

EXAMPLE 9.1

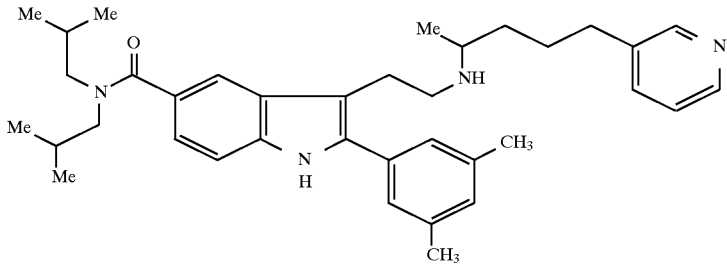

2-(3,5-dimethylphenyl)-3-[2-(1-methyl-4-pyridin-3-yl-butylamino)ethyl]-1H-indole-5-carboxylic acid diisobutylamide Step 9.1A 3-(2-tert-butoxycarbonylamino-ethyl)-2-(3,5-dimethylphenyl)-1H-indole-5-carboxylic acid ethyl ester To a solution of 3-(2-aminoethyl)-2-(3,5-dimethylphenyl)-1H-indole-5-carboxylic acid ethyl ester (prepared as described in Example 5.1, 1.5 g in 30 mL dry tetrahydrofuran) at 0° C. was added a solution of di-tert-butyl dicarbonate (1.9 g in 3 mL tetrahydrofuran) followed by an aqueous solution of potassium carbonate (1 g in 10 mL water) and the resulting suspension stirred vigourously at 0° C. After 12 minutes, the reaction was quenched by the addition of excess saturated aqueous ammonium chloride and the mixture extracted with ethyl acetate. The organic portion was dried over sodium sulfate and concentrated in vacuo. The resulting solid was washed sequentially with methylene chloride, hexane and ethyl acetate to give the title compound (1.77 g).

Step 9.1B 3-(2-tert-butoxycarbonylaminoethyl)-2-(3 5-dimethylphenyl)-1H-indole-5-carboxylic acid To a suspension of 3-(2-tert-butoxycarbonylamino-ethyl)-2-(3,5-dimethylphenyl)-1H-indole-5-carboxylic acid ethyl ester (830 mg in 50 mL methanol) was added 8 mL of a 1.25N sodium hydroxide solution and the mixture heated to 75° C. on an oil bath. After 5.5 hours, an additional 3 mL of 1.25N sodium hydroxide were added and the reaction allowed to proceed for 2 more hours. At this time the mixture was cooled to room temperature and the reaction quenched by the addition of pH2 buffer. The mixture was extracted with the ethyl acetate, washed with saturated ammonium chloride solution and the organic portion dried over sodium sulfate. Concentration in vacuo provided the crude acid in quantitative yield.

Step 9.1C {2-[5-diisobutylcarbamoyl-2-(3,5-dimethylphenyl)-1H-indol-3-yl]ethyl}carbamic acid tert-butyl ester To a solution of 3-(2-tert-butoxycarbonylaminoethyl)-2-(3,5-dimethylphenyl)-1H-indole-5-carboxylic acid (200 mg in 12 mL methylene chloride) was added 104 mg 1-hydroxybenzotriazole followed by 118 mg 1-(3-dimethylaminopropyl)-3-ethylcarbodiimide hydrochloride and the mixture stirred at room temperature. After 30 minutes, 0.35 mL of diisobutylamine was added and the mixture stirred at room temperature for 14 hours. The reaction was then concentrated in vacuo and purified by flash chromatography on silica gel (hexane:ethyl acetate, 2:1) to give the title compound (230 mg).

Step 9.1D 3-(2-aminoethyl)-2-(3,5-dimethylphenyl)-1H-indole-5-carboxylic acid diisobutylamide To a solution of {2-[5-diisobutylcarbamoyl-2-(3,5-dimethyl-phenyl)-1H-indol-3-yl]-ethyl}carbamic acid tert-butyl ester (230 mg in 12 mL methylene chloride) at 0° C. was added 0.55 mL anisole followed by 3.4 mL trifluoroacetic acid and the mixture stirred at 0° C. After 1 hour, the mixture was concentrated in vacuo and the residual acid removed by azeotrope with toluene. Purification of the concentrate by flash chromatography on silica gel (methylene chloride:methanol:ammonium hydroxide, 90:8:1) gave the title compound (173 mg).

Step 9.1E 2-(3,5-dimethylphenyl)-3-[2-(1-methyl-4-pyridin-3-yl-butylamino)ethyl]-1H-indole-5-carboxylic acid diisobutylamide To a solution of 3-(2-aminoethyl)-2-(3,5-dimethylphenyl)-1H-indole-5-carboxylic acid diisobutylamide (142 mg in dry methanol) was added 19 mg 5-pyridin-3-yl-pentan-2-one and the pH adjusted to 6 by the addition of trifluoroacetic acid. To this, approximately 10 mg of 3 Å molecular sieves were added followed by 27 mg of sodium cyanoborohydride. The pH was adjusted occasionally with trifluoroacetic acid over 36 hours to maintain pH of 6. The reaction was then quencehed by the addition of aqueous potassium carbonate and the mixture extracted with ethyl acetate. The organic portion was washed sequentially with aqueous potassium carbonate and brine, then dried over sodium sulfate. Purification of the concentrate by flash chromatography on silica gel (methylene chloride:methanol:ammonium hydroxide, 90:8:1) gave the title compound (32 mg) [m/e =567 (M+H)] plus unreacted amine (115 mg).

PREPARATION OF SYNTHETIC INTERMEDIATES

Step A 4-pyridin-3-yl-butyraldehyde

To a solution of oxalyl chloride (0.74 mL in 5 mL dry methylene chloride) at −78° C. was added a solution of methyl sulfoxide (0.90 mL in 5 mL methylene chloride) and the mixture stirred at low temperature for 15 minutes. A solution of 4-pyridin-3-yl-butan-1-ol (prepared essentially as described in Example 2.1, 820 mg in 10 mL methylene chloride) and the reaction allowed to proceed for 45 minutes after which time 4 mL triethylamine were added and the mixture allowed to warm to room temperature. After 35 minutes saturated sodium bicarbonate was addded and the mixture extracted with methylene chloride. The organic portion was washed with saturated sodium bicarbonate, dried over sodium sulfate and concentrated in vacuo to give the crude title compound (813 mg).

Step B 5-pyridin-3-yl-pentan-2-ol

To a solution of methylmagnesium bromide (0.75 mL of a 3M solution (diethyl ether) in 3.5 mL dry tetrahydrofuran) at 0° C. was added a solution of 4-pyridin-3-yl-butyraldehyde (133 mg in 1 mL tetrahydrofuran) and the mixture at low temperature. After 30 minutes, the reaction was quenched by the addition of saturated ammonium chloride and extracted with ethyl acetate. The organic portion was washed with saturated sodium bicarbonate, dried over sodium sulfate and concentrated in vacuo. Purification by flash chromatography on silica gel (methylene chloride:methanol, 95:5) gave the title compound (71 mg).

Step C 5-pyridin-3-yl-pentan-2-one

To a solution of oxalyl chloride (0.060 mL in 1 mL dry methylene chloride) at −78° C. was added a solution of methyl sulfoxide (0.075 mL in 0.25 mL methylene chloride) and the mixture stirred at low temperature for 18 minutes. A solution of 5-pyridin-3-yl-pentan-2-ol (71 mg in 1 mL methylene chloride) and the reaction allowed to proceed for 40 minutes after which time 0.35 mL triethylamine were added and the mixture allowed to warm to room temperature. After 35 minutes, water was addded and the mixture extracted with methylene chloride. The organic portion was washed with saturated sodium bicarbonate, dried over sodium sulfate and concentrated in vacuo. Purification of the residue by flash chromatography on silica gel (methylene chloride:methanol, 96:4) gave the title compound (61 mg).

EXAMPLE 9.2

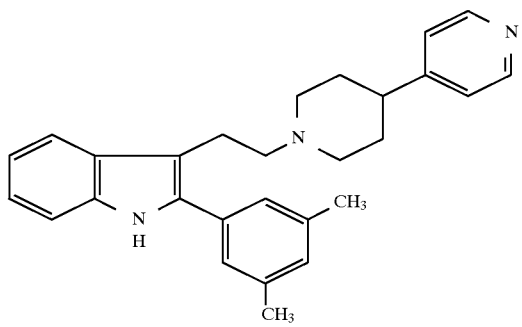

1-{2-[2-(3,5-dimethylphenyl)-1H-indol-3-yl]ethyl}-1, 2.3,4,5 6-hexahydro-[4,4']bipyridinyl Step 9.2A 1-[2-(3,5-dimethylphenyl)-1H-indol-3-yl]-2-(3,4,5,6-tetrahydro-2H-[4,4']bipyridinyl-1-yl)ethane-1,2-dione To a solution of 2-(3,5-dimethylphenyl)-1H-indole (200 mg in 2 mL dry methylene chloride) was added dropwise 0.083 mL oxalyl chloride and the mixture stirred at room temperature. After 1 hour, 213 mg 1,2,3,4,5,6-hexahydro-[4,4']bipyridinyl dihydrochloride was added followed by 1.5 mL methylene chloride and 0.567 mL triethylamine and the mixture continued stirring at room temperature. After 4 hours the reaction was diluted with ethyl acetate and washed sequentially with water, saturated aqueous ammonium chloride and brine. The organic portion was dried over sodium sulfate and the concentrate purified by flash chromatography on silica gel (methylene chloride:methanol, 96:4) to give the title compound (148 mg).

Step 9.2B 1-{2-[2-(3,5-dimethylphenyl)-1H-indol-3-yl]ethyl}-1,2,3,4,5,6-hexahydro-[4,4']bipyridinyl To a solution of 1-[2-(3,5-dimethylphenyl)-1H-indol-3-yl]-2-(3,4,5,6-tetrahydro-2H-[4,4']bipyridinyl-1-yl)ethane-1,2-dione (148 mg in dry tetrahydrofuran) was added dropwise 2.71 mL of a 1M solution of lithium aluminum hydride in tetrahydrofuran and the mixture heated to reflux on an oil bath. After 1.5 hours the mixture was cooled and quenched by the sequential addition of 30 mL water and 4 mL ammonium hydroxide and 25 mL ethyl acetate. The mixture was filtered to remove the solids. The organic portion was washed with brine, dried over magnesium sulfate and concentrated in vacuo to give the title compound (71 mg). m/e=410 (M+H).

EXAMPLE 9.3

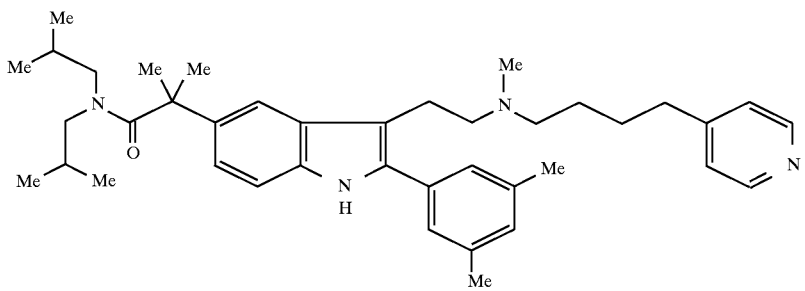

2-[2-(3,5-Dimethylphenyl)-3-[2-[methyl-[4-(pyridin-4-yl)butyl]amino]ethyl]-1H-indol-5-yl]-N,N-dibutylisobutyramide A dry flask containing 67 mg (0.113 mmol) of 2-[2-(3,5-dimethylphenyl)-3-[2-[methyl-[4-(pyridin-4-yl)butyl]amino]ethyl]-1H-indol-5-yl]-N,N-dibutylisobutyramide (prepared according to EXAMPLE 7.2), 33.9 mg (1.3 mmol) of paraformaldehyde, and 100 mg of powdered 3A molecular sieves was fitted with a septum and purged thoroughly with $N_2$. Next, 2.65 mL of MeOH and 65.2 μL (67.8 mg, 1.13 mmol) of glacial acetic acid were added, and the mixture was stirred at room temperature for 35 minutes. Then 28.4 mg (0.452 mmol) of sodium cyanoborohydride was added, followed after an additional 20 minutes by 2.5 mL of anhydrous THF. After a few minutes, TLC indicated complete reaction. Therefore, the mixture was filtered, and the filtrate was shaken in a separatory funnel with brine. The aqueous phase was extracted an additional 3 times with $CH_2Cl_2$. The combined organic fractions were dried over $Na_2SO_4$, filtered, and concentrated in vacuo. The residue was flash chromatographed on silica gel (gradient elution with 99:1:0.1 to 95:5:0.5 $CH_2Cl_2$-MeOH-concd. $NH_4OH$) to yield 31.1 mg (45%) of the title compound as a glass; homogeneous by TLC in 95:5:0.5 $CH_2Cl_2$-MeOH-concd. $NH_4OH$. 500 MHz $^1H$ NMR ($CDCl_3$) was consistent with the assigned structure. m/e=609.5 (M+H).

Following a procedure similar to that described in EXAMPLES 9.1, 9.2 and 9.3, the following compounds were prepared:

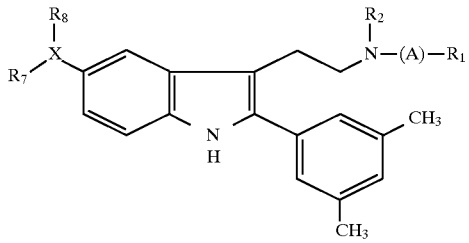

| Example # | —N(R₂)—(A)— | XR₇,R₈ | R₁ | m/e |
|---|---|---|---|---|
| 9A | —N(piperidine-4-yl with CO₂et) | —NH—CO—N(Et)₂ | 3-pyridyl | 596 (M + H) |
| 9B | —N(piperidine-4-yl with CO₂H) | —NH—CO—N(Et)₂ | 3-pyridyl | 568 (M + H) |
| 9C | —N(piperidine-4-yl with CO₂et) | —NH—CO—(4-morpholine) | 3-pyridyl | 610 (M + H) |
| 9D | —N(piperidine-4-yl with CO₂H) | —NH—CO—(4-morpholine) | 3-pyridyl | 582 (M + H) |
| 9E | —N(piperidine-4-yl) | —NH—CO—N(Et)₂ | 3-pyridyl | 524 (M + H) |
| 9F | —N(piperazinyl)—N-Et | —H | 3-pyridyl | 425 (M + H) |
| 9G | —N(piperazinyl)—N-Et | —H | 4-pyridyl | 425 (M + H) |
| 9H | —N(piperazinyl)—N— | —H | 4-pyridyl | 425 (M + H) |
| 9I | —NHCH₂CH₂CH₂O— | —COOEt | 2,4-disubstituted aryl (Pr, Et, dioxy) | 582 (M + H) |
| 9J | H-N-(4-hydroxy-4-methylcyclohexyl) | C(O)N-(iBu)₂ | 4-pyridyl | 595 (M + H) |
| 9K | —NHCH₂CH₂CH₂O— | C(O)N-(iBu)₂ | 3-pyridyl | 555 (M + H) |
| 9L | —NHCH₂CH(Me)CH₂CH₂— | C(O)N-(iBu)₂ | 3-pyridyl | 553 (M + H) |
| 9M | —NH—CH(Me)CH₂CH₂CH₂— | C(O)N-(iBu)₂ | 4-pyridyl | 567 (M + H) |
| 9N | (cis)-NHCH₂CH=CH— | C(O)N-(iBu)₂ | 3-pyridyl | 537 (M + H) |
| 9N | (trans)-—NHCH₂CH=CH— | C(O)N-(iBu)₂ | 3-pyridyl | 537 (M + H) |
| 9O | —NHCH₂CH₂CH(Me)— | C(O)N-(iBu)₂ | 4-pyridyl | 553 (M + H) |
| 9P | —NHCH₂CH₂CH(Me)— | C(O)N-(iBu)₂ | 3-pyridyl | 553 (M + H) |
| 9Q | —NHCH₂—O—CH₂— | C(O)N-(iBu)₂ | 3-pyridyl | 555 (M + H) |
| 9R | —N(Et)-CH₂CH₂CH₂CH₂— | C(Me)₂—C(O)N-(iBu)₂ | 4-pyridyl |  |

-continued

| Example # | —N(R$_2$)—(A)— | XR$_7$,R$_8$ | R$_1$ | m/e |
|---|---|---|---|---|
| 9S | —NHCH$_2$CH(CH$_3$)CH$_2$—CH$_2$— | C(O)N-(iBu)$_2$ | 3-pyridyl | 567 (M+H) |
| 9T | —NHCH$_2$CH$_2$CH$_2$—CH(CH3)— | C(O)N-(iBu)$_2$ | 4-pyridyl | 567 (M+H) |
| 9U | —NHCH$_2$CH$_2$—CH(CH$_3$)CH$_2$— | C(O)N-(iBu)$_2$ | 3-pyridyl | 567 (M+H) |
| 9V | —NHCH(CH$_3$)CH$_2$— | C(O)N-(iBu)$_2$ | 3-pyridyl | 539 (M+H) |
| 9W | —N(Me)—CH$_2$CH$_2$CH$_2$CH$_2$— | C(O)N-(Et)$_2$ | 4-pyridyl | — |
| 9X | —NHC(CH$_3$)$_2$CH$_2$CH$_2$—CH$_2$— | C(O)N-(iBu)$_2$ | 3-pyridyl | 581 (M+H) |
| 9Y | —NHC(CH$_3$)$_2$CH$_2$CH$_2$—CH(OH)— | C(O)N-(iBu)$_2$ | 3-pyridyl | 597 (M+H) |
| 9Z | —NHC(CH$_3$)$_2$CH=CH—CH(OH)— | C(O)N-(iBu)$_2$ | 3-pyridyl | 595 (M+H) |
| 9Z | —NHC(CH$_3$)$_2$CH$_2$CH$_2$—CH$_2$— | C(Me)$_2$—C(O)N-(Et)$_2$ | 3-pyridyl | 567 (M+H) |
| 9AA | —NHCH$_2$CH$_2$— | C(O)N-(iBu)$_2$ | 3-pyridyl | 525 (M+H) |
| 9BB | —NHCH$_2$CH$_2$ | C(Me)$_2$—C(O)N-(Et)$_2$ | 3-pyridyl | 511 (M+H) |
| 9CC | —NHC(CH$_3$)$_2$CH=CH— | C(O)N-CH(OH)(iBu)$_2$ | 4-pyridyl | 595 (M+H) |
| 9DD | —NHC(CH$_3$)$_2$CH$_2$CH$_2$—CH(OH)— | C(O)N-(iBu)$_2$ | 4-pyridyl | 597 (M+H) |
| 9EE | —NHC(CH$_3$)$_2$CH$_2$CH$_2$—CH$_2$— | C(O)N-(iBu)$_2$ | 4-pyridyl | 581 (M+H) |
| 9FF | —NHC(CH$_3$)$_2$CH=CH—CH(OH)— | C(Me)$_2$—C(O)N-(Et)$_2$ | | 581 (M+H) |
| 9GG | —NHC(CH$_3$)$_2$CH$_2$CH$_2$—CH$_2$— | C(Me)$_2$—C(O)N-(Et)$_2$ | 4-pyridyl | 567 (M+H) |
| 9HH | —NHC(CH$_3$)$_2$CH$_2$CH$_2$—CH$_2$— | C(Me)$_2$—C(O)N-(Et)$_2$ | 4-pyridyl | 567 (M+H) |
| 9II | —NHCH$_2$CH(CH$_2$CH$_3$)$_{CH2}$CH$_2$— | C(O)N-(iBu)$_2$ | 4-pyridyl | 581 (M+H) |
| 9JJ | —NHCH$_2$CH$_2$— | C(Me)$_2$—C(O)N-(Et)$_2$ | 4-pyridyl | 511 (M+H) |
| 9KK | —NHCH$_2$CH$_2$— | C(O)N-(iBu)$_2$ | 4-pyridyl | 525 (M+H) |

EXAMPLE 10

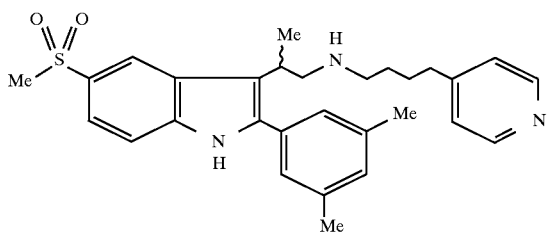

{2-[2-(3,5-dimethylphenyl)-5-methanesulfonyl-1H-indol-3-yl]propyl}-(4-pyridin-4-yl-butyl) amine Step 10A 2-methylcyclopropanecarboxylic acid N-methoxy-N-methyl-amide To a solution of 2-methylcyclopropanecarboxylic acid (10 g in a mixture of 200 mL benzene and 2 mL N,N-dimethylformamide) at 0° C. was added 10.5 mL of oxalyl chloride and the mixture stirred at 0° C. for 30 minutes then warmed to room temperature for 30 minutes. At this time, 14.6 g of N,O-dimethylhydroxylamine hydrochloride was added followed by 41 mL of triethylamine. The mixture was stirred at room temperature for one hour then quenched by the addition of saturated sodium bicarbonate. The aqueous portion was extracted with ethyl acetate and the combined organics washed with brine, dried over sodium sulfate and concentrated in vacuo. The product was purified by distillation under reduced pressure to give 8.9 g as an oil.

Step 10B (3,5-dimethylphenyl)-(2-methylcyclopropyl) methanone

To a solution of 5-bromo-meta-xylene (5.7 mL in 120 mL of dry tetrahydrofuran) at −78° C. was added 30.6 mL of a 1.4M solution of n-butyllithium in hexane and the mixture stirred at low temperature. After 15 minutes, a solution of 2-methylcyclopropanecarboxylic acid N-methoxy-N-methyl-amide (5.0 g in 50 mL tetrahydrofuran) was added dropwise over 5 minutes and the mixture then allowed to warm slowly to room temperature. After 1 hour, the reaction was quenched by the addition of 20 mL 2N hydrochloric acid and 40 mL water. This was extracted with ethyl acetate washed with saturated sodium bicarbonate and brine then dried over sodium sulfate to give 6.95 g of the title compound (crude).

Step 10C 2-[2-(3,5-dimethylphenyl)-5-methanesulfonyl-1H-indol-3-yl]propylamine

To a solution of (4-methanesulfonylphenyl)hydrazine (1.88 g in 20 mL n-butanol) at 95° C. was added (3,5-dimethylphenyl)-(2-methylcyclopropyl)methanone 2.24 g and heated to 110° C. on an oil bath. After 16 hours, the reaction was cooled to room temperature and poured into 200 mL diethyl ether and the resulting brown precipitate collected by filtration. The solids were dissolved in 300 mL water and extracted with diethyl ether. The aqueous portion was made basic by the addition of 1N sodium hydroxide and then extracted with diethyl ether. The combined organics were dried over sodium sulfate and concentrated in vacuo. Purification by flash chromatography on silica gel (methylene chloride:methanol, 9:1) gave the title compound (313 mg).

Step 10D {2-[2-(3,5-dimethylphenyl)-5-methanesulfonyl-1H-indol-3-yl]propyl}-(4-pyridin-4-yl-butyl)amine A mixture of 4-pyridin-4-yl-butyraldehyde (23 mg), 2-[2-(3,5-dimethylphenyl)-5-methanesulfonyl-1H-indol-3-yl] propylamine (50 mg) and magnesium sulfate (76 mg) were diluted with 1.5 mL $CDCl_3$ and stirred at −5° C. After 15 minutes, a solution of sodium borohydride (6.8 mg in 1.5 mL dry methanol) were added and the mixture stirred at low temperature for an additional 20 minutes. At this time the reaction was quenched by the addition of water, extracted with ethyl acetate and the organic portion washed sequentially with water and brine then dried over sodium sulfate. Purification of the concentrate by preparative TLC on silica gel (methylene chloride:methanol, 9:1) gave the title compound (29 mg).

Following a procedure similar to that described in EXAMPLES 7 and 10, the following compounds were prepared:

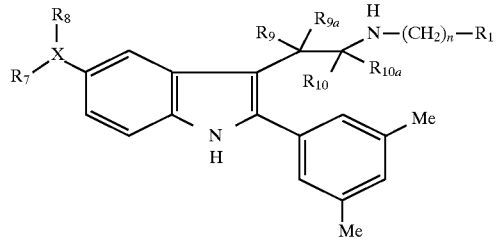

| Example # | $R_9 \diagdown R_{10} \diagup \substack{R_{9a} \\ R_{10a}}$ N— | $XR_7R_8$ | (CH$_2$)$_n$ | $R_1$ | m/e |
|---|---|---|---|---|---|
| 10A | MeO∼∼∼NH∼ | —NHC(O)Ph | 4 | 4-pyridyl | 575 (M + H) |
| 10B | Me∼∼NH∼ | EtO−C(O)−C(Me)$_2$− | 4 | 4-pyridyl | 526 (M + H) |

| Example # | R9, R9a, R10, R10a | XR7R8 | —(CH2)n— | R1 | m/e |
|---|---|---|---|---|---|
| 10C | Me-CH(Me)-CH2-NH-Me | (Et)2N-C(Me)2-C(=O)- | 4 | 4-pyridyl | 553 (M + H) |
| 10D | Me-CH(Me)-CH2-NH-Me | (Et)2N-C(Me)2-C(=O)- | 4 | 3-pyridyl | 553 (M +p0 H) |
| 10E | Me-CH(Me)-CH2-NH-Me | (Et)2N-C(Me)2-C(=O)- | 4 | 4-pyridyl | 553 (M+H) |
| 10F | Me-CH(Me)-CH2-NH-Me | (Et)2N-C(Me)2-C(=O)- | 4 | 4-pyridyl | 553 (M+H) |
| 10G | Me-CH(Me)-CH2-NH-Me | (Bui)2N-C(Me)2-C(=O)- | 4 | 4-pyridyl | 609 (M+H) |
| 10H | Et-CH(Me)-NH-Me | (Et)2N-C(Me)2-C(=O)- | 4 | 3-pyridyl | 553 (M+H) |
| 10I | Me-CH(Me)-CH2-NH-Me | EtO-C(Me)2-C(=O)- | 2 | 3-pyridyl | 498 (M+H) |

EXAMPLE 11

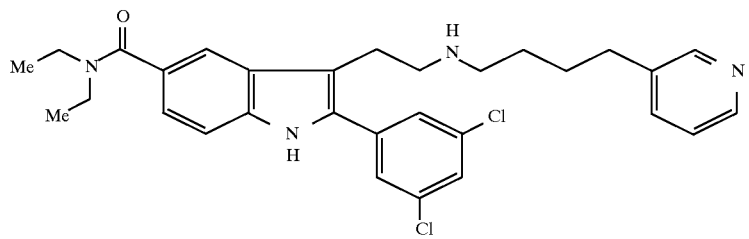

2-(3,5-dichlorophenyl)-3-[2-(4-pyridin-3-yl-butylamino) ethyl]-1H-indole-5-carboxylic acid diethylamide 11A 2-(3,5-dichlorophenyl)-3-[2-(4-pyridin-3-yl-butylamino)ethyl]-1H-indole-5-carboxylic acid ethyl ester To a solution of 3-(2-aminoethyl)-2-(3,5-dichlorophenyl)-1H-indole-5-carboxylic acid ethyl ester (prepared essentially as described in Example 5.1, 100 mg in 7.0 mL chloroform) at −5° C. was added 172 mg of magnesium sulfate followed by 46.3 mg of 4-pyridin-3-yl-butyraldehyde and the mixture stirred at low temperature for 15 minutes. At this time, a solution of sodium borohydride (13.7 mg in 1.2 mL dry methanol) was added and after another 40 minutes, the reaction was quenched by the addition of water. The mixture was partitioned between ethyl acetate and saturated potassium carbonate, extracted and the organic portion washed with brine and dried over sodium sulfate. Purification of the concentrate by flash chromatography on silica gel (methylene chloride:methanol, 92:8) gave the title compound (100 mg).

Step 11B 3-{2-[tert-butoxycarbonyl-(4-pyridin-3-yl-butyl)aminol]ethyl}-2-(3,5-dichlorophenyl)-1H-indole-5-carboxylic acid ethyl ester To a solution of 2-(3,5-dichlorophenyl)-3-[2-(4-pyridin-3-yl-butylamino]ethyl]-1H-indole-5-carboxylic acid ethyl ester (500 mg in 8 mL dry tetrahydrofuran) at 0° C. was added 331 mg of di-tert-butyl dicarbonate followed by an aqueous solution of poatssium carbonate (215 g in 4 mL water) and the resulting suspension stirred vigourously at 0° C. After 1 hour, the reaction was quenched by the addition of excess saturated aqueous ammonium chloride and the mixture extracted with ethyl acetate. The organic portion was dried over sodium sulfate and concentrated in vacuo. Purification of the residue by flash chromatography on silica gel (methylene chloride:methanol, 96.5:3.5) gave the title compound (472 mg).

Step 11C 3-{2-[tert-butoxycarbonyl-(4-pyridin-3-yl-butyl)amino]ethyl}-2-(3,5-dichlorophenyl)-1H-indole-5-carboxylic acid To a suspension of 3-{2-[tert-butoxycarbonyl-(4-pyridin-3-yl-butyl)amino]ethyl}-2-(3,5-dichlorophenyl)-1H-indole-5-carboxylic acid ethyl ester (65 mg in 4 mL methanol) at 0° C. was added 1.4 mL of a 1.25N sodium hydroxide solution and the mixture heated to 75° C. on an oil bath. After 2.5 hours the mixture was cooled to room temperature and the reaction quenched by the addition of saturated aqueous ammonium chloride. The mixture was extracted with the ethyl acetate, washed with saturated ammonium chloride solution and the organic portion dried over sodium sulfate. Concentration in vacuo provided the crude title compound (63 mg).

Step 11D {2-[2-(3,5-dichlorophenyl)-5-diethylcarbamoyl-1H-indol-3-yl]ethyl}-(4-pyridin-3-yl-butyl)carbamic acid tert-butyl ester To a suspension of 3-{2-[tert-butoxycarbonyl-(4-pyridin-3-yl-butyl)amino]ethyl}-2-(3,5-dichlorophenyl)-1H-indole-5-carboxylic acid (63 mg in 6 mL methylene chloride) was added 24.2 mg 1-hydroxybenzotriazole followed by 26.7 mg 1-(3-dimethylaminopropyl)-3-ethylcarbodiimide hydrochloride and the mixture stirred at room temperature. After 30 minutes, 0.06 mL of diethylamine was added and the mixture stirred at room temperature for 16 hours. The reaction was then concentrated in vacuo and purified by flash chromatography on silica gel (methylene chloride:methanol, 95:5) to give the title compound (63 mg).

Step 11E 2-(3,5-dichlorophenyl)-3-[2-(4-pyridin-3-yl-butylamino)ethyl]-1H-indole-5-carboxylic acid diethylamide To a solution of {2-[2-(3,5-dichlorophenyl)-5-diethylcarbamoyl-1H-indol-3-yl]ethyl}-(4-pyridin-3-yl-butyl)carbamic acid tert-butyl ester (63 mg in 3 mL methylene chloride) at 0° C. was added 0.15 mL anisole followed by 0.76 miL trifluoroacetic acid and the mixture stirred at 0° C. After 1.5 hours, an additional charge of 0.5 mL trifluoroacetic acid was added and stirring continued for another hour at which time the mixture was concentrated in vacuo and the residual acid removed by azeotrope with toluene. Purification of the concentrate by flash chromatography on silica gel (methylene chloride:methanol:ammonium hydroxide, 90:6.5:1) gave the title compound (38 mg). m/e=537 (M)

Following a procedure similar to that described in Example 11, the following compounds were prepared:

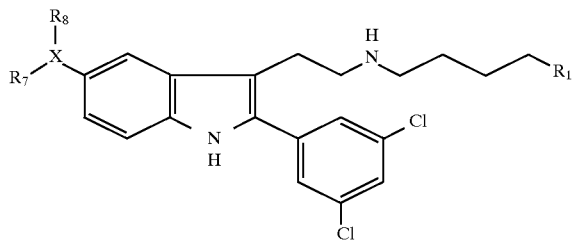

| Example # | XR$_7$, R$_8$ | R$_1$ | m/e |
|---|---|---|---|
| 11A | 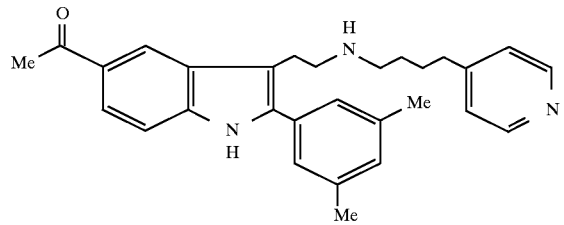 | 3-pyridyl | 582 (M + H) |
| 11B | —COOEt | 3-pyridyl | 510 (M) |
| 11C | —CON(iBu)$_2$ | 3-pyridyl | 593 (M) |
| 11D | —CON(nBu)$_2$ | 3-pyridyl | 593 (M) |
| 11E | —CON(Et)$_2$ | ![isoxazolyl-Me] | 541 (M) |

EXAMPLE 12.1

1-{2-(3,5-dimethylphenyl)-3-[2-(4-pyridin-4-yl-butylamino)ethyl]-1H-indol-5-yl}ethanone Step 12.1A: 3-{2-[tert-butoxycarbonyl-(4-pyridin-4-yl-butyl)-amino]-ethyl}-2-(3,5-dimethylphenyl)-1H-indole-5-carboxylic acid ethyl ester Prepared essentially as described in Example 9.1 Step A starting from 2-(3,5-Dimethylphenyl)-3-[2-[4-(pyridin-4-yl)butylamino]-ethyl]-1H-indole-5-carboxylic acid ethyl ester (Example 5.1 Step B) to give the title compound.

Step 12.1B 3-{2-[tert-butoxycarbonyl-(4-pyridin-4-yl-butyl)amino]ethyl}-2-(3,5-dimethylphenyl)-1H-indole-5-carboxylic acid Prepared essentially as described in Example 9.1 Step B starting from 3-{2-[tert-butoxycarbonyl-(4-pyridin-4-yl-butyl)-amino]-ethyl}-2-(3,5-dimethylphenyl)-1H-indole-5-carboxylic acid ethyl ester and using lithium hydroxide to give the title compound.

Step 12.1C {2-[2-(3,5-dimethylphenyl)-5-(methoxymethylcarbamoyl)-1H-indol-3-yl]-ethyl}(4-pyridin-4-yl-butyl)carbamic acid tert-butyl ester To a solution of 3-{2-[tert-butoxycarbonyl-(4-pyridin-4-yl-butyl)amino]ethyl}-2-(3,5-dimethylphenyl)-1H-indole-5-carboxylic acid (1.44 g in 25 mL N,N-dimethylformamide) at 0° C. was added 540 mg of 1-hydroxybenzotriazole (HOBt) followed by 0.44 mL 4-methylnorpholine and 365 mg N,O-dimethylhydroxylamine hydrochloride. After 15 minutes, 815 mg 1-(3-dimethylaminopropyl)-3-ethylcarbodiimide hydrochloride (EDC) was added and the mixture allowed to warm to room temperature. After 3 days reaction time, an additional portion of 540 mg of HOBt, 0.44 mL 4-methylmorpholine, 365 mg N,O-dimethylhydroxylamine hydrochloride and 815 mg EDC were added. The reaction stopped after 4 days by concentration in vacuo and reconcentration from toluene to remove all volatiles. The residue was solvated in ethyl acetate and washed sequentially with saturated aqueous sodium bicarbonate and brine, then dried over sodium sulfate. Purification of the concentrate by flash chromatography on silica gel (hexane:ethyl acetate, 30:70; then 20:80; then 0:100) gave the title compound (1.4 g).

Step 12.1D 3-{2-[tert-butoxycarbonyl-(4-pyridin-4-yl-butyl)amino]ethyl}-2-(3,5-dimethylphenyl)-5-(methoxymethylcarbamoyl)indole-1-carboxylic acid tert-butyl ester Prepared essentially as described in Example 9.1 Step A starting from {2-[2-(3,5-dimethylphenyl)-5-(methoxymethylcarbamoyl)-1H-indol-3-yl]-ethyl}(4-pyridin-4-yl-butyl)carbamic acid tert-butyl ester (1.4 g) to give the title compound (1.55 g).

Step 12.E 5-acetyl-3-{2-[tert-butoxycarbonyl-(4-pyridin-4-yl-butyl)amino]ethyl}-2-(3,5-dimethylphenyl)indole-1-carboxylic acid tert-butyl ester To a solution of 3-{2-[tert-butoxycarbonyl-(4-pyridin-4-yl-butyl)amino]ethyl}-2-(3,5 -dimethylphenyl)-5-(methoxymethylcarbamoyl) indole-1-carboxylic acid tert-butyl ester (0.069 g in 3 mL dry tetrahydrofuran) at −10° C. was added 0.20 mL of a 1.5M solution of methyllithium in ether and the mixture stirred at low temperature. After 45 minutes, the reaction was quenched by the addition of saturated aqueous ammonium chloride and extracted with ethyl acatate. The organic portion was washed with brine, dried over sodium sulfate and the concentrate purified by preparative TLC on silica gel (hexane:ethyl acetate, 2:3) to give the title compound (58 mg).

Step 12.1F 1-{2-(3,5-dimethylphenyl)-3-[2-(4-pyridin-4-yl-butylamino)ethyl]-1H-indol-5-yl}ethanone Prepared essentially as described in Example 9.1 Step D starting from 5-acetyl-3-{2-[tert-butoxycarbonyl-(4-pyridin-4-yl-butyl)amino]ethyl}-2-(3,5-dimethylphenyl)indole-1-carboxylic acid tert-butyl ester (120 mg) to give the title compound (82 mg). m/e=440 (M+H).

EXAMPLE 12.2

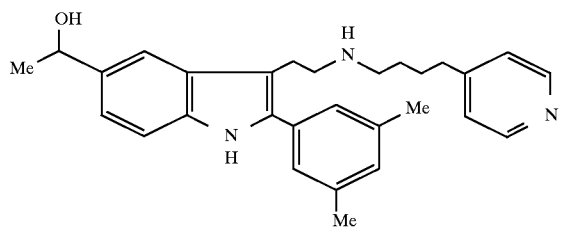

1-{2-(3,5-dimethylphenyl)-3-[2-(4-pyridin-4-yl-butylamino)ethyl]-1H-indol-5-yl}ethanol To a solution of 1-{2-(3,5-dimethylphenyl)-3-[2-(4-pyridin-4-yl-butylamino)ethyl]-1H-indol-5-yl}ethanone (45 mg in 2 mL dry tetrahydrofuran) at 0° C. was added 0.30 mL of a 1M solution of lithium aluminum hydride in tetrahydrofuran and the mixture stirred at low temperature. After 45 minutes, the reaction was quenched by the addition of saturated aqueous ammonium chloride and the mixture extracted with ethyl acetate. The organic portion was washed with brine, dried over sodium sulfate and purified by flash chromatography on silica gel (methylene chloride:methanol:ammonium hydroxide, 90:10:0.25) to give the title compound (40 mg). m/e=442 (M+H).

EXAMPLE 12.3

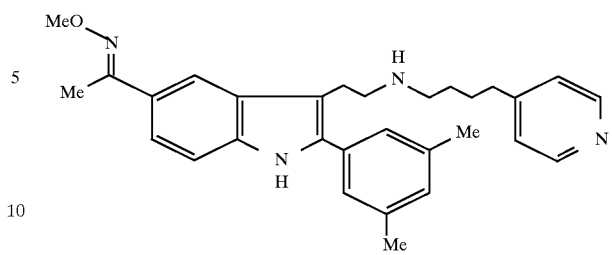

1-{2-(3,5-dimethylphenyl)-3 -[2-(4-pyridin-4-yl-butylamino)ethyl]-1H-indol-5-yl}ethanone O-methyloxime To a solution of 1-{2-(3,5-dimethylphenyl)-3-[2-(4-pyridin-4-yl-butylamino)ethyl]-1H-indol-5-yl}ethanone (22 mg in 0.50 mL methanol) was added 102 mg sodium acetate (trihydrate) followed by 63 mg methoxylamine hydrochloride and the mixture stirred at room temperature. After 20 hours, the mixture was concentrated in vacuo and the residue suspended in ethyl acetate, and washed successively with saturated aqueous sodium bicarbonate and brine. The organic portion was dried over sodium sulfate and the concentrate purified by preparative TLC on silica gel (methylene chloride:methanol:ammonium hydroxide, 90:10:0.25) to give the title compound (23 mg). m/e=469 (M+H).

Following a procedure similar to that described in EXAMPLES 12.1, 12.2 and 12.3, the following compounds were prepared:

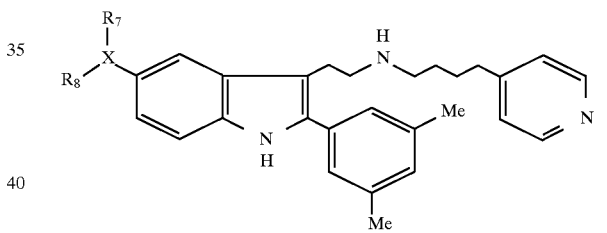

| Example # | XR$_7$,R$_8$ | m/e |
|---|---|---|
| 12A | -) | ▓▓▓ |
| 12B | -) | ▓▓▓ |
| 12C | -) | ▓▓▓ |
| 12D | -) | ▓▓▓ |

-continued

| Example # | XR7,R8 | m/e |
|---|---|---|
| 12E | (Me)(Me)CH-C(=O)-Me | 468 (M+H) |
| 12F | (Me)(Me)CH-CH(OH)-Me | 470 (M+H) |
| 12G | (Me)(Me)(Me)C-C(=O)-Me | 482 (M+H) |
| 12H | (Me)(Me)CH-CH2-C(=O)-Me | 482 (M+H) |
| 12I | Me-CH2-CH(Me)-C(=O)-Me | 482 (M+H) |
| 12J | Me-CH2-CH2-CH2-C(=O)-Me | 482 (M+H) |

EXAMPLE 13

Following procedures similar to that described in EXAMPLES 1 through 12, the following compounds are prepared:

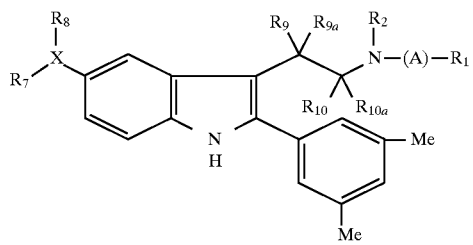

| Example # | X—R7, R8 | (R9, R9a, R10, R10a, R2, A, R1 chain) |
|---|---|---|
| 13A | Et2N-C(=O)-C(Me)2- | -CH(CH2Me)-CH2-NH-(CH2)4-(4-pyridyl) |
| 13B | Et2N-C(=O)-C(Me)2- | -CH(Me)-CH2-NH-(CH2)4-(3-pyridyl) |
| 13C | Et2N-C(=O)-C(Me)2- | -CH(CH2Me)-CH2-NH-(CH2)4-(4-pyridyl) |
| 13D | Et2N-C(=O)-C(Me)2- | -C(Me)2-CH2-NH-(CH2)4-(4-pyridyl) |
| 13E | Et2N-C(=O)-C(Me)2- | -C(Me)2-CH2-NH-(CH2)4-(3-pyridyl) |

| Example # | X—R$_7$, R$_8$ | (structure) |
|---|---|---|
| 13F | | |
| 13G | | |
| 13H | | |
| 13I | | |
| 13J | | |
| 13K | | |
| 13L | | |
| 13M | | |
| 13N | | |
| 13O | | |
| 13P | | |

-continued

| Example # | X—R₇, R₈ | R₉, R₉ₐ, R₂, R₁₀, R₁₀ₐ, N—(A)—R₁ |
|---|---|---|
| 13Q | Et₂N-C(O)-C(Me)₃ | iBu-NH-(CH₂)₃-(3-pyridyl) |
| 13R | Et₂N-C(O)-C(Me)₃ | nPr-NH-CF₂-(4-pyridyl) |
| 13S | Et₂N-C(O)-C(Me)₃ | nPr-NH-CF₂-(3-pyridyl) |
| 13T | Et₂N-C(O)-C(Me)₃ | iBu-NH-CF₂-(3-pyridyl) |
| 13U | Et₂N-C(O)-C(Me)₃ | iBu-NH-CF₂-(3-pyridyl) |
| 13V | (FCH₂CH₂)₂N-C(O)-C(Me)₃ | nPr-NH-(CH₂)₄-(4-pyridyl) |
| 13W | (FCH₂CH₂)₂N-C(O)-C(Me)₃ | iBu-NH-(CH₂)₄-(4-pyridyl) |
| 13X | (FCH₂CH₂)₂N-C(O)-C(Me)₃ | nPr-NH-(CH₂)₄-(4-pyridyl) |
| 13Y | (FCH₂CH₂)₂N-C(O)-C(Me)₃ | iBu-NH-(CH₂)₄-(4-pyridyl) |
| 13Z | (CF₃CH₂)₂N-C(O)-Et | nPr-NH-(CH₂)₄-(4-pyridyl) |

-continued

| Example # | X—R₇, R₈ | R₉, R₉ₐ, R₂, R₁₀, R₁₀ₐ, N—(A)—R₁ |
|---|---|---|
| 13AA | F₃C, F₃C, N-C(=O)-CH₂CH₃ | (R)-Me-CH(CH₃)-CH₂-NH-(CH₂)₄-(4-pyridyl) |
| 13BB | F₃C, F₃C, N-C(=O)-CH₂CH₃ | CH₃CH₂-NH-(CH₂)₄-(4-pyridyl) |
| 13CC | F₃C, F₃C, N-C(=O)-CH₂CH₃ | (S)-Me-CH(CH₃)-CH₂-NH-(CH₂)₄-(4-pyridyl) |
| 13DD | Me, Me, N-C(=O)-C(Me)₂-CH₃ | CH₃CH₂-NH-(CH₂)₂-(4-pyridyl) |
| 13EE | Me, Me, N-C(=O)-C(Me)₂-CH₃ | (R)-Me-CH(CH₃)-CH₂-NH-(CH₂)₂-(4-pyridyl) |
| 13FF | Me, Me, N-C(=O)-C(Me)₂-CH₃ | Et-CH-NH-CH-(CH₂)₃-(4-pyridyl) |
| 13GG | Me, Me, N-C(=O)-C(Me)₂-CH₃ | Et-CH-NH-CH-(CH₂)₃-(3-pyridyl) |
| 13HH | Me, Me, N-C(=O)-C(Me)₂-CH₃ | 5-ethyl-2-[3-(4-pyridyl)propyl]pyrrolidine |
| 13II | Me, Me, N-C(=O)-C(Me)₂-CH₃ | 5-ethyl-2-[3-(3-pyridyl)propyl]pyrrolidine |
| 13JJ | Me, Me, N-C(=O)-C(Me)₂-CH₃ | 6-ethyl-2-[3-(4-pyridyl)propyl]piperidine |
| 13KK | Me, Me, N-C(=O)-C(Me)₂-CH₃ | 6-ethyl-2-[3-(3-pyridyl)propyl]piperidine |

-continued

| Example # | X—R₇, R₈ | ![structure](R₉, R₉ₐ, R₂, R₁₀, R₁₀ₐ, N—(A)—R₁) |
|---|---|---|
| 13LL | Et₂N-C(O)-C(Me)₃ (N,N-diethyl pivalamide) | H-N-propyl-CF₂-CH₂-CH₂-(4-pyridyl) |
| 13MM | Et₂N-C(O)-C(Me)₃ | H-N-propyl-CHF-CH₂-CH₂-(4-pyridyl) |
| 13NN | Et₂N-C(O)-C(Me)₃ | propyl-NH-(CH₂)₃-C(=CH-C(O)NH-)-aryl(4-Cl, 2-) |
| 13OO | (iBu)₂N-C(O)-Me | propyl-NH-(CH₂)₃-C(=CH-C(O)NH-)-aryl(4-Cl, 2-) |
| 13PP | Et₂N-C(O)-C(Me)₃ | propyl-NH-CH₂-CH₂-C(=CH-C(O)NH-)-aryl(4-Cl, 2-) |
| 13QQ | Et₂N-C(O)-C(Me)₃ | propyl-NH-(CH₂)₃-C(=CH-C(O)NH-)-aryl(4-Cl) |

What is claimed is:

1. A compound of the formula

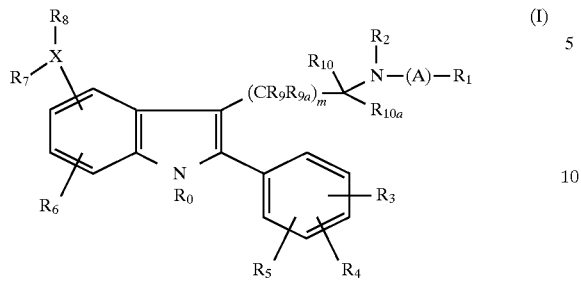

wherein

A is $C_1$–$C_6$ alkyl optionally substituted with one or more halogen, $C_3$–$C_7$ cycloalkyl, substituted $C_3$–$C_7$ cycloalkyl, $C_3$–$C_6$ alkenyl, substituted $C_3$–$C_6$ alkenyl, $C_3$–$C_6$ alkynyl, substituted $C_3$–$C_6$ alkynyl, $C_1$–$C_6$ alkoxy, or $C_0$–$C_5$ alkyl-S(O)$_n$-$C_0$–$C_5$ alkyl, $C_0$–$C_5$ alkyl-O-$C_0$–$C_5$ alkyl, $C_0$–$C_5$ alkyl-NR$_{18}$-$C_0$–$C_5$ alkyl where $R_{18}$ and the $C_0$–$C_5$ alkyl do not form a ring, or a single bond;

$R_0$ is hydrogen, $C_1$–$C_6$ alkyl, substituted $C_1$–$C_6$ alkyl, wherein the substituents are as defined below; aryl, substituted aryl, aralkyl or substituted aralkyl, wherein the substituents are as defined for $R_3$, $R_4$ and $R_5$;

$R_1$ is

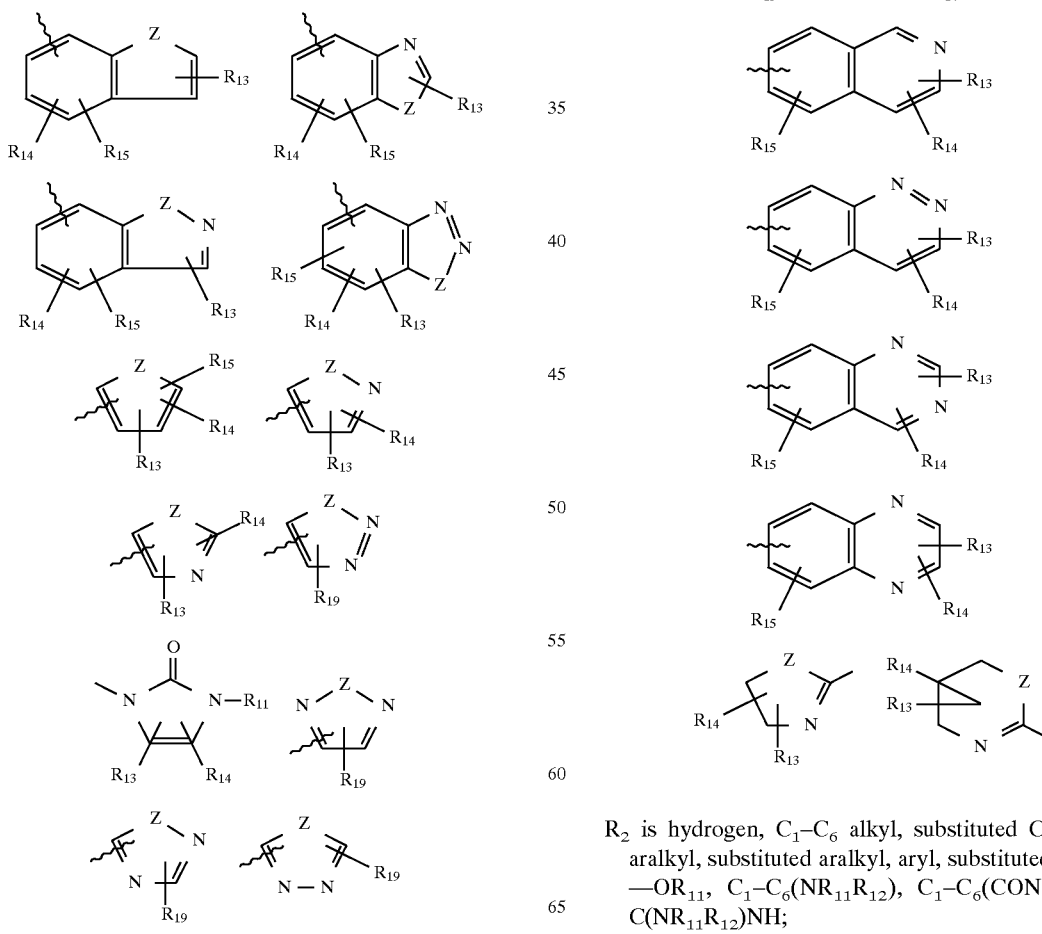

$R_2$ is hydrogen, $C_1$–$C_6$ alkyl, substituted $C_1$–$C_6$ alkyl, aralkyl, substituted aralkyl, aryl, substituted aryl, alkyl —OR$_{11}$, $C_1$–$C_6$(NR$_{11}$R$_{12}$), $C_1$–$C_6$(CONR$_{11}$R$_{12}$) or C(NR$_{11}$R$_{12}$)NH;

$R_2$ and A taken together form a ring of 5–7 atoms;

R₃, R₄ and R₅ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, or halogen;

R₆ is hydrogen, $C_1$–$C_6$ alkyl, substituted $C_1$–$C_6$ alkyl, aryl, substituted aryl, $C_1$–$C_3$ perfluoroalkyl, CN, NO₂, halogen, $R_{11}O(CH_2)_p$—, $NR_{12}C(O)R_{11}$, $NR_{12}C(O)NR_{11}R_{12}$ or $SO_nR_{11}$;

R₇ is hydrogen, $C_1$–$C_6$ alkyl, or substituted $C_1$–$C_6$ alkyl, unless X is hydrogen or halogen, then R₇ is absent;

R₈ is hydrogen, $C(O)OR_9$, $C(O)NR_{11}R_{12}$, $C(O)R_{11}$, $NR_{12}C(O)R_{11}$, $NR_{12}C(O)NR_{11}R_{12}$, $NR_{12}S(O)_2R_{11}$, $NR_{12}S(O)_2NR_{11}R_{12}$, $OC(O)R_{11}$, $OC(O)NR_{11}R_{12}$, $OR_{11}$, $SO_nR_{11}$, $S(O)_nNR_{11}R_{12}$, $C_1$–$C_6$ alkyl or substituted $C_1$–$C_6$ alkyl, unless X is hydrogen or halogen, then R₈ is absent; or R₇ and R₈ taken together form a carbocyclic ring of 3–7 atoms;

R₉ and R$_{9a}$ are independently hydrogen, $C_1$–$C_6$ alkyl, substituted $C_1$–$C_6$ alkyl; aryl or substituted aryl, aralkyl or substituted aralkyl when m≠0; or R$_{9a}$ and A taken together form a ring containing 3–7 carbon atoms when m≠0; or R₁₀ and R$_{10a}$ are independently hydrogen, $C_1$–$C_6$ alkyl, substituted $C_1$–$C_6$ alkyl, aryl, substituted aryl, aralkyl or substituted aralkyl;

R₁₁ and R₁₂ are independently hydrogen, $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

R₁₁ and R₁₂ taken together can form an optionally substituted ring of 3–7 atoms;

R₁₃ is hydrogen, OH, $NR_{20}R_{21}$, $NR_{11}SO_2(C_1$–$C_6$ alkyl), $NR_{11}SO_2$(substituted $C_1$–$C_6$ alkyl), $NR_{11}SO_2$(aryl), $NR_{11}SO_2$(substituted aryl), $NR_{11}SO_2(C_1$–$C_3$ perfluoroalkyl); $SO_2NR_{11}(C_1$–$C_6$ alkyl), $SO_2NR_{11}$(substituted $C_1$–$C_6$ alkyl), $SO_2NR_{11}$(aryl), $SO_2NR_{11}$(substituted aryl), $SO_2NR_{11}(C_1$–$C_3$ perfluoroalkyl); $SO_2NR_{11}(C(O)C_1$–$C_6$ alkyl); $SO_2NR_{11}(C(O)$-substituted $C_1$–$C_6$ alkyl); $SO_2NR_{11}(C(O)$-aryl); $SO_2NR_{11}(C(O)$-substituted aryl); $S(O)_n(C_1$–$C_6$ alkyl); $S(O)_n$(substituted $C_1$–$C_6$ alkyl), $S(O)_n$(aryl), $S(O)_n$(substituted aryl), $C_1$–$C_3$ perfluoroalkyl, $C_1$–$C_3$ perfluoroalkoxy, $C_1$–$C_6$ alkoxy, substituted $C_1$–$C_6$ alkoxy, COOH, halogen, NO₂ or CN;

R₁₄ and R₁₅ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein R₁₇ is hydrogen, $C_1$–$C_6$ alkyl, $C_1$–$C_3$ perfluoroalkyl, aryl or substituted aryl; or R₁₃ and R₁₄ taken together form an oxo group;

R₁₈ is hydrogen;

R₁₉ is either the definition of R₁₃ or R₁₄;

R₂₀ and R₂₁ are independently hydrogen, $C_1$–$C_6$ alkyl or substituted $C_1$–$C_6$ alkyl;

X is hydrogen, halogen, N, O, $S(O)_n$, C(O), $(CR_{11}R_{12})_p$; when X is hydrogen or halogen, R₇ and R₈ are absent; when X is O, S(O)n, C(O), or $CR_{11}R_{12}$ only one of R₇ or R₈ is present;

Z is O, S, or $NR_{11}$; with the proviso that if only one heterocyclic atom is present it must be N;

m is 0–3;

n is 0–2;

p is 0–; and the alkyl, alkenyl and alkynyl substituents are selected from $C_1$–$C_6$ alkyl, $C_3$–$C_7$ cycloalkyl, aryl, substituted aryl, aralkyl, substituted aralkyl, hydroxy, oxo, cyano, $C_1$–$C_6$ alkoxy, fluoro, COOH, C(O)O ($C_1$–$C_6$)alkyl, aryl $C_1$–$C_3$ alkoxy, substituted aryl $C_1$–$C_3$ alkoxy, and the aryl substituents are as defined for R₃, R₄ and R₅;

or a pharmaceutically acceptable addition salt and/or hydrate thereof, or where applicable, a geometric or optical isomer or racemic mixture thereof.

2. The compound according to claim 1 of the formula

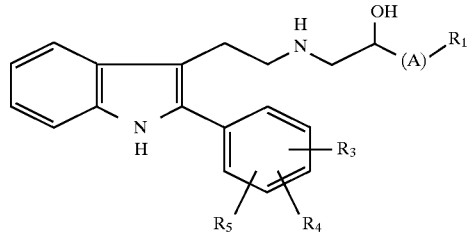

wherein R₁, R₃, R₄, and R₅ and A are as indicated in the table below:

| R₁ | R₃,R₄,R₅ | A |
|---|---|---|
| Pyridine-NH—COCH₃ | 3,4-OMe | CH₂—O |
| Pyridine-NH₂ | 3,4-OMe | CH₂—O |

3. The compound according to claim 1 of the formula

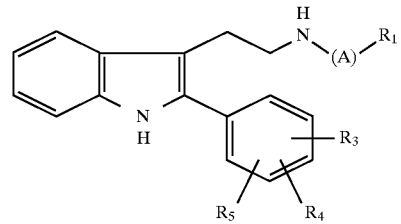

wherein R₁, R₃, R₄, R₅ and A are as indicated in the table below:

| R₁ | R₃,R₄,R₅ | A = (CH₂)ₙ |
|---|---|---|
| 5-Indole | 3,4-OMe | 1 |
| 5-Benzimidazole | 3,4-OMe | 1 |
| 4-Indole | 3,4-OMe | 1 |
| 3-pyridyl | 3,5-Me | 5 |
| 4-pyridyl | 3,5-Me | 4 |
| 2-pyridyl | 3,5-Me | 4 |
| 3-pyridyl | 3,5-Me | 4 |
| 5-pyrimidine | 3,5-Me | 4 |
| 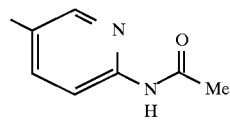 | 3,5-Me | 4 |
|  | 3,5-Me | 4 |

-continued

| R₁ | R₃,R₄,R₅ | A = (CH₂)ₙ |
|---|---|---|
| 6-methyl-2-pyridone (NH-C=O) | 3,5-Me | 4 |
| 4-methyl-pyridine N-oxide | 3,5-Me | 4 |
| 5-methyl-2-aminopyridine | 3,5-Me | 4 |
| 5-methyl-2-(methylsulfonamido)pyridine | 3,5-Me | 4 |
| 4-pyridyl | 3,5-Me | 2 |
| 3-pyridyl | 3,5-Me | 2 |
| 2-pyridyl | 3,5-Me | 2 |
| 4-imidazolyl | 3,5-Me | 2 |
| 4-pyridyl | 3,5-Me | 1 |
| 2-pyridyl | 3,5-Me | 1 |
| 3-pyridyl | 3,5-Me | 1 |
| 3-pyridyl | 3,5-Me | 3 |
| 4-pyridyl | 3,5-Me | 3 |
| 3-quinolinyl | 3,5-Me | 4 |
| 4-pyridyl | 3,5-Me | 5 |
| 5-indole | 3,4-OMe | 3 |
| 3-methylquinoline | 3,5-Me | 4 |

4. The compound according to claim 1 of the formula

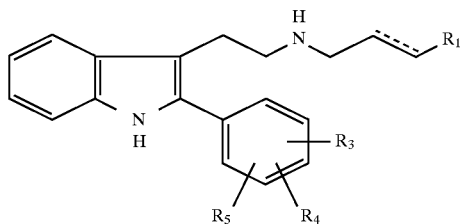

wherein R₁, R₃, R₄, R₅ and X–R₇, R₈ are as indicated in the table below:

| X—R₇,R₈ | R₁ | R₃,R₄,R₅ |
|---|---|---|
| H | 5-Benzimidazole-N—SO₂Me | 3,4-OMe |
| H | 5-Benzimidazole | 3,4-OMe |

5. The compound according to claim 1 of the formula

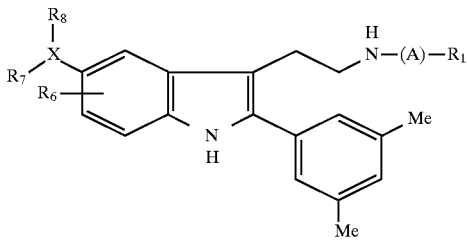

wherein A, R₁, R₆ and X–R₇, R₈ are as indicated in the table below:

| X—R₇,R₈ | A = (CH₂)ₙ | R₁ |
|---|---|---|
| * | 4 | 4-pyridyl |
| Br | ** | 4-pyridyl |
| —NH₂ | 4 | 4-pyridyl |
| —NH—COCH₃ | 4 | 4-pyridyl |
| —NH—CO—N(CH₂CH₃)₂ | 4 | 4-pyridyl |
| —NH—CO—N(CH₂CH₃)₂ | 4 | 3-pyridyl |
| —NH—CO—N(CH₂CH₃)₂ | 4 | 6-methoxy-3-pyridyl |
| —NH—CO—N(CH₃)₂ | 5 | 3-pyridyl |
| —NH—CO—N(CH₂CH₃)₂ | 5 | 3-pyridyl |
| —NH—CO—N(CH₂CH₃)₂ | 5 | 4-pyridyl |
| —NH—CO—N(CH₃)₂ | 4 | 6-methoxy-3-pyridyl |
| —SO₂—CH₂—CO—Me | 4 | 4-pyridyl |
| MeCH(OH)CH₂SO₂— | 4 | 4-pyridyl |
| MeCH=CH—SO₂— | 4 | 4-pyridyl |
| MeCH₂CH₂—SO₂— | 4 | 4-pyridyl |
| MeSO₂— | 4 | 3-pyridyl |
| MeSO₂— | 4 | 6-methoxy-3-pyridyl |
| MeSO₂— | 4 | 4-methyl-2-pyridone |
| MeSO₂— | 5 | 4-pyridyl |
| MeSO₂— | 5 | 3-pyridyl |
| Me₂N—C(=O)—CH₂—SO₂—Me (diethylamide) | 4 | 4-pyridyl |
| MeSO₂— | 4 | 4-pyridyl |
| —NH—CO—N(CH₃)₂ | 5 | 4-pyridyl |

*—R₆ = 5-NO₂
**—R₆ = Br

6. The compound according to claim 1 of the formula

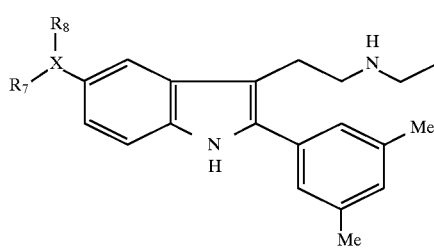

wherein $R_1$, $R_6$ and $X-R_7$, $R_8$ are as indicated in the table below:

| $X-R_7R_8$ | R | $R_1$ |
|---|---|---|
| Me-O-C(=O)-CH2- | H | 4-pyridyl |
| Me-O-C(=O)-CH2- | H | 3-pyridyl |
| Me2N-C(=O)-CH2- | H | 3-pyridyl |
| Me2N-C(=O)-CH2- | H | 4-pyridyl |
| Et2N-C(=O)-CH2- | H | 3-pyridyl |
| (F3CCH2)2N-C(=O)-CH2- | H | 4-pyridyl |
| HOCH2CH2(Me)N-C(=O)-CH2- | H | 3-pyridyl |
| HOCH2CH2(Me)N-C(=O)-CH2- | H | 4-pyridyl |
| (MeOCH2CH2)2N-C(=O)-CH2- | H | 3-pyridyl |
| (HOCH(Me)CH2)2N-C(=O)-CH2- | H | 3-pyridyl |
| Cyclohexyl(Et)N-C(=O)-CH2- | H | 3-pyridyl |
| Cyclohexyl(Et)N-C(=O)-CH2- | H | 4-pyridyl |
| Cyclopentyl(nPr)N-C(=O)-CH2- | H | 4-pyridyl |
| (nBu)2N-C(=O)-CH2- | H | 3-pyridyl |
| (nBu)2N-C(=O)-CH2- | H | 4-pyridyl |
| iPr(H)N-C(=O)-CH2- | H | 3-pyridyl |
| (iPr)2N-C(=O)-CH2- | H | 4-pyridyl |
| iPr(Et)N-C(=O)-CH2- | H | 3-pyridyl |
| Bn(Et)N-C(=O)-CH2- | H | 3-pyridyl |
| Bn(Et)N-C(=O)-CH2- | H | 4-pyridyl |

-continued

| X—R₇R₈ | ▨ | R₁ |
|---|---|---|
|  | H | 3-pyridyl |
| —CON(Et)₂ | H | 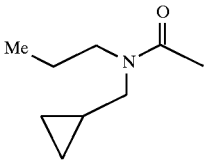 |
| —COOMe | 6-Cl | 4-pyridyl |
| —CON(iBu)₂ | 6-Cl | 4-pyridyl |
| —CON(Et)₂ | H | 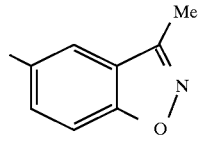 |
| —CON(CH₂CH₂CN)—cyclohexyl | H | 4-pyridyl |
| 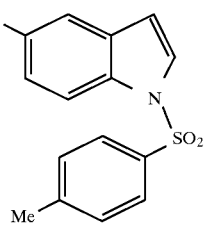 | H | 4-pyridyl |
| —COOMe | 4-Cl | 4-pyridyl |
| —CON(iBu)₂ | 4-Cl | 4-pyridyl |
| —CON(Et)₂ | 6-Cl | 4-pyridyl |

7. The compound according to claim 1 of the formula

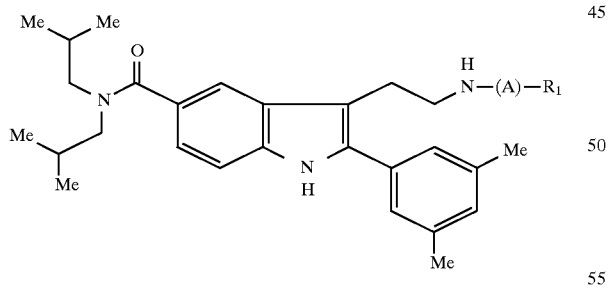

wherein R₁ and A are as indicated in the table below:

| A = (CH₂)ₙ | R₁ |
|---|---|
| 4 | 4-pyridyl |
| 4 | 3-pyridyl |
| 4 | 6-amino-3-pyridyl |
| 4 | 6-amino-3-pyriydl |
| 4 | 6-methoxy-3-pyridyl |

-continued

| A = (CH₂)ₙ | R₁ |
|---|---|
| 4 | 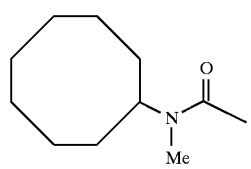 |
| 4 | 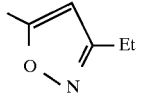 |
| 4 | 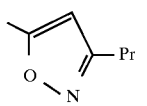 |
| 4 | 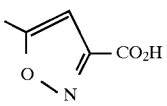 |
| 4 | 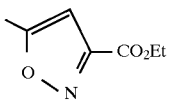 |
| 4 | 2-cyano-4-pyridyl |
| 4 | 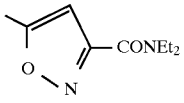 |
| 4 | 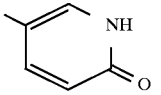 |
| 4 | 2-(CH₂NH—Boc)-4-pyridyl |
| 4 | 2-(CH₂NH₂)-4-pyridyl |
| 4 | 6-(SMe)-3-pyridyl |
| 4 | 5-carboethoxy-3-pyridyl |
| 4 | 6-(NHCOOEt)-3-pyridyl |
| 4 | 2,3,5,6-tetrafluoro-4-pyridyl |
| 3 | 3-pyridyl |
| 4 | 6-[NHS(O)₂CF₃]-3-pyridyl |
| 4 | 6-[NHS(O)₂CH₃]-3-pyridyl |
| 4 | 5-cyano-3-pyridyl |
| 4 | 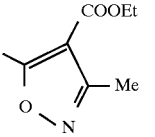 |
| 4 | 3,5-dichloro-4-pyridyl |
| 4 | 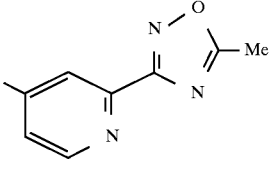 |

8. The compound according to claim 1 of the formula
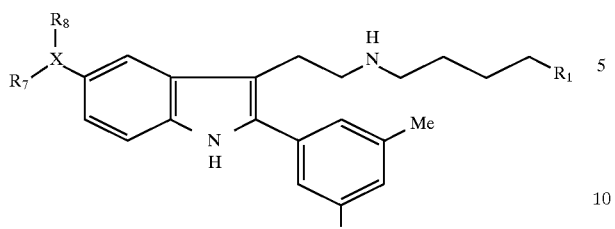
wherein $R_1$ and $X-R_7, R_8$ are as indicated in the table below:
| $X-R_7,R_8$ | $R_1$ |
|---|---|
| 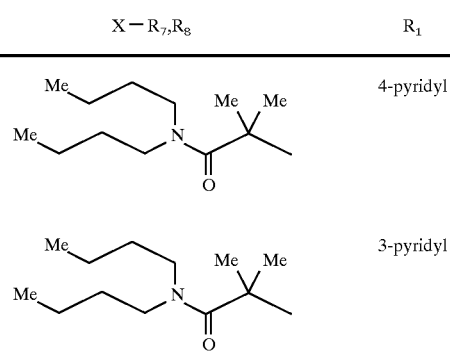 | 4-pyridyl |
| | 3-pyridyl |
| | 3-pyridyl |
| | 4-pyridyl |
| | 4-pyridyl |
| | 3-pyridyl |
| | 4-pyridyl |
| | 4-pyridyl |
-continued
| $X-R_7,R_8$ | $R_1$ |
|---|---|
| 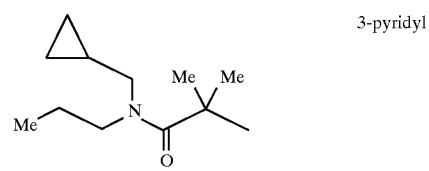 | 4-pyridyl |
| | 3-pyridyl |
| 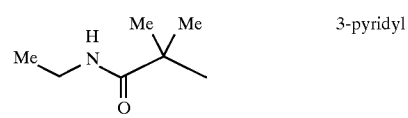 | 3-pyridyl |
| 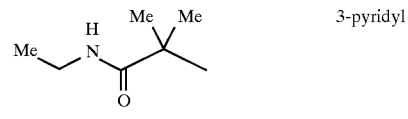 | 3-pyridyl |
| 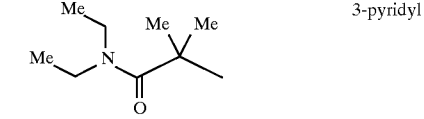 | 3-pyridyl |
| 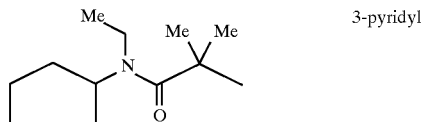 | 3-pyridyl |
| 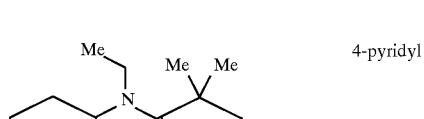 | 3-pyridyl |
| 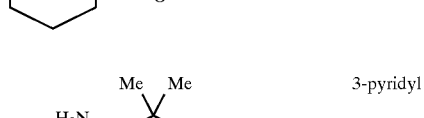 | 4-pyridyl |
| 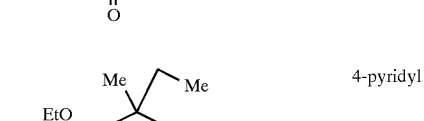 | 3-pyridyl |
| | 4-pyridyl |

9. The compound according to claim 1 of the formula

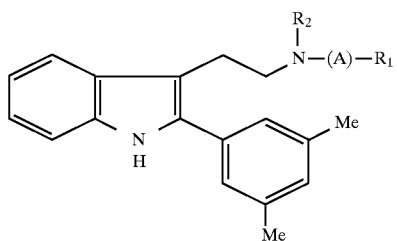

wherein $R_1$, $R_2$ and A are as indicated in the table below:

| (A) | $R_2$ | $R_1$ |
|---|---|---|
| —CH₂CH₂— | —(CH₂)₄-4-(phenyl-4-OMe) | 4-pyridyl |
| —CH₂CH₂— | —(CH₂)₄-4-(phenyl-4-OH) | 4-pyridyl |
| —CH₂C(Me)₂CH₂CH₂— | —H | 4-pyridyl |
| 1,3-cyclohexyl | —H | 3-pyridyl |
| 1,3-cyclopentyl | —H | 3-pyridyl |
| 1,4-cyclohexyl-OH | —H | 3-pyridyl |

10. The compound according to claim 1 of the formula

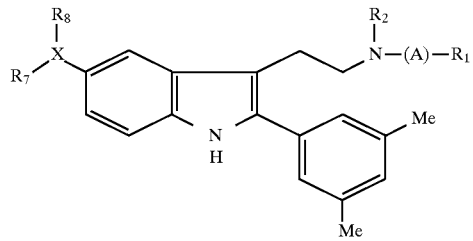

wherein A, $R_1$, $R_2$ and $XR_7$, $R_8$ are as indicated in the table below:

| —N($R_2$)—(A)— | $XR_7$,$R_8$ | $R_1$ |
|---|---|---|
| N-piperidinyl-CO₂Et | —NH—CO—N(Et)₂ | 3-pyridyl |
| N-piperidinyl-CO₂Et | —NH—CO—N(Et)₂ | 3-pyridyl |
| N-piperidinyl-CO₂Et | —NH—CO—(4-morpholine) | 3-pyridyl |
| N-piperidinyl-CO₂Et | —NH—CO—(4-morpholine) | 3-pyridyl |
| N-piperidinyl (4-Me) | —NH—CO—N(Et)₂ | 3-pyridyl |
| piperazinyl | —H | 3-pyridyl |
| piperazinyl | —H | 4-pyridyl |
| piperazinyl (dimethyl) | —H | 4-pyridyl |
| —NHCH₂CH₂CH₂O— | —COOEt | 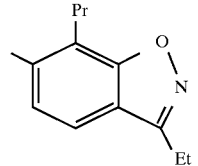 |
| 4-methylamino-4-methyl-4-OH-cyclohexyl | C(O)N—(iBu)₂ | 4-pyridyl |
| —NHCH₂CH₂CH₂O— | C(O)N—(iBu)₂ | 3-pyridyl |
| —NHCH(Me)CH₂CH₂— | C(O)N—(iBu)₂ | 3-pyridyl |
| —NHCH(Me)CH₂CH₂CH₂— | C(O)N—(iBu)₂ | 4-pyridyl |
| (cis)-NHCH₂CH=CH— | C(O)N—(iBu)₂ | 3-pyridyl |
| (trans)-NHCH₂CH=CH— | C(O)N—(iBu)₂ | 3-pyridyl |
| —NHCH₂CH₂CH(Me)— | C(O)N—(iBu)₂ | 4-pyridyl |
| —NHCH₂CH₂CH(Me)— | C(O)N—(iBu)₂ | 3-pyridyl |
| —NHCH₂CH₂—O—CH₂— | C(O)N—(iBu)₂ | 3-pyridyl |
| —N(Et)—CH₂CH₂CH₂CH₂— | C(Me)₂—C(O)N—(iBu)₂ | 4-pyridyl |
| —NHCH₂CH(CH₃)CH₂CH₂— | C(O)N—(iBu)₂ | 3-pyridyl |
| —NHCH₂CH₂CH₂—CH(CH₃)— | C(O)N—(iBu)₂ | 4-pyridyl |
| —NHCH₂CH₂—CH(CH₃)CH₂— | C(O)N—(iBu)₂ | 3-pyridyl |
| —NHCH(CH₃)CH₂— | C(O)N—(iBu)₂ | 3-pyridyl |
| —N(Me)—CH₂CH₂CH₂CH₂— | C(O)N—(Et)₂ | 4-pyridyl |
| —NHC(CH₃)₂CH₂CH₂—CH₂— | C(O)N—(iBu)₂ | 3-pyridyl |
| —NHC(CH₃)₂CH₂CH₂—CH(OH)— | C(O)N—(iBu)₂ | 3-pyridyl |
| —NHC(CH₃O₂CH=CH—CH(OH)— | C(O)N—(iBu)₂ | 3-pyridyl |
| —NHC(CH₃)₂CH₂CH₂— | C(Me)₂— | 3-pyridyl |

-continued

| —N(R₂)—(A)— | XR₇,R₈ | R₁ |
|---|---|---|
| CH₂— | C(O)N—(Et)₂ | |
| —NHCH₂CH₂— | C(O)N—(iBu)₂ | 3-pyridyl |
| —NHCH₂CH₂— | C(Me)₂—C(O)N—(Et)₂ | 3-pyridyl |
| —NHC(CH₃)₂CH=CH—CH(OH)— | C(O)N—(iBu)₂ | 4-pyridyl |
| —NHC(CH₃O₂CH₂CH₂—CH(OH)— | C(O)N—(iBu)₂ | 4-pyridyl |
| —NHC(CH₃)₂CH₂CH₂—CH₂— | C(O)N—(iBu)₂ | 4-pyridyl |
| —NHC(CH₃)₂CH=CH—CH(OH)— | C(Me)₂—C(O)N—(Et)₂ | 4-pyridyl |
| —NHC(CH₃)₂CH₂CH₂—CH₂— | C(Me)₂—C(O)N—(Et)₂ | 4-pyridyl |
| —NHCH₂CH(CH₃)CH₂—CH₂— | C(O)N—(iBu)₂ | 4-pyridyl |
| —NHCH₂—CH(CH₂CH₃)CH₂CH₂— | C(O)N—(iBu)₂ | 4-pyridyl |
| —NHCH₂CH₂— | C(Me)₂—C(O)N—(Et)₂ | 4-pyridyl |
| —NHCH₂CH₂— | C(O)N—(iBu)₂ | 4-pyridyl |

11. The compound according to claim 1 of the formula

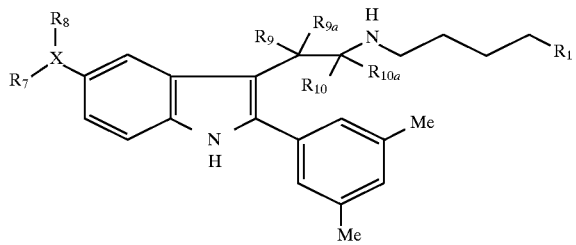

wherein R₁, XR₇, R₈, R₉, R₉ₐ, R₁₀ and R₁₀ₐ are as indicated in the table below:

| R₉R₉ₐR₁₀R₁₀ₐ structure | XR₇,R₈ | (CH₂)ₙ | R₁ |
|---|---|---|---|
| MeO-CH₂-CH(Me)-CH₂-NHMe | —NHC(O)Ph | 4 | 4-pyridyl |
| Me-CH(Me)-CH₂-NHMe | EtO-C(O)-C(Me)₂ | 4 | 4-pyridyl |
| Me-CH(Me)-CH₂-NHMe | (Et)₂N-C(O)-C(Me)₂ | 4 | 4-pyridyl |
| Me-CH(Me)-CH₂-NHMe | (Et)₂N-C(O)-C(Me)₂ | 4 | 3-pyridyl |

| R₉R₉ₐR₁₀R₁₀ₐ structure | XR₇,R₈ | (CH₂)ₙ | R₁ |
|---|---|---|---|
| Me-CH(Me)-CH₂-NHMe (R) | (Et)₂N-C(O)-C(Me)₂ | 4 | 4-pyridyl |
| Me-CH(Me)-CH₂-NHMe (S) | (Et)₂N-C(O)-C(Me)₂ | 4 | 4-pyridyl |
| Me-CH(Me)-CH₂-NHMe | (Bui)₂N-C(O)-C(Me)₂ | 4 | 3-pyridyl |
| Et-CH(Me)-NHMe | (Et)₂N-C(O)-C(Me)₂ | 4 | 3-pyridyl |
| Me-CH(Me)-CH₂-NHMe | EtO-C(O)-C(Me)₂ | 2 | 3-pyridyl. |

12. The compound according to claim 1 of the formula

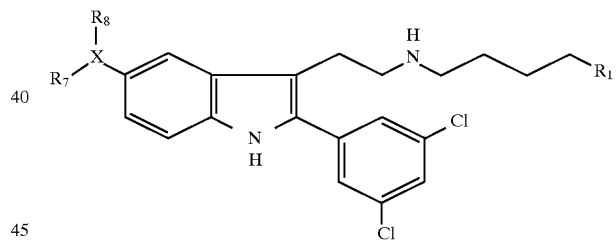

wherein R₁ and XR₇, R₈ are as indicated in the table below:

| XR₇,R₈ | R₁ |
|---|---|
| Me-N(Et)-C(O)-C(Me)₂ with Me | 3-pyridyl |
| —COOEt | 3-pyridyl |
| —CON(iBu)₂ | 3-pyridyl |
| —CON(nBu)₂ | 3-pyridyl |
| —CON(Et)₂ | Me-C(O)- |
| —CON(Et)₂ | 3-pyridyl |

13. The compound according to claim 1 of the formula
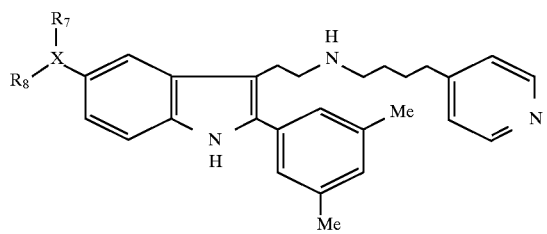
wherein $XR_7$, $R_8$ is as indicated in the table below:
| $XR_7, R_8$ |
|---|
| 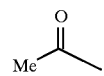 |
| 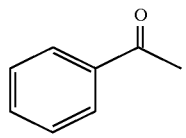 |
| 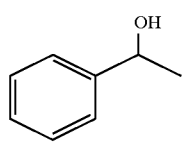 |
| 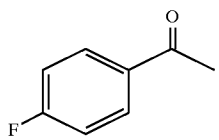 |
| 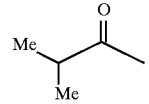 |
| 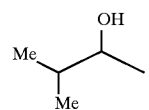 |
| $XR_7, R_8$ |
|---|
| 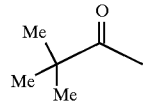 |
| 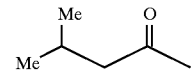 |
| 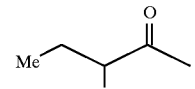 |
| 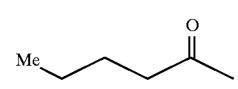 |
| 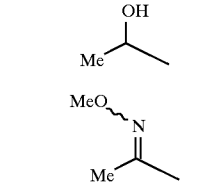 |
14. The compound according to claim 1 of the formula
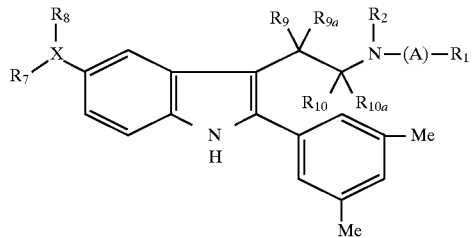
wherein A, $R_1$, $R_2$, $XR_7$, $R_8$, $R_9 R_{9a} R_{10}$ and $R_{10a}$ are as indicated in the table below:
| X—$R_7$, $R_8$ | $R_9$ $R_{9a}$ $R_2$ <br> \|  \|  \| <br> N—(A)—$R_1$ <br> \|  \| <br> $R_{10}$ $R_{10a}$ |
|---|---|
| 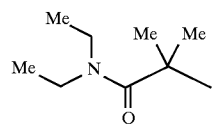 | 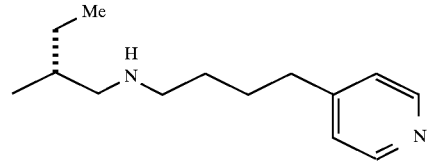 |
| 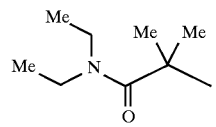 | 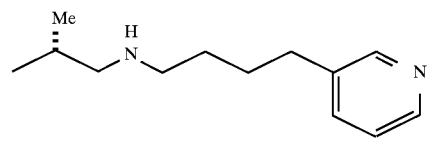 |

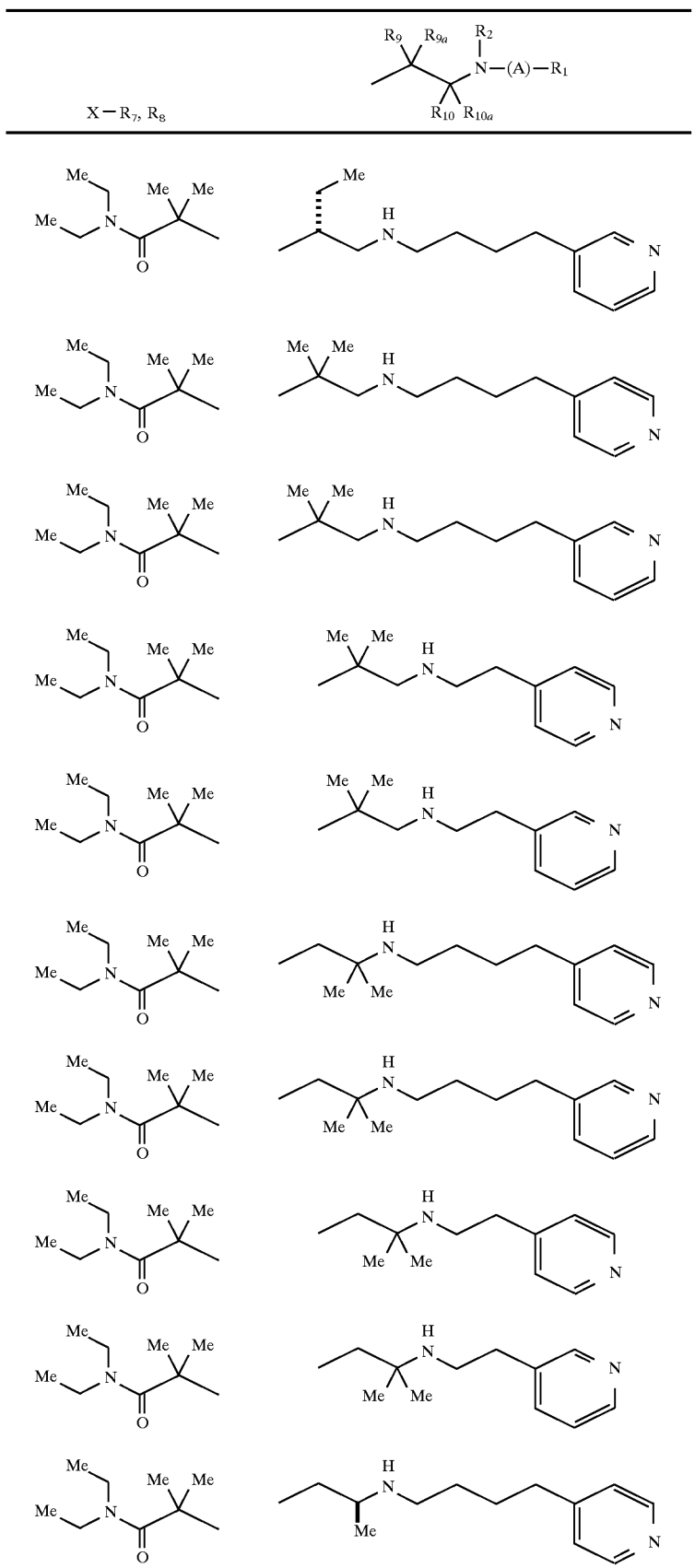

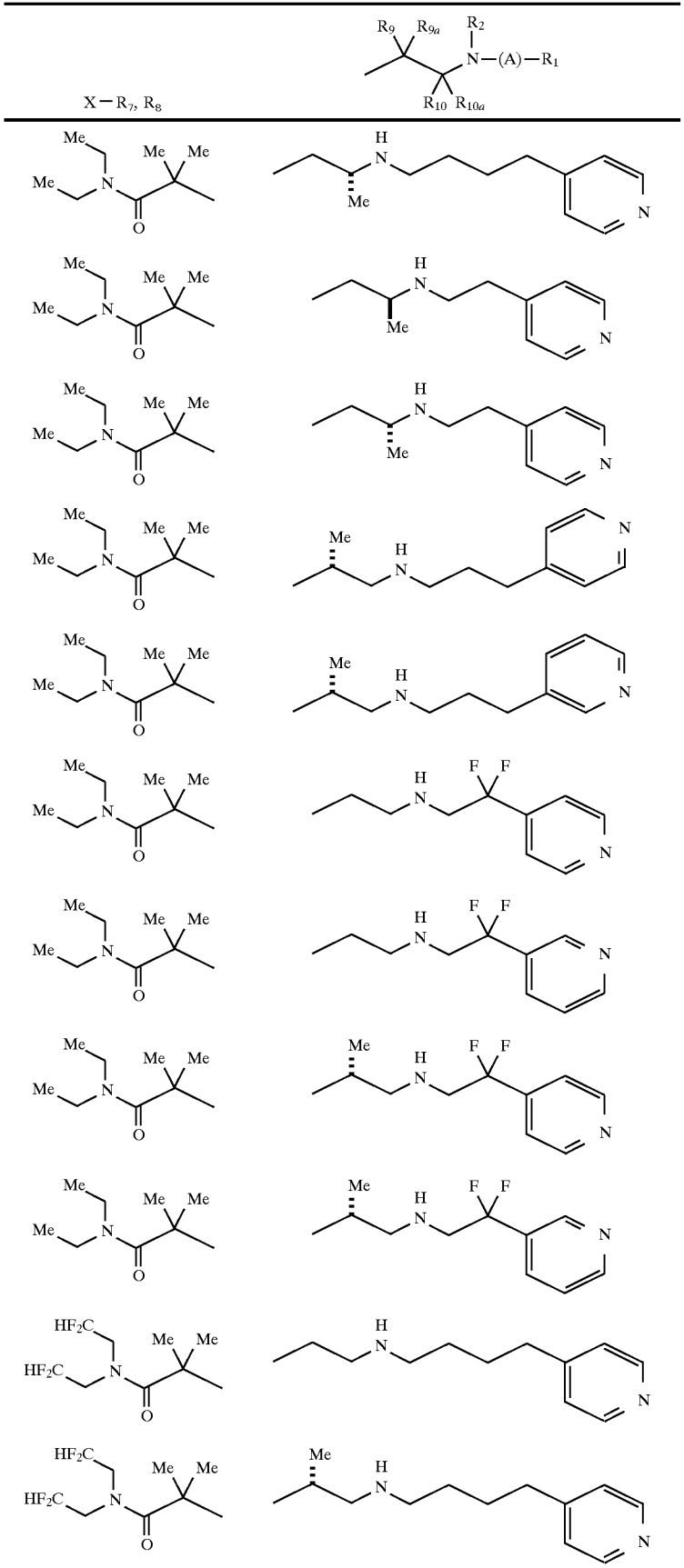

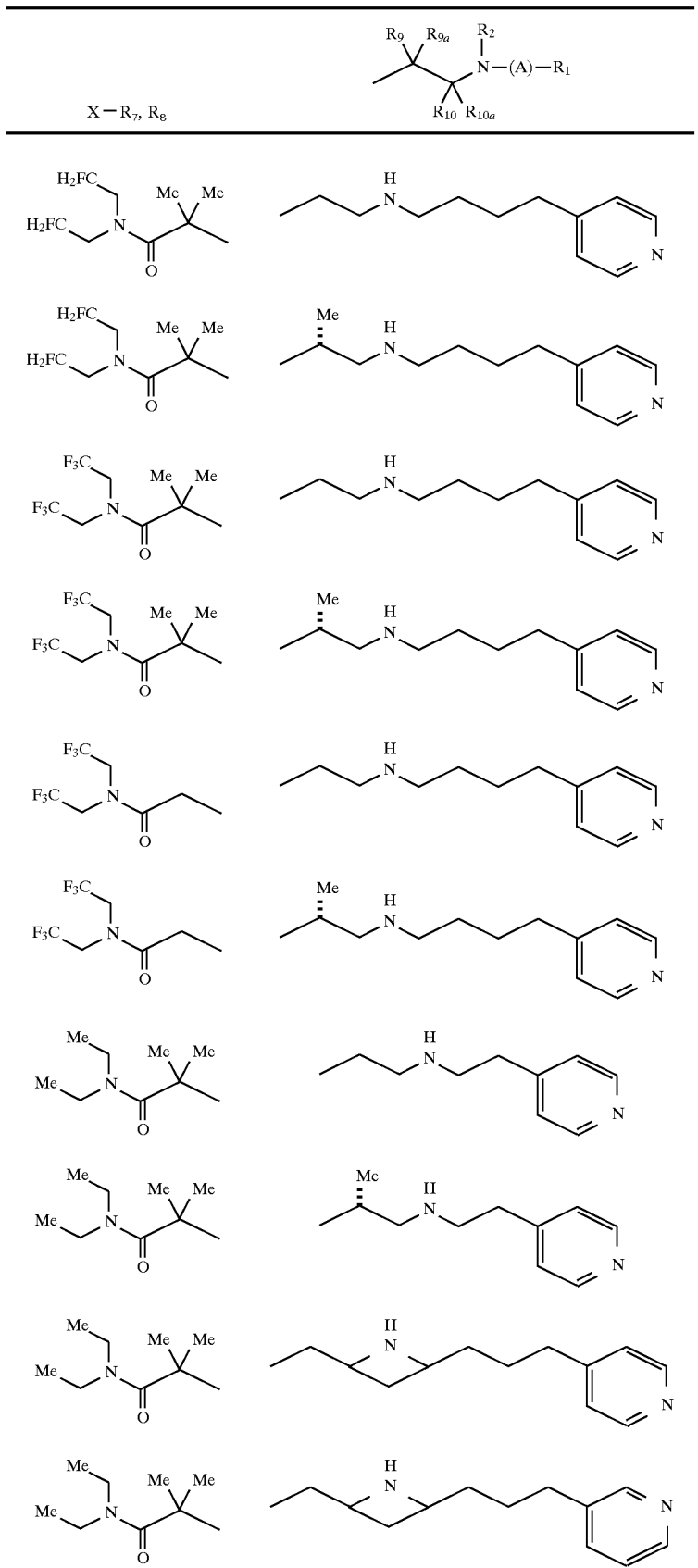

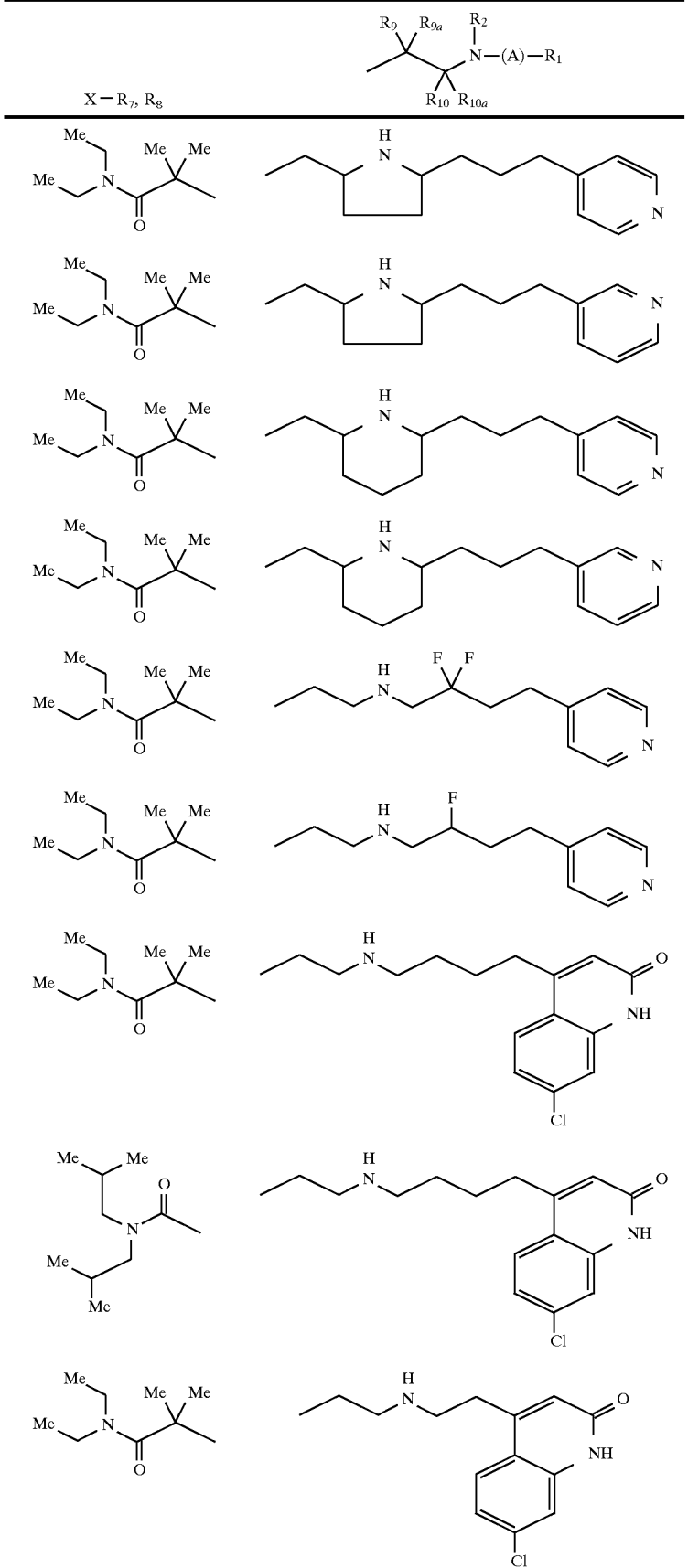

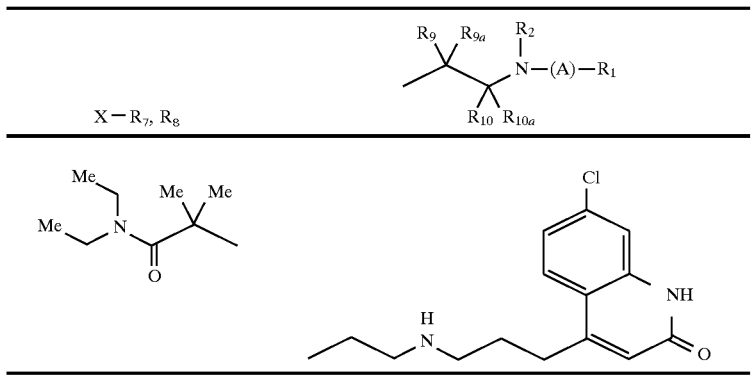

15. The compound as defined in claim 1 which is
    a) 1-[2-[2-(3,4-dimethoxyphenyl)-1H-indol-3-yl]ethylamino]-3-(pyridin-4-yloxy)propan-2-ol;
    b) [2-[2-(3,5-dimethylphenyl)-5-methanesulfonyl-1H-indol-3-yl]ethyl]-(4-pyridin-4-yl-butyl)amine; and
    c) 3-[2-(3,5-dimethylphenyl)-3-[2-(5-pyridin-4-yl-pentylamino)-ethyl]-1H-indol-5-yl]- 1,1-dimethylurea.

16. A pharmaceutical composition which comprises an effective amount of a compound as defined in claim 1 and a pharmaceutically acceptable carrier therefor.

17. A method for antagonizing gonadotropin-releasing hormone in a subject suffering from a gonadotropin-releasing hormone derived disorder which comprises administering to said subject an effective amount of a compound as defined in claim 1.

18. A method according to claim 17 wherein the gonadotropin-releasing hormone derived disorder is a sex-hormone related condition.

19. A method according to claim 17 wherein the gonadotropin-releasing hormone derived disorder is a sex hormone dependent cancer, benign prostatic hypertropy or myoma of the uterus.

20. A method according to claim 19 wherein the sex hormone dependent cancer is selected from the group consisting of prostatic cancer, uterine cancer, breast cancer and pituitary gonadotrophe adenomas.

21. A method according to claim 18 wherein the sex hormone dependent condition is selected from the group consisting of endometriosis, polycystic ovarian disease, uterine fibroids and precocious puberty.

22. A method for preventing pregnancy in a subject in need thereof which comprises administering an effective amount of a compound as defined in claim 1.

23. A method for treating irritable bowel syndrome in a subject in need thereof which comprises administering to said subject an effective amount of a compound as defined in claim 1.

24. A method for treating hirsutism in a subject in need thereof which comprises administering to said subject an effective amount of a compound as defined in claim 1.

25. A pharmaceutical composition which comprises an inert carrier and an effective amount of a compound which stimulates the endogenous production or release of growth hormone in combination with a compound as defined in claim 1.

26. A pharmaceutical composition made by combining the compound of claim 1 and a pharmaceutically acceptable carrier therefor.

27. A process for making a pharmaceutical composition comprising combining a compound of claim 1 and a pharmaceutically acceptable carrier.

* * * * *

UNITED STATES PATENT AND TRADEMARK OFFICE
CERTIFICATE OF CORRECTION

PATENT NO. : 5,849,764
DATED : December 15, 1998
INVENTOR(S) : Mark Goulet, Lin Chu, Thomas F. Walsh, Michael H. Fisher, Narindar N. Girotra, Matthew J. Wyvratt, Peter Lin and Wallace T. Ashton It is certified that error appears in the above-identified patent and that said Letters Patent is hereby corrected as shown below:

In claim 1, column 91, delete line 10, and replace it with the following:

-- $R_8$ is hydrogen, $(C(O)OR_9, C(O)NR_{11}R_{12}, NR_{11}R_{12}, C(O)R_{11}$, --

In claim 1, column 92, line 3, after "p is 0-", please insert -- 4 --.

In claim 8, column 99, line 59, replace "4-pyridyl" with -- 3-pyridyl --.

In claim 8, column 100, between lines 25-30, replace the structure with the following:

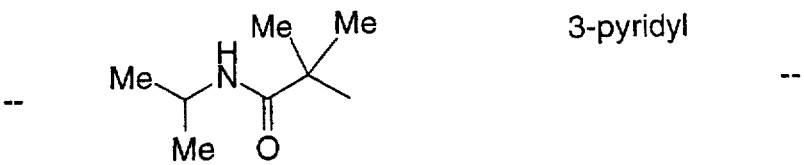

--    3-pyridyl    --

In claim 10, column 102, line 64, replace "-NHC(CH$_3$O$_2$CH=CH-" with -- -NHC(CH$_3$)$_2$CH=CH- --.

UNITED STATES PATENT AND TRADEMARK OFFICE
CERTIFICATE OF CORRECTION

PATENT NO. : 5,849,764
DATED : December 15, 1998
INVENTOR(S) : Mark Goulet, Lin Chu, Thomas F. Walsh, Michael H. Fisher, Narindar N. Girotra, Matthew J. Wyvratt, Peter Lin and Wallace T. Ashton It is certified that error appears in the above-identified patent and that said Letters Patent is hereby corrected as shown below:

In claim 10, column 103, line 12, replace "-NHC(CH$_3$O$_2$CH$_2$CH$_2$-" with -- -NHC(CH$_3$)$_2$CH$_2$CH$_2$- -- .

In claim 11, column 103, line 41, replace "R$_{b\ 9a}$," with -- R$_{9a}$, -- .

In claim 12, column 104, the structure at line 55, should be the following:

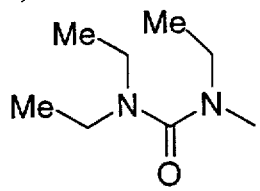

In claim 12, column 104, the structure between lines 61 and 64 should be the following:

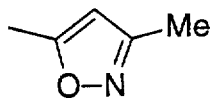

In claim 14, column 106, line 46, replace "R$_9$R$_{9a}$R$_{10}$" with -- R$_9$, R$_{9a}$, R$_{10}$ -- .

Signed and Sealed this

Third Day of August, 1999

Attest:

Q. TODD DICKINSON

Attesting Officer        Acting Commissioner of Patents and Trademarks